United States Patent [19]

Furneaux et al.

[11] Patent Number: 5,047,518
[45] Date of Patent: Sep. 10, 1991

[54] 1,6-ANHYDRO-β-HEXOPYRANOSE DERIVATIVES AND THEIR USE AS HERBICIDES AND PLANT GROWTH REGULATORS

[75] Inventors: Richard H. Furneaux, Wilton; Ronald F. Henzell, Hamilton; Peter C. Tyler, Northland, all of New Zealand

[73] Assignee: Her Majesty the Queen in right of New Zealand, Wellington, New Zealand

[21] Appl. No.: 507,305

[22] Filed: Apr. 10, 1990

Related U.S. Application Data

[63] Continuation of Ser. No. 729, Jan. 6, 1987, abandoned.

[30] Foreign Application Priority Data

Jan. 8, 1986 [NZ] New Zealand ................ 214774

[51] Int. Cl.$^5$ .................. C07H 3/10; A01N 43/00
[52] U.S. Cl. ...................... 536/4.1; 536/1.1; 536/18.1; 536/119; 536/120; 71/65; 71/75; 71/76; 71/88
[58] Field of Search ............... 536/4.1, 1.1, 119, 18.1, 536/120; 71/65, 75, 76, 88

[56] References Cited

U.S. PATENT DOCUMENTS

| | | | |
|---|---|---|---|
| 3,305,554 | 2/1967 | Carlberg et al. | 536/120 |
| 3,414,560 | 12/1968 | Carlberg et al. | 536/120 |
| 3,655,884 | 4/1972 | Rossi et al. | 514/23 |
| 3,914,212 | 10/1979 | Baschang et al. | 536/1.1 |
| 3,926,947 | 12/1975 | Lipska | 536/1.1 |
| 4,146,384 | 3/1979 | Schmidt et al. | 71/88 |
| 4,177,344 | 12/1979 | Baschang et al. | 536/120 |
| 4,207,088 | 6/1980 | Konz | 71/88 |
| 4,388,104 | 6/1983 | Powell et al. | 71/88 |
| 4,429,119 | 1/1984 | Loh | 536/4.1 |
| 4,525,203 | 6/1985 | Payne et al. | 549/273 |

FOREIGN PATENT DOCUMENTS

| | | |
|---|---|---|
| 0081893 | 6/1983 | European Pat. Off. |
| 1293546 | 10/1972 | United Kingdom |
| 2120652 | 12/1983 | United Kingdom |

OTHER PUBLICATIONS

Kobayashi, et al., *Macromolecules*, 16: 710–711 (1983).
Iversen, et al., *Can. J. Chem.*, 60: 299–303 (1982).
Zemplen, et al., *Chem. Ber.* 70: 1848–1856 (1937).
Kochetkov, et al., *Tetrahedron Letters*, 22: 4315–4318 (1981).
Trinka, et al., *Collection Czechoslav. Chem. Commun.* 36: 2216–2225 (1971).
Uryu, et al., *Chem. Abstr.* 98: 72608a (1983).
Halpern, et al., *J. Org. Chem.* 38: 204–209 (1973).
Merlis, et al., *Izvestiya Akademii Nauk SSR, Seriya Khimicheskaya*, 1: 139–142 (1975).
Assarsson, et al., *Chem. Abstr.* 55: 24003c (1959).
Cerny, et al., *Chem. Abstr.* 63: 3021b (1965).
Cerny, et al., *Chem Abstr.* 68: 11489c (1968).
Seib, *Chem. Abstr.*, 70: 4533u (1969).
Cerny, et al., *Chem. Abstr.*, 72: 3668w (1970).
Pacak, et al., *Chem. Abstr.*, 77 140429m (1972).
Brimacombe, et al., *Chem. Abstr.*, 84: 17615m (1976).
Thiem, et al., *Chem. Abstr.*, 86: 106924v (1977).
Foliadov, et al., *Chem. Abstr.*, 90: 7839x (1979).
Kobayashi, et al., *Chem. Abstr.*, 92: 42273w (1979).
Cerny, et al., *Chem. Abstr.*, 93: 186699h (1980).
Kobayashi, et al., *Chem. Abstr.*, 97: 39482m (1982).
Itoh, et al., *Chem. Abstr.*, 98: 16982f (1983).
Baschang, et al., *Chem. Abstr.*, 98: 126564d (1983).
Ohrui, et al., *Chem. Abstr.*, 99: 54081q (1983).
Kobayashi, et al., *Chem. Abstr.* 99: 105603w (1983).
Uryu, et al., *Chem. Abstr.*, 101: 38746q (1984).
Kucar, et al., *Chem. Abstr.*, 102: 24932f (1985).
Schrami, et al., *Chem. Abstr.*, 103: 142281m (1985).
Elbert, et al., *Chem. Abstr.*, 104: 149273q (1986).

*Primary Examiner*—Ronald W. Griffin
*Attorney, Agent, or Firm*—Scully, Scott, Murphy & Presser

[57] ABSTRACT

Herbicidal and/or plant-growth regulatory compositions comprising, together with a carrier and/or surface-active agent, an effective amount of at least one herbicidal and/or plant growth regulatory active agent selected from compounds of formula (I)

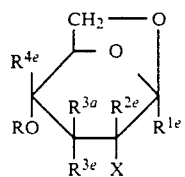

(in which
R represents an optionally substituted aralkyl group,
X represents an O—, N— or S-linked organic group, an optionally substituted hydrocarbyl group, a halogen atom, a hydroxy, amino, alkoxyamino, nitro, cyano, azido, sulpho or phospho group, or together with the group $R^{2e}$, X may represents a ketonic oxygen atom —O— or a group of formula —CH$_2$O—;
$R^{1e}$ represents a hydrogen atom or an optionally substituted hydrocarbyl group, or a formyl group;
$R^{2e}$ represents a hydrogen atom, a hydroxy group or an optionally substituted hydrocarbyl or O-linked hydrocarbyl group,
or, together with the group X, $R^{2e}$ may represent a ketonic oxygen atom —O— or a group of formula —CH$_2$O—;
$R^{3a}$ represents a hydrogen atom, a hydroxy group or an optionally substituted alkoxy, alkenyloxy, aralkoxy or $C_{1-4}$ hydrocarbyl group;
$R^{3e}$ represents a hydrogen atom, a hydroxy group or an optionally substituted hydrocarbyl or O-linked hydrocarbyl group; and
$R^{4e}$ represents a hydrogen atom or an optionally substituted hydrocarbyl group)

and enantiomers and salts thereof.

Methods for preparing the compounds of formula (I) are described; the compositions are valuable as herbicides and/or plant-growth regulants, particularly for use with crops such as soya, rape, sugar-beet, cotton, wheat, maize and rice.

22 Claims, No Drawings

1,6-ANHYDRO-β-HEXOPYRANOSE DERIVATIVES AND THEIR USE AS HERBICIDES AND PLANT GROWTH REGULATORS

This is a continuation of copending application Ser. No. 000,729, filed on Jan. 6, 1987, now abandoned.

The present invention relates to 1,6-anhydro-β-hexopyranose derivatives and their use as herbicides and plant growth regulants.

U.S. Pat. No. 4,177,344 broadly defines a class of 1,6-anhydro-β-D-hexopyranose derivatives of general formula (A)

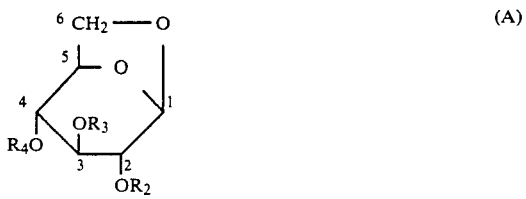

in which $R_2$ represents a hydrogen atom or a methyl or aromatic acyl group, $R_3$ represents an alkyl, alkenyl or optionally substituted aralkyl group, and $R_4$ represents a hydrogen atom or an alkyl, alkenyl or optionally substituted aralkyl group (or one of $R_3$ and $R_4$ may represent an optionally substituted aroyl group), with the provisos that (a) $R_3$ and $R_4$ together contain at least three carbon atoms, (b) if $R_4$ represents a benzyl group $R_3$ must contain at least two carbon atoms, and (c) if one of $R_3$ and $R_4$ represents an aroyl group $R_2$ must be a hydrogen atom. The compounds are stated to have fibrinolytic and thrombolytic activities in animals.

It will be noted that in general the hexopyranose ring substituents in the above Haworth projection general formula A are all axial, the typical stable conformation of the structure being the chair form (B)

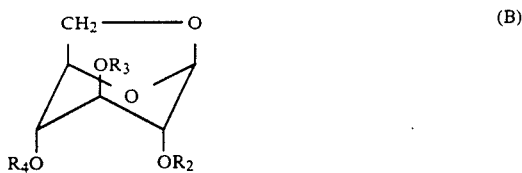

It should be noted, however, that in some circumstances the chair form may be distorted, with substituents becoming wholly or partially equatorial.

The representations herein for hexopyranose derivatives are given according to the Haworth projection. Hydrogen atoms are not indicated.

We have now unexpectedly found that, by selection of an optionally substituted aralkyl group for $R_4$ in general formula A above, compounds having biological activities, in particular herbicidal and/or plant growth regulatory activities, may be obtained.

In a first aspect, therefore, the invention provides herbicidal and/or plant growth regulatory compositions comprising, together with a carrier and/or surface-active agent, an effective amount of at least one herbicidal and/or plant growth regulatory active agent selected from compounds of formula (I)

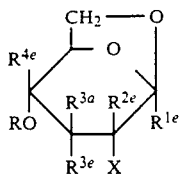

(in which
R represents an optionally substituted aralkyl group,
X represents an O-, N- or S-linked organic group, an optionally substituted hydrocarbyl group, a halogen atom, a hydroxy, amino, alkoxyamino, nitro, cyano, azido, sulpho or phospho group, or together with the group $R^{2e}$, X may represent a ketonic oxygen atom —O— or a group of formula —CH$_2$O—;
$R^{1e}$ represents a hydrogen atom or an optionally substituted hydrocarbyl group, or a formyl group;
$R^{2e}$ represents a hydrogen atom, a hydroxy group or an optionally substituted hydrocarbyl or O-linked hydrocarbyl group, or, together with the group X, $R^{2e}$ may represent a ketonic oxygen atom —O— or a group of formula —CH$_2$O—;
$R^{3a}$ represents a hydrogen atom, a hydroxy group or an optionally substituted alkoxy, alkenyloxy, aralkoxy or C$_{1-4}$ hydrocarbyl group;
$R^{3e}$ represents a hydrogen atom, a hydroxy group or an optionally substituted hydrocarbyl or O-linked hydrocarbyl group; and
$R^{4e}$ represents a hydrogen atom or an optionally substituted hydrocarbyl group)
and enantiomers and salts thereof.

The term "aralkyl group" herein refers to a carbocyclicaryl-alkyl or heterocyclicaryl-alkyl group, which may optionally be substituted in the aryl and/or alkyl portions. The aryl and alkyl portions may if desired be linked together via a heteroatom (e.g. sulphur). The alkyl chain portion may suitably contain up to 6 carbon atoms, not including carbon atoms which may be present in any substituent groups.

Thus, in a preferred form, R may be generally represented as $$Ar\text{---}(CR^aR^b)_n\text{---} \quad (II)$$

in which
n is from 1 to 6, and where n is more than 1 each adjacent repeating unit may be the same as or different from its neighbouring unit;
$R^a$ and $R^b$, which may be the same of different, are selected from hydrogen and halogen atoms and phenyl and C$_{1-6}$ alkyl (e.g. methyl groups); and
Ar represents an optionally substituted phenyl, naphthyl, anthryl, quinolyl, pyridyl, furyl, thienyl, benzimidazolyl, benzothienyl, xanthenyl, phenylthio or phenylsulphenyl group.

If desired substituents present on the aryl portion may be linked to the alkyl portion of the group R or to substituents of the alkyl portion, to form a closed ring between the aryl and alkyl portions. An example of such a group for R is the indanyl group.

There may particularly be mentioned groups of the above formula (II) in which n is 1 and Ar represents an optionally substituted phenyl group, most particularly those wherein at least one of $R^a$ and $R^b$ represents a hydrogen atom.

Thus R may be particularly represented as

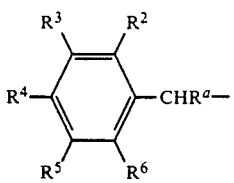 (III)

in which $R^a$ represents a hydrogen atom or a methyl group; and $R^2$ to $R^6$, which may be the same or different, are selected from hydrogen and halogen atoms, and alkyl, alkoxy, substituted alkyl (e.g. trifluoromethyl or benzyl), substituted alkoxy (e.g. benzyloxy), carbocyclicaryl (e.g. phenyl), heterocyclicaryl (e.g. methyloxadiazolyl), alkylthio, cyano, nitro, sulpho, carboxy and esterified (e.g. by methyl or ethyl) carboxy groups.

One sub-class of the group of radicals represented by formula (III) comprises those radicals in which one of the substituents $R^2$ and $R^6$ is a halogen atom or an optionally substituted alkyl group and the other substituents $R^3$, $R^4$ and $R^5$ (and the remaining $R^2$ or $R^6$ substituent) are independently selected from hydrogen, halogen and optionally substituted alkyl.

If desired adjacent $R^2/R^3$ and $R^5/R^6$ pairs of substituents may be linked to form a fused ring system, e.g. an indanyl or tetrahydronaphthyl structure where adjacent alkyl substituents are linked.

Especially preferred for R are benzyl or α-methylbenzyl groups, or groups of the above formula (III) in which $R^a$ is a hydrogen atom and one or each of $R^2$ and $R^6$ is a halogen atom or a methyl group and the others of $R^2$ to $R^6$ are hydrogen atoms or are substituted by halogen and optionally substituted alkyl.

The terms "alkyl" and "alkoxy" used herein refer preferably to $C_{1-6}$, especially $C_{1-4}$, alkyl and alkoxy groups, most preferably methyl, methoxy, ethyl, ethoxy, propyl, propoxy, isopropyl and isopropoxy, and include also such groups substituted by one or more $C_{3-6}$ cycloalkyl groups. The terms "alkenyl" and "alkenyloxy", and "alkynyl" and "alkynyloxy" used herein refer preferably to $C_{2-6}$, especially $C_{2-4}$ groups such as allyl, allyloxy, propynyl and propynyloxy groups.

The term "O-, N- and S-linked organic groups" herein refer to organic carbon-containing groups which are linked through a C—O—, C—N— and C—S— linkage respectively.

O-linked organic groups in the above definition of formula (I) include alkoxy, substituted alkoxy [e.g. substituted by an epoxy group or by one or more halogen atoms or hydroxy, alkoxy, aryl (e.g. phenyl, halophenyl, methylphenyl, trifluoromethylphenyl or methoxyphenyl), alkoxycarbonyl or aralkoxycarbonyl groups], alkenyloxy (e.g. allyloxy), alkynyloxy (e.g. prop-2-ynyloxy) and acyloxy (e.g. acetoxy) groups.

N-linked organic groups in the above definition of formula I include mono- or di-alkylamino, mono- or di-aralkylamino, trialkylammonium, carboxamido [e.g. acetamido and 1-alkyl-3-arylureido (e.g. 1-methyl-3-phenyl- or 1-methyl-3-(3,4-dichlorophenyl)-ureido)], dicarboximido (e.g. phthalimido) and N-azole (e.g. N-pyrazolyl, N-triazolyl or N-imidazolyl) groups.

S-linked organic groups in the above definition of formula I include alkylthio, alkylsulphinyl and alkylsulphonyl groups and substituted derivatives thereof (e.g. aralkylthio groups such as the benzylthio group).

The term "hydrocarbyl group" herein refers to a saturated or wholly or partially unsaturated group containing only carbon and hydrogen atoms. Examples of such groups which may be mentioned include alkyl (e.g. methyl), alkenyl, alkynyl groups (particularly those containing up to 6, especially up to 4, carbon atoms) and carbocyclicaryl and carbocyclicaryl-alkyl groups (particularly the phenyl and phenyl-$C_{1-4}$-alkyl groups).

Hydrocarbyl groups may for example be substituted by one or more hydroxy, alkoxy (e.g. methoxy), cyano or alkylthio groups or halogen atoms.

The term "halogen atom" or "halo" herein includes fluorine, chlorine, bromine and iodine atoms.

In particular the following groups may be mentioned:

1. for R, a benzyl or α-methylbenzyl group, or a group of formula (IV)

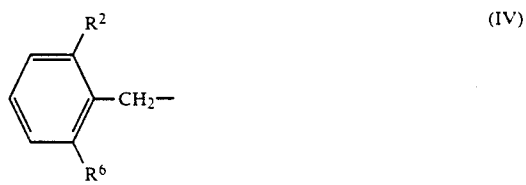 (IV)

in which $R^2$ and $R^6$ are independently selected from a halogen atom and methyl groups, or $R^2$ represents a halogen atom or a methyl group and $R^6$ represents a hydrogen atom.

2. for X, a halogen atom, or a hydroxy, $C_{1-3}$ alkoxy, $C_{2-3}$ alkenyloxy, aralkoxy, alkythio, $C_{1-3}$ alkyl, methoxy-$C_{1-3}$-alkyl or azido group;

3. for $R^{1e}$ a hydrogen atom or a $C_{1-4}$ alkyl group;

4. for $R^{2e}$ a hydrogen atom;

5. for $R^{3a}$ and $R^{3e}$, a hydrogen atom or a hydroxy, $C_{1-4}$ alkoxy or ar-$C_{1-4}$-alkoxy group;

6. for $R^{4e}$, a hydrogen atom or a $C_{1-4}$ alkyl group; and most particularly a hydrogen atom.

As mentioned above, the invention also includes within its scope compositions containing enantiomers and/or salts of the compounds of formula (I). The salts may for example be addition salts formed with a suitable acidic or basic group of the compound of formula (I), or for example an alkali metal (e.g. sodium) salt of a compound in which X represents a sulpho or phospho group.

The compounds of formula (I) are capable of optical isomerism. The invention includes within its scope enantiomers of compounds of formula (I) and salts thereof. The invention also includes within its scope all possible isomer mixtures in which the predominating isomer is that having the structure indicated by formula (I) or an enantiomer thereof.

In a further aspect, the invention provides a method for preparing compositions as described above, which method comprises admixing a suitable amount of at least one compound of formula (I) as defined above or a salt or enantiomer thereof with a carrier and/or surface-active agent.

In a still further aspect, the invention provides compounds of formula (I) as defined above and enantiomers and salts thereof for use as herbicides and/or plant growth regulants.

Suitable solid carriers are natural and synthetic clays and silicates, for example natural silicas, magnesium silicates, calcium carbonates, magnesium aluminium silicates, aluminium silicates, calcium sulphate, waxes, bitumens, synthetic silicon oxides and calcium or aluminium silicates, polymers such as polyvinyl chloride and styrene polymers or solid fertilisers, for example superphosphates. Suitable solid diluents include for example kaolin, bentomite, kieselguhr, dolomite, calcium carbonate, talc, powdered magnesia, and Fuller's earth.

Examples of suitable fluid carriers are water, alcohols, glycols, ketones, ethers, aromatic hydrocarbons such as benzene, toluene and xylene; petroleum fractions, chlorinated hydrocarbons, including liquefied gases.

The surface-active agent may be an ionic (e.g. cationic or anionic) or non-ionic emulsifying, dispersing or wetting agent. Any of the surface-active agents usually applied in formulating herbicides or pesticides may be used. Examples of suitable surface-active agents are quaternary ammonium compounds such as cetyltrimethylammonium bromide; soaps; salts of aliphatic monoesters of sulphuric acid, e.g. sodium lauryl sulphate; the sodium or calcium salts of polyacrylic acids and lignin sulphonic acids; the condensation product of fatty acids or aliphatic amines or amides containing at least 12 carbon atoms with ethylene or propylene oxide; fatty acid esters of glycerol, sorbitan, sucrose or pentaerythritol; condensation products of fatty alcohols or alkyl phenols with ethylene oxide; alkali or alkaline earth metal salts, preferably sodium salts, of sulphuric or sulphonic acid esters containing at least 10 carbon atoms; and polymers of ethylene oxide and copolymers of ethylene oxide and propylene oxide. Other nonionic agents are the partial esters derived from long chain fatty acids and hexitol anhydrides, for example sorbitol monolaurate; the condensation products of the said partial esters with ethylene oxide and the lecithins.

The compositions of the invention may for example be formulated as wettable powders, dusts, granules, solutions, emulsifiable concentrates, emulsions, suspension concentrates and aerosols.

The composition may for example contain up to 99% by weight of the herbicidal and/or plant growth regulatory active agent. If desired, stabiliser(s) and/or additives such as defoamers, corrosion inhibitors, penetrants or stickers may be present.

The composition of the invention may contain other ingredients, for example, protective colloids such as gelatin, glue, casein, gums, cellulose ethers, and polyvinyl alcohol; and thixotropic agents e.g. bentonites, sodium polyphosphates. Suitable stabilisers include ethylenediaminetetra-acetic acid, urea, and triphenyl phosphate. As stickers there may be used, for example, non-volatile oils.

The compounds of the invention may be used in admixture with other herbicides and pesticides. In particular they may be mixed with active materials such as:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenyl)propionic acid (dichloroprop), 2,4,5-trichlorophenoxyacetic acid (2,4,5-T), 4-(4-chloro-2-methoxyphenoxy)butyric acid (MCPB), 2,4-dichloro-phenoxyacetic acid (2,4-D), 4-(2,4-dichlorophenoxy)butyric acid (2,4-DB), 2-(4-chloro-2-methylphenoxy)-propionic acid (mecoprop), and their derivatives (e.g. salts, esters and amides);

C. 3-[4-(4-halophenoxy)phenyl]-1,1-dialkylureas such as 3-[4-(4-chlorophenoxy)phenyl]-1,1-dimethylurea.

D. Dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);

F. phenylurea herbicides such as N'-(3,4-dichlorophenyl)-N,N-dimethylurea (diuron) and N,N-dimethyl-N'-[3-(trifluoromethyl)phenyl]urea (flumeturon);

G. phenylcarbamoyloxyphenylcarbamates such as 3-[methoxy carbonylamino]phenyl (3-methylphenyl)-carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyl-uracil (bromacil) and 3-t-butyl-5-chloro-6-methyluracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron), 3-(4-bromo-4-chlorophenyl)-1-methoxy-1-methylurea (chlorobromuron).

L. thiolcarbamate herbicides such as S-propyl dipropylthiocarbamate (vernolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl-chloro-2',6'-diethylacetanilide (butachlor), the corresponding N-methoxy compound (alachlor), the corresponding N-i-propyl compound (propachlor), 3',4'-dichloropropionanilide (propanil) and 2-chloro-N-[pyrazol-1-ylmethyl]acet-2'-6'-xylidide (metazachlor);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid (acifluorfen) and salts and esters thereof, 2-chloro-4-trifluoromethylphenyl 3-ethoxy-4-nitrophenyl ether (oxyfluorfen) and 5-(2-chloro-4-(trifluoromethyl)phenoxy)-N-(methylsulfonyl)-2-nitrobenzamide (fomesafen), 5-(2-chloro-6-fluoro-4-(trifluoromethyl)phenoxy)-N-(ethylsulphonyl)-2-nitrobenzamide (halosafen); and S. phenoxyphenoxypropionate herbicides such as 2-(4-(4'-trifluoromethylphenoxy)-phenoxy)-propionic acid methylester (trifop-methyl), 2-(4-((5-trifluoromethyl)-2-(pyridinyl)oxy)phenoxypropanoic acid (fluazifop) and esters thereof, 2-(4-((3-chloro-5-trifluoromethyl)-2-pyridinyl)oxy)phenoxy)propanoic acid (haloxyfop) and esters thereof, 2-(4-((6-chloro-2-quinoxalinyl)oxy)phenoxypropanoic acid (xylofop) and esters thereof; and T. cyclohexanedione herbicides such as 2,2-dimethyl-4,6-dioxo-5-(1-((2-propenyloxy)amino)-butylidine) cyclohexane carboxylic acid (alloxydim) and salts thereof, 2-(1-ethoxyimino)butyl-5-(2-(ethylthio)-propyl)-3-hydroxy-2-cyclohexen-1-one (sethoxydim), 2-(1-(3-chloroallyloxyimino)butyl)-5-(2-ethylthio-propyl)-3-hydroxy cyclohex-2-enone (cloproxydim), 2-(1-ethoxyimino)butyl)-3-hydroxy-5-thian-3-yl cyclohex-2-enone (cycloxydim); and U. sulfonyl urea herbicides such as 2-chloro-N-(4-methoxy-6-methyl-1,3,5-triazin-2-yl)-aminocarbonyl) benzenesulphonamide (chlorosulfuron), methyl 2-((((4,6-dimethyl-2-pyrimidinyl)amino)carbonyl-)amino)sulphonylbenzoic acid (sulfometuron), 2-(((3-(4-methoxy-6-methyl-1,3,5-triazin-2-yl)carbonyl-)amino)sulphonyl)benzoic acid (metsulfuron) and esters thereof;

V. imidazolidinone herbicides such as 2-(4,5-dihydro-4-isopropyl-4-methyl-5-oxoimidazol-2-yl)quinoline-3-carboxylic acid (imazaquin), methyl 6-(4-isopropyl-4-methyl-5-oxo-2-imidazolin-2-yl)-m-toluate and p-toluate isomer (AC 222293)

W. arylanilide herbicides such as 1-methylethyl-N-benzoyl-N-(3-chloro-4-fluorophenyl)-L-alanine(flamprop-isopropyl), ethyl N-benzoyl-N-(3,4-dichlorophenyl)-DL-alaninate (benzoylprop-ethyl), N-(2,4-difluorophenyl)-2-(3-(trifluoromethyl)phenoxy)-3-pyridinecarboxamide (diflufenican); and X. amino acid herbicides such as N-(phosphonomethyl)glycine (glyphosate) and DL-homoalanin-4-yl(methyl)phosphinic acid (phosphinothricin) and their salts and esters; and Y. organoarsenical herbicides such as monosodium methanearsonate (MSMA); and Z. miscellaneous herbicides including N,N-dimethyldiphenylacetamide (diphenamid), N-(1-naphthyl)-phthalamic acid (naptalam) and 3-amino-1,2,4-triazole, 2-ethoxy-2,3-dihydro-3,3-dimethylbenzofuran methanesulfonate (ethofumesate), 1,4-epoxy-p-meth-2-yl 2-methylbenzyl ether (cinmethylin), 2-(2-chlorophenyl)methyl-4,4-dimethyl-3-isoxazolidinone (dimethazone);

AA. Examples of useful contact herbicides include: bipyridylium herbicides such as those in which the active entity is the 1,1'-dimethyl-4,4'-dipyridylium ion (paraquat) and those in which the active entity is the 1,1')ethylene-2,2'-dipyridylium ion (diquat);

The complementary herbicide is suitably present in the mixture or composition in an amount such that it is applied at its conventional rate.

The amount of active compound(s) used can vary within a fairly wide range. It depends essentially on the nature of the desired effect. In general, the amounts used are from 0.01 to 10 kg of active compound per ha, preferably from 0.1 to 5 kg/ha.

The compositions of the invention can be applied either before or after the emergence of the plants. They can also be worked into the soil before sowing.

In addition to their application as herbicides and/or plant growth regulators, certain of the compounds of formula (I) and their enantiomers and salts are valuable as starting materials for the preparation of other active compounds of formula (I) and their enantiomers and salts.

The compounds of formula (I) and the enantiomers and salts thereof may, for example, be prepared by the following processes:

A. cyclising a compound of formula (Va) or (Vb)

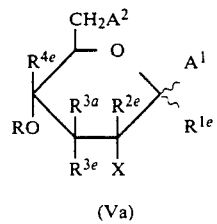 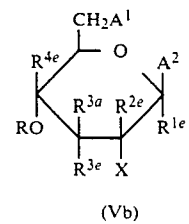

(Va)  (Vb)

(in which

R, X, $R^{1e}$, $R^{2e}$, $R^{3a}$, $R^{3e}$ and $R^{4e}$ are as defined above, or represent protected forms thereof, $A^2$ is an O-linked group capable of being partially split off to leave a negative oxide anion, and $A^1$ is a group capable of being completely split off to leave a positive carbonium cation)

or an enantiomer thereof, and optionally subsequently splitting off or converting any protective groups present to produce the desired compounds.

The term "protected form thereof" used throughout this specification includes the use of temporary deactivating substituents and the use of different substituents which are precursors for the desired group. For example, in this process A a protected form of OR may be a hydroxy group which is inactive to the reaction conditions but readily replaceable by 4-aralkylation.

O-linked groups for $A^2$ capable of being partially split off to leave a negative oxide anion include hydroxy groups, activated hydroxy, e.g. benzyloxy, trityloxy, diphenylmethoxy, t.-butyldiphenysilyloxy or trimethylsilyloxy groups or acyloxy, e.g. acetoxy or benzoyloxy, groups.

Groups for $A^1$ capable of being completely split off to leave a positive carbonium cation include halogen atoms, alkoxy groups (e.g. methoxy), hydroxy groups or hydroxy groups esterified by strong organic acids such as benzenesulphonic acid, methanesulphonic acid or p-toluenesulphonic acid.

The cyclisation reaction is conveniently carried out in the presence of an acid or base, for example an acid resin, a Lewis acid, a strong mineral acid or an organic or inorganic base. Suitable acids include for example hydrogen halide acids. Suitable bases include for example alkali or alkaline earth metal hydroxides, carbonates or bicarbonates.

The reaction is suitably carried out in a solvent. Solvents may for example be chosen, depending on the reactants and conditions employed, from halogenated hydrocarbons, aromatic hydrocarbons such as toluene or xylene, alcohols, ethers or ketones such as acetone, in the presence or absence of water.

The cyclisation may be effected at room temperature or at elevated temperatures.

Compounds of formula (Va) and (Vb), where not known in the art, may be prepared by methods analogous to those known in the art.

For example, compounds of formula (Va) and (Vb) wherein $A^2$ represents an activated hydroxy group may be prepared from the corresponding compound of formula (Va) and (Vb) wherein $A^2$ represents a hydroxy group by conventional methods. Compounds of formula (Va) wherein the groups OR and $A^2$ represent hydroxy groups may conveniently be prepared by acid cleavage of a corresponding compound containing the partial structure (Vc)

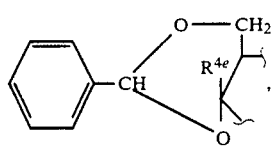

which compounds are known in the literature or may readily be derived therefrom (see e.g. Carbohydr. Res. 1980, 86, 158–160).

Compounds of formula (Va) and (Vb) wherein OR represents a hydroxy group, $A^2$ represents an activated hydroxy group and $R^{4e}$ represents an optionally substituted hydrocarbyl group may for example be prepared by a Grignard reaction on a compound of formula (Vd) or (Ve)

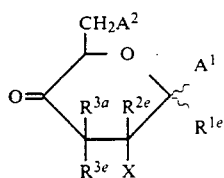

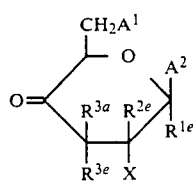

(wherein
$A^1$ represents a group capable of being completely split off to leave a positive carbonium ion,
$A^2$ represents an activated hydroxy group, and
X, $R^{1e}$, $R^{2e}$, $R^{3a}$ and $R^{3e}$ are as defined above or represent protected forms thereof)
using a Grignard reagent of formula R"MgHal (wherein R" is an optionally substituted hydrocarbyl group or a protected form thereof and Hal is a halogen atom),
and optionally splitting off or converting any protective groups present.

The Grignard reaction normally results in a mixture of the C-4 epimers, which may conveniently be resolved into the desired compound of formula (Va) or (Vb) either before or after the cyclisation.

Compounds of formula (Vd) and (Ve) may conveniently be prepared by oxidising a corresponding 4-hydroxy compound, for example using a Swern oxidation with dimethyl sulphoxide/oxalyl chloride as the oxidising agent (see A J Mancuso and D Swern, Synthesis, 1981, 179).

B. Aralkylating a compound of formula (VI)

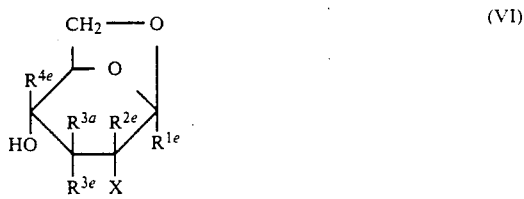

or a corresponding alkali metal alkoxide,
(in which X, $R^{1e}$, $R^{2e}$, $R^{3a}$, $R^{3e}$ and $R^{4e}$ are as defined above, or represent protected forms thereof),
or an enantiomer thereof,
and optionally subsequently splitting off or converting any protective groups present, to produce the desired compound.

The aralkylation reaction may conveniently be carried out using an aralkyl halide (e.g. a bromide or chloride). The reaction may be carried out in an organic solvent such as tetrahydrofuran, dimethylsulphoxide or dimethylformamide.

The reaction may be performed in the presence of a base such as, for example, barium oxide, potassium hydroxide or silver oxide. A quaternary ammonium salt catalyst such as tetrabutylammonium bromide or iodide may be employed, under suitable conditions as reported by Czernecki et al (Tetrahedron Lett, (1976) 3535-6).

Compounds of formula (VI), where not known in the art, may be prepared by methods analagous to those known in the art, or may be prepared from an analagous compound of formula (I) wherein R is a benzyl group by debenzylation, for example by catalytic hydrogenation.

Enantiomers of compounds of formula (VI) wherein X represents an O-linked organic group and $R^{1e}$, $R^{2e}$, $R^{3a}$, $R^{3e}$ and $R^{4e}$ represent hydrogen atoms may be prepared by reaction of a suitably protected form of 1,6-anhydro-2,3-0benzylidene-$\beta$-L-allopyranose

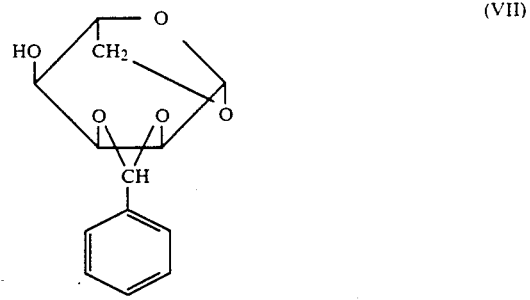

with for example N-bromosuccinimide, and subsequently debrominating the compound of formula (VIII)

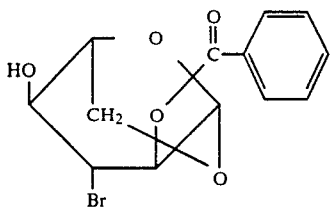

(VIII)

formed and optionally replacing the 2-O-substitutent, by conventional methods. The compound of formula (VII) may be readily prepared from L-gulose (Methods Carbohydr. Chem. (1963) 2 65) by heating with water in the presence of a strong acid resin to form 1,6-anhydro-β-L-gulopyranose, which is then reacted with benzaldehyde dimethyl acetal under acidic conditions, and the remaining free 4-hydroxyl group is inverted via oxidation to a ketone intermediate and subsequent reduction.

Alkali metal alkoxides corresponding to compounds of formula (VI) may be prepared by conventional methods such as reaction of an alcohol of formula (VI) with an alkali metal hydride (e.g. sodium hydride) in a suitable solvent.

C. for the preparation of compounds wherein X represents an O-linked organic group and/or wherein $R^{3a}$ represents an optionally substituted alkoxy, alkenyloxy or aralkoxy group and/or where $R^{2e}$ and/or $R^{3e}$ represents an optionally substituted O-linked hydrocarbyl group:

reacting a corresponding compound of formula (I) wherein X and/or $R^{3a}$ and/or $R^{2e}$ and/or $R^{3e}$ represents a hydroxy group, and the remainder of X, R, $R^{1e}$, $R^{2e}$, $R^{3a}$, $R^{3e}$ and $R^{4e}$ are as defined above or represent protected forms thereof, or an enantiomer thereof, or a corresponding alkali metal alkoxide thereof, with a compound serving to introduce respectively an O-linked organic group at X, an optionally substituted alkoxy, alkenyloxy or aralkoxy group at $R^{3a}$, or an optionally substituted O-linked hydrocarbyl group at $R^{2e}$ or $R^{3e}$, and optionally subsequently splitting off or converting any protective groups present, to produce the desired compound.

Reagents serving to introduce the O-linked groups at X, $R^{3a}$, $R^{2e}$ and/or $R^{3e}$ include, for example, organic halides (e.g. alkyl or aralkyl halides such as methyl iodide, benzyl bromide or ethyl iodide). Where an organic halide reagent is used, the reaction may be carried out under conditions analogous to those described for reaction B above.

The compound of formula (I) used as starting material may for example be prepared by methods D, G, H or N.

D. for the preparation of compounds wherein X represents a hydroxy group:

reducing a compound of formula (I) wherein X together with the group $R^{2e}$ represents a ketonic oxygen atom, and R, $R^{1e}$, $R^{3a}$, $R^{3e}$ and $R^{4e}$ are as defined above or represent protected forms thereof, or an enantiomer thereof, and optionally subsequently splitting off or converting any protective groups present, to produce the desired compound.

Reducing agents which may conveniently be employed include hydride reducing agents such as lithium aluminium hydride or sodium borohydride. The reduction product may be contaminated with the D-arabino isomer, in which case they may be separated by conventional techniques such as fractional crystallisation or chromatography. The D-ribo form is found to be generally the less polar.

By selecting suitable reaction conditions the yield of the desired D-ribo isomer may be maximised.

The reaction may suitably be carried in an aqueous or nonaqueous solvent, e.g. an alcohol, an alcohol/water mixture, or in water; the choice of solvent depends on the reactants present, so that for example when lithium aluminium hydride is used as reducing agent, the solvent will be non-aqueous.

E. for the preparation of compounds wherein X together with the group $R^{2e}$ represents a ketonic oxygen atom and the groups $R^{1e}$, $R^{3a}$, $R^{3e}$ and $R^{4e}$ all represent hydrogen atoms;

reaction of levoglucosenone (IX)

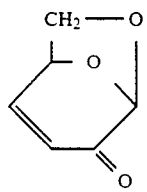

(IX)

with an alcohol of formula (X)

ROH        (X)

wherein R is as defined above for formula (I).

The reaction is a Michael addition reaction which may conveniently be carried out in conventional manner in the presence of an acid or base catalyst. Suitable acidic catalysts include protic acids (e.g. sulphuric, hydrochloric, p-toluenesulphonic, trifluoromethanesulphonic and preferably trifluoroacetic acids) or Lewis acids (e.g. $BF_3 \cdot (C_2H_5)_2O$). Suitable basic catalysts include alkali metal alkoxides prepared from alkali metals or hydrides (e.g. from sodium metal, sodium hydride or potassium hydride) by reaction with an alcohol, tertiary amines (e.g. triethylamine) or solid bases (e.g. alumina).

Where a basic catalyst is employed, the alcohol of formula (X) may first be diluted with water to increase the reaction rate, as reported by Shafizadeh et al (Carbohydr. Res. (1979) 71, 169–191).

The reaction conditions may be controlled to minimise unwanted side reactions, although some side reactions may, if desired, be encouraged. For example, under basic conditions the levoglucosenone starting material or its derivatives may undergo base-catalysed oligomerisation.

Under acidic conditions the product may rapidly react further with the alcohol of formula (X) to form a corresponding ketal of formula (I) wherein X and $R^{2e}$ each represent an optionally substituted aralkoxy group. The reaction may if desired be allowed to proceed to this stage, or may be partially controlled to lead to a mixture of said ketal product and alcohols wherein X or $R^{2e}$ is a hydroxy group. Such control may suitably be effected by the addition of a reducing agent such as sodium borohydride to the reaction mixture while the 2-keto product predominates, so promoting the reduction reaction D above in preference to the ketal formation. In practice a mixture of the D-ribo and ketal compounds of formula (I) and the contaminating D-arabino form may result.

In a further alternative, the compound of formula (I) initially formed, wherein X together with the group R$^{2e}$ represents a ketonic oxygen atom and the groups R$^{1e}$, R$^{2e}$, R$^{3a}$, R$^{3e}$ and R$^{4e}$ all represent hydrogen atoms, may be isolated and subsequently reacted under acidic conditions with a different alcohol, of formula (XI)

R"OH            (XI)

wherein R" represents an optionally substituted hydrocarbyl group,
to give a different ketal of formula (I) wherein X and R$^{2e}$, which are the same, each represents an optionally substituted O-linked hydrocarbyl group and the groups R$^{1e}$, R$^{3a}$, R$^{3e}$ and R$^{4e}$ all represent hydrogen atoms.

The 2-keto compound formed in the principal reaction may, if desired, be subsequently treated with a Grignard reagent to introduce a hydrocarbyl group at the 2-position. Normally a mixture of corresponding D-ribo and D-arabino isomers will be formed, which may be separated by chromatography in view of the general difference in polarity of the two forms. For example, methyl magnesium bromide may be used as a reagent under standard Grignard conditions to produce a mixture of compounds of formula (I) in which X is a hydroxy group and R$^{2e}$ is a methyl group, and in which X is a methyl group and R$^{2e}$ is a hydroxy group.

Levoglucosenone may be obtained by known techniques, for example, acid-catalysed pyrolysis of cellulosic materials (see for example, Halpern et al. J. Org. Chem. (1973) 38 204–209, or U.S. Pat. No. 3,926,947).

F. for the preparation of compounds wherein R is a defined above, R$^{1e}$, R$^{2e}$, R$^{3a}$, R$^{3e}$ and R$^{4e}$ all represent hydrogen atoms and X is as defined above with the exception of the ketonic oxygen atom and the group —CH$_2$O— with R$^{2e}$:
reacting a compound of formula (XII)

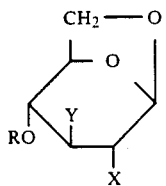

(in which R is as defined above for formula (I) or represents a protected form thereof,
Y represents a S-methyldithiocarbonate or phenylthionocarbonate group, and X is as defined above for formula (I) with the exception of the ketonic oxygen atom and the group —CH$_2$O— with R$^{2e}$, or represents a protected form thereof),
or an enantiomer thereof,
with trialkyltin hydride (e.g. tributyltin hydride)
and optionally subsequently splitting off or converting any protective groups present to produce the desired compounds.

The reaction may conveniently be carried out under reflux in an organic solvent such as toluene, and can be catalysed by a radical initiator or by radiation.

The compound of formula (XII) may for example be prepared from a compound of formula (I) wherein R is as defined above, R$^{1e}$, R$^{2e}$, R$^{3e}$ and R$^{4e}$ all represent hydrogen atoms, R$^{3a}$ represents a hydroxy group and X is as defined above for formula (I) with the exception of the ketonic oxygen atom and the group —CH$_2$O— with R$^{2e}$, using known methods described for example in J. Am. Chem. Soc. (1983) 105 4059–4065. Such a compound of formula (I) may for example, be prepared as described in reaction H, G or J below.

G. for the preparation of compounds wherein R is as defined above, R$^{1e}$, R$^{2e}$, R$^{3e}$ and R$^{4e}$ all represent hydrogen atoms, R$^{3a}$ represents a hydroxy group and X, which is the same as the group OR, represents an optionally substituted aralkoxy group:
2,4-di-O-aralkylating levoglucosan (XIII)

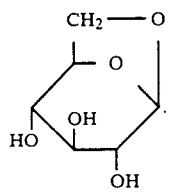

Suitable diaralkylating conditions are reported in Can. J. Chem. (1982) 60, 299–303, in which the synthesis of the 2,4-di-O-benzyl compound in 95% yield is also reported. Thus, for example, the reaction may be effected in the presence of a base such as barium oxide, using benzyl bromide as the aralkylating agent, in a solvent such as dimethylformamide.

H. for the preparation of compounds wherein R, R$^{1e}$ and R$^{4e}$ are as defined above, R$^{2e}$ and R$^{3e}$ all represent hydrogen atoms, R$^{3a}$ represents a hydroxy group and X represents an O-linked organic group, an optionally substituted hydrocarbyl group, a halogen atom, or a hydroxy, amino, cyano or azido group;
reacting a D-manno-epoxide of formula (XIV)

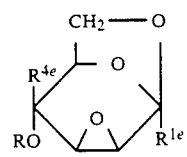

wherein R, R$^{1e}$ and R$^{4e}$ are as defined above for formula (I) or represent protected forms thereof,
or an enantiomer thereof,
with a compound serving to selectively introduce the group X as defined above at the 2-position, and optionally subsequently splitting off or converting any protective groups present to produce the desired compound.

Where X represents an O-linked organic group, the compound serving to introduce said group at the 2-position will preferably be an organic alcohol, e.g. methanol.

Where X represents an optionally substituted hydrocarbyl group, the compound serving to introduce said group at the 2-position will preferably be an organometallic derivative of said hydrocarbyl group. Regioselectivity may be achieved by the use of particular known reaction conditions (see, for example, Tetrahedron Lett. (1981) 22 4315–8 or Tetrahedron Lett. (1983) 24 5823–6).

Where X represents a halogen atom, the compound serving to introduce said group at the 2-position will preferably be a halide salt, e.g. potassium bifluoride, tetrabutylammonium bromide, diethylaluminium chloride or magnesium iodide. Regioselectivity may be achieved by the use of particular known reaction conditions (see, for example, J. Chem. Soc. Chem. Commun (1969) 77).

Where X represents a hydroxy group, the compound serving to introduce said group at the 2-position will preferably be a strong base resin or an alkali metal hydroxide, e.g. sodium hydroxide or potassium hydroxide. Regioselectivity may be achieved by the use of particular known reaction conditions (see, for example, J. Chem. Soc. C. (1971) 3143–3155).

Where X represents an amino group, the compound serving to introduce said group at the 2-position will preferably be aqueous ammonia. Regioselectivity may be achieved by the use of particular known reaction conditions (see, for example, Carbohydr.Res. (1973) 29 99–111).

Where X represents a cyano group, the compound serving to introduce said group at the 2-position will preferably be a cyanide compound. Organo-metallic cyanide salts such as diethylaluminium cyanide have been found particularly suitable.

Where X represents an azido group, the compound serving to introduce said group at the 2-position will preferably be sodium or tetraalkylammonium azide. Regioselectivity may be achieved by the use of particular known reaction conditions (see, for example, Tetrahedron Lett. (1975) 1493–4).

The reaction generally may conveniently be carried out in a solvent such as, for example, dry tetrahydrofuran, methanol, ethanol, dioxane, ethylene glycol, water and their mixtures. Where an organic alcohol is used as reagent, however, this may be present in excess to provide the solvent in addition to the reagent.

The D-manno-epoxide of formula (XIV) may be prepared by ring-closure of a tosylate compound of formula (XV)

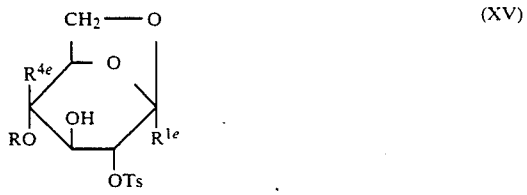

as described in the literature, e.g. Collect. Czech. Chem. Commun. (1971) 36 2216–2225.

I. for the preparation of compounds wherein $R^{2e}$ represents a hydrogen atom and X represents an S-linked organic group or an azido group;

reacting a compound of formula (XVI)

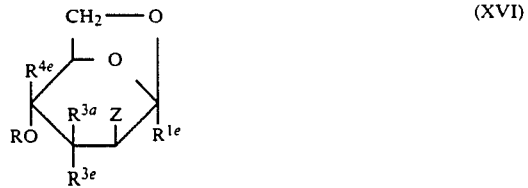

wherein R, $R^{1e}$, $R^{3a}$, $R^{3e}$ and $R^{4e}$ are as defined above or represent protected forms thereof, and Z represents a nucleophilically exchangeable group (e.g. an organic sulphonyloxy group such as a methanesulphonyloxy, p-toluenesulphonyloxy, trifluoromethanesulphonyloxy or (N-imidazole)sulphonyloxy group)

with an organic thiol of formula (XVII)

R'SH          (XVII)

(wherein R' represents an organic group), or a reactive derivative thereof, or with sodium azide, and optionally subsequently splitting off or converting any protective groups present, to produce the desired compound.

Suitable reactive derivatives of the compound of formula (XVII) include, for example alkali metal thioalkoxides (e.g. lithium thioalkoxide).

The reaction may conveniently be carried out in an organic solvent such as dimethylsulphoxide or dimethylformamide. The reaction temperature will typically depend on the nature of the starting material. For example, where Z represents a trifluoromethanesulphonyloxy group the reaction may suitably be carried out at or below about room temperature; where Z represents a p-toluenesulphonyloxy group the reaction may be carried out at an elevated temperature (e.g. around 150° C.). Compounds of formula (XVI) may be prepared by conventional methods from the corresponding alcohols by reaction with the appropriate sulphonyl anhydride or chloride.

J. for the preparation of compounds wherein X represents a mono- or di-alkylamino, mono- or di-aralkylamino, trialkylamonium, carboxamido group or dicarboximido and R, $R^{1e}$, $R^{2e}$, $R^{3a}$, $R^{3e}$ and $R^{4e}$ are as defined above:

reacting a compound of formula (I), wherein X represents an amino group and R, $R^{1e}$, $R^{2e}$, $R^{3e}$ and $R^{4e}$ are as defined above or represent protected forms thereof, with a compound capable of converting said amino group to a mono- or di-alkylamino, mono- or di-aralkylamino, trialkylammonium, carboxamido or dicarboximido group, and optionally subsequently splitting off or converting any protective groups present to produce the desired compound.

Where the group to be formed is a carboxamido or dicarboximido group, the reaction may suitably be carried out using an acyl anhydride or, where not too reactive, an acyl halide, under conventional acylating conditions. For example, to form an acetamido or trifluoroacetamido group, acetic anhydride or trifluoroacetic anhydride in a suitable solvent such as methanol or pyridine may be employed.

Compounds of formula (I) wherein X represents an amino group and R, $R^{1e}$, $R^{2e}$, $R^{3e}$ and $R^{4e}$ are as defined above, used as starting materials in the above reaction may be prepared according to processes H or L, for example, either by separate previous reaction or in situ in the reaction mixture.

K. for the preparation of compounds wherein X represents a carboxamido or dicarboximido group and R, $R^{1e}$, $R^{2e}$, $R^{3a}$, $R^{3e}$ and $R^{4e}$ are as defined above:

reacting a compound of formula (I) wherein X represents an azido group and R, $R^{1e}$, $R^{2e}$, $R^{3a}$, $R^{3e}$ and $R^{4e}$ are as defined above or represent protected forms thereof, or an activated derivative thereof, with an anhydride reagent corresponding to the desired carboxamido or dicarboximido group, and optionally subsequently splitting off or converting any protective groups present to produce the desired compound.

Azide-activating agents which may be employed include for example triphenylphosphine/tetrabutylammonium cyanide (see Tet. Lett. 25, 1984, p. 4841).

To form a phthalimido group, for example, phthalic anhydride may be used in a benzene solvent, the reaction being carried out at elevated temperature.

The azide starting material may conveniently be obtained using reaction H or I above.

L. for the preparation of compounds wherein X represents an amino group and R, $R^{1e}$, $R^{2e}$, $R^{3a}$, $R^{3e}$ and $R^{4e}$ are as defined above:

reducing a corresponding azido compound of formula (I) wherein X represents an azido group, and R, $R^{1e}$, $R^{2e}$, $R^{3a}$, $R^{3e}$ and $R^{4e}$ are as defined above or represent protected forms thereof, and optionally subsequently splitting off or converting any protective groups present to produce the desired compound.

The reduction may conveniently be carried out using lithium aluminium hydride in an organic solvent such as diethyl ether.

The azido compound of formula (I) used as starting material may be prepared for example using process H or I above.

M. for the preparation of compounds wherein X together with the group $R^{2e}$ represents a group of formula —CH$_2$O— and R, $R^{1e}$, $R^{3a}$, $R^{3e}$ and $R^{4e}$ are as defined above:

reacting a corresponding compound of formula (I) wherein X together with a group $R^{2e}$ represents a ketonic oxygen atom and R, $R^{1e}$, $R^{3a}$, $R^{3e}$ and $R^{4e}$ are as defined above or represent protected forms thereof,
  with diazomethane, and optionally subsequently splitting off or converting any protective groups present to produce the desired compound.

The reaction conditions are typically such that the D-arabino derivative predominates in the product, and may be isolated by chromatography.

N. for the preparation of compounds wherein $R^{3a}$ is a hydrogen atom and $R^{3e}$ represents a hydroxy group, and X, R, $R^{1e}$, $R^{2e}$ and $R^{4e}$ are as defined above:

reducing a compound of formula (XVIII)

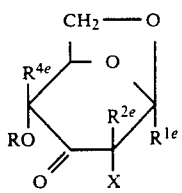

(XVIII)

(wherein X, R, $R^{1e}$, $R^{2e}$ and $R^{4e}$ are as defined above or represent protected forms thereof)

with a reducing agent capable of selectively forming the β-D-allopyranose reduction product, and optionally subsequently splitting off or converting any protective groups to produce the desired compound.

As reducing agent sodium borohydride may be particularly mentioned. The reaction may conveniently be carried out in an alcoholic solvent at reduced temperature.

The compound of formula (XVIII) used as starting material may conveniently be prepared by oxidising the corresponding β-D-glucopyranose (i.e. wherein $R^{3a}$ is a hydroxy group and $R^{3e}$ is a hydrogen atom), for example using pyridinium dichromate as an oxidant. The β-D-glucopyranose of formula (I) may be obtained, for example, using reactions G or H above.

O. for the preparation of compounds wherein $R^{1e}$ represents an optionally substituted hydrocarbyl group and X, R, $R^{2e}$, $R^{3a}$, $R^{3e}$ and $R^{4e}$ are as defined above:

ring-closing a vic-dihydroxy-protected form of a compound of formula (XIX)

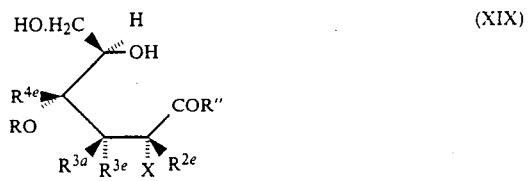

(wherein X, R, $R^{2e}$, $R^{3a}$, $R^{3e}$ and $R^{4e}$ as defined above or represent protected forms thereof; and R" represents an optionally substituted hydrocarbyl group)

and optionally subsequently splitting off or converting any protective groups present to produce the desired compound.

It will be appreciated that the stereochemistry of the starting compound of formula (XIX) is important. This compound may for example be prepared by cleavage of a tetrahydropyran derivative of formula (XX)

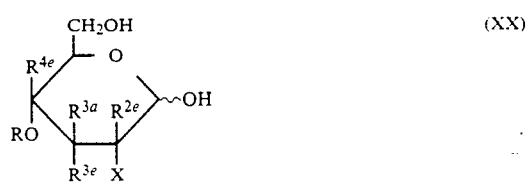

(wherein X, R, $R^{2e}$, $R^{3a}$, $R^{3e}$ and $R^{4e}$ are as defined above or represent protected forms thereof), either with a Grignard reagent of formula R"MgX (wherein X is a halogen atom and R" is as defined above) and subsequent oxidation of the —CH(OH)R" terminal group obtained, or by reductive cleavage with e.g. a borohydride reducing agent in the presence of a hydroxy-protecting agent, to form initialy a vic-dihydroxy protected form of a compound of formula (XXI)

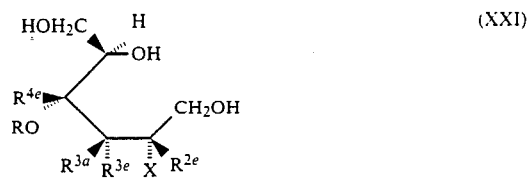

(wherein X, R, $R^{2e}$, $R^{3a}$, $R^{3e}$ and $R^{4e}$ are as defined above), which is subsequently oxidised to form a vic-dihydroxy-protected form of an aldehyde compound of formula (XXII)

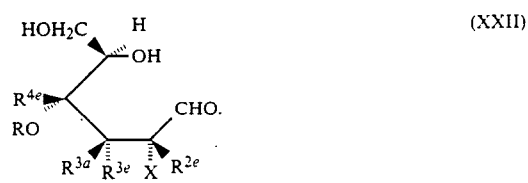

The vicinal hydroxy groups in the compounds of formula (XIX), (XXI) and (XXII) must be protected during the oxidations, most conveniently by acetal formation, e.g. with acetone.

The oxidised compound (XXII) may then preferably be subjected to a Grignard reaction with the reagent of formula R″MgX to introduce the optionally substituted hydrocarbyl group to form a terminal —CH$_2$(OH)R″ grouping, the alcohol compound formed being then subjected to a second oxidation to produce the desired starting compound of formula (XIX).

The compound of formula (XX) may suitably be prepared from a compound of formula (I) wherein R$^{1e}$ is a hydrogen atom by reaction with acetic anhydride under acidic conditions to cleave the C—O axial bond at the 1-position and generate acetoxy groups at the 1- and 6-carbon atoms, to form a compound of formula (XXIII)

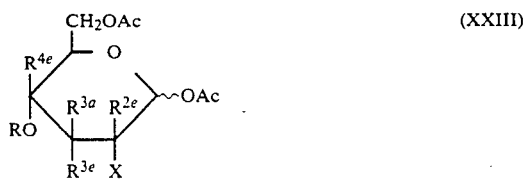

(XXIII)

followed by conventional deacylation.

P. for the preparation of salts of compounds of formula (I) and enantiomers thereof:

reacting a compound of formula (I) or enantiomer thereof, initially obtained, with an acid or base, optionally in the presence of a suitable solvent, to form the desired salt. The reaction may be carried out at or around room temperature, and/or under conventional reaction conditions.

Protective groups (as herein defined) which may be employed in any of the above reactions include those well known to persons skilled in the art. Appropriate methods for splitting off or converting said protective groups at any desired point of the reaction sequence will also be known in the art.

The above processes, where newly applied in the preparation of compounds of formula (I) and their enantiomers and salts, constitute further features of the present invention.

Certain of the compounds of formulae (V), (VI), (VII), (VIII), (XII), (XV), (XVI), (XVIII), (XIX), (XX), (XXI), (XXII) and (XXIII), useful as starting materials in the above reactions, are new, and they and the processes described herein for their preparation constitute still further features of the present invention.

In this regard may be mentioned compounds of formula (VI) and their corresponding alkali metal alkoxides, in particular those wherein X represents a lower alkoxy group and R$^{1e}$ represents a hydrogen atom or an optionally substituted hydrocarbyl group such as a lower alkyl group; compounds of formula (XX), in particular those wherein X represents a lower alkoxy group; compounds of formula (XXI) and (XXII) and vic-hydroxy-protected forms thereof, in particular those wherein X represents a lower alkoxy group and the vic-hydroxy groups are protected by an acetone acetal; and compounds of formula (XXIII), in particular those wherein X represents a lower alkoxy group.

Certain of the compounds of formula (I) and the enantiomers and salts thereof are new per se. Thus, in a still further aspect, the invention provides novel compounds of formula (Ia)

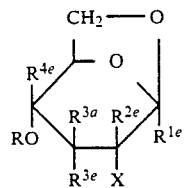

(Ia)

(in which

R represents an optionally substituted aralkyl group;

X represents an O-, N- or S-linked organic group, an optionally substituted hydrocarbyl group, a halogen atom, a hydroxy, amino, alkoxyamino, cyano, azido, sulpho or phospho group, or together with the group R$^{2e}$, X may represent a ketonic oxygen atom —O— or a group of formula —CH$_2$O—;

R$^{1e}$ represents a hydrogen atom or an optionally substituted hydrocarbyl group, or a formyl group;

R$^{2e}$ represents a hydrogen, atom, a hydroxy group or an optionally substituted hydrocarbyl or O-linked hydrocarbyl group; or, together with the group X, R$^{2e}$ may represent a ketonic oxygen atom —O— or a group of formula —CH$_2$O—;

R$^{3a}$ represents a hydrogen atom, a hydroxy group, or an optionally substituted alkoxy, alkenyloxy, aralkoxy or C$_{1-4}$ hydrocarbyl group;

R$^{3e}$ represents a hydrogen atom, a hydroxy group or an optionally substituted hydrocarbyl or O-linked hydrocarbyl group; and R$^{4e}$ represents a hydrogen atom or an optionally substituted hydrocarbyl group;

with the proviso that, when R represents a benzyl group and R$^{1e}$, R$^{2e}$ and R$^{4e}$ all represent hydrogen atoms, then if (i) R$^{3a}$ and R$^{3e}$ each represents a hydrogen atom, X cannot represent a hydroxy or benzyloxy group;

(ii) R$^{3a}$ represents a hydroxy group and R$^{3e}$ represents a hydrogen atom, X cannot represent a methyl, allyl, benzyloxy, tetrahydropyranyloxy, amino, acetamido, azido, NHC(S)SCH$_3$, hydroxy or methoxy group, a 3-hydroxy-prop-1-enyl, 3-hydroxy-2-methyl-prop-1-enyl or 3-hydroxyprop-1-ynyl group or a silylated derivative of such groups, or a halogen atom;

(iii) R$^{3a}$ represents a benzyloxy group and R$^{3e}$ represents a hydrogen atom, X cannot represent a hydroxy, benzyloxy, benzoyloxy, prop-1-enyloxy, allyloxy, methoxy, acetoxy, azido, acetamido or tetrahydropyranyloxy group, or a halogen atom or together with the group R$^{2e}$ a ketonic oxygen atom;

(iv) R$^{3a}$ represents a propoxy group and R$^{3e}$ represents a hydrogen atom, X cannot represent a hydroxy, benzyloxy or tetrahydropyranyloxy group;

(v) R$^{3a}$ represents a hydrogen atom and R$^{3e}$ represents a hydroxy group, X cannot represent a hydroxy or benzyloxy group, or a fluorine atom;

(vi) R$^{3a}$ represents a methoxy group and R$^{3e}$ represents a hydrogen atom, X cannot represent a methyl, methoxy or benzyloxy group;

(vii) R$^{3a}$ represents a dodecyloxy or 2-butenyl group and R$^{3e}$ represents a hydrogen atom, X cannot represent a benzyloxy group; and (viii) R$^{3a}$ represents a triphenylmethyl group and R$^{3e}$ represents a hydrogen atom, X cannot represent an acetylamino group;

and with the further proviso that when OR and R$^{3a}$ each represents a benzyloxy group, R$^{1e}$, R$^{2e}$, R$^{3e}$ represent hydrogen atoms, and $R^{4e}$ represents a methyl group, X cannot represent a methyl group, and with the second further proviso that when OR and $R^{3a}$ each represents a p-halo- or p-methyl-benzyloxy group and $R^{1e}$, $R^{2e}$, $R^{3e}$ represent hydrogen atoms, X cannot represent respectively a p-halo- or p-methyl-benzyloxy group), and enantiomers and salts thereof.

The invention in a still further aspect provides methods as hereinbefore described for the preparation of novel compounds of formula (Ia) as defined, and enantiomers and salts thereof.

The compositions according to the present invention may be used especially as weed-killers. Certain of the compositions may act as total herbicides while others may act as selective herbicides. Certain compositions may also be used as plant-growth regulators.

The compositions according to the present invention may be used, for example, to control or eliminate grass weeds, broad-leafed weeds or sedge weeds.

The compositions of the present invention may be particularly effective against monocotyledon weeds. However, the use of compositions according to the invention is in no way restricted to these groups of plants.

The compositions of the invention may be used both as pre-emergence and post-emergence herbicides. Pre-emergence herbicides are usually used to treat the soil in which a crop is to be planted, by application before or during seeding, or after seeding and before the crop emerges. Post-emergence herbicides are applied after the crop plants have emerged from the soil. Certain of the compositions may be used as general (i.e. non-selective) herbicides whereas others may be used as selective herbicides for control of weeds in particular crops. A number of the compositions show selective herbicidial activity when applied pre-emergence to soya, rape, and sugar-beet, or post-emergence to cotton, rape, sugar-beet, and rice. Pre-emergence application may also be appropriate in cotton at lower rates of application.

The present invention also provides a method of combating weeds which comprises applying to the weeds, or to a habitat thereof, a composition of the present invention.

A broad range of compounds have been tested with regard to their herbicidal and/or plant growth regulatory activity, as will now be described. For convenience the compounds are referred to simply by the number of the Example (see below) in which the preparation of the compound is specifically described. Three of the compounds tested were prepared according to literature references in which the compounds per se are described. These are as follows:

Compound "A": 1,6-anhydro-4-O-benzyl-2-deoxy-2-C-methyl-β-D-glucopyranose, prepared as described in Tetrahedron Lett. (1981) 22, 4315–4318, Compound "B": 1,6-anhydro-2,4-di-O-benzyl-β-D-glucopyranose, prepared as described in Can. J. Chem. 60 (1982), 299–303, and Compound "C": 1,6-anhydro-2,3,4-tri-O-benzyl-β-D-glucopyranose, prepared as described in Chem. Ber. 70 (1937) 1848–1856.

For comparison purposes the commercial herbicide "Diuron" has also been tested on the one plant screen.

ONE-PLANT SCREEN

*Arabidopsis thaliana* plants were grown in a growth room (24° C.) under a 16:8 hour light:dark regime. Single plants were grown in test tubes containing an agar nutrient medium (14 ml) and a given concentration of test chemical. Each chemical was tested in a 2-fold dilution series starting with a concentration of 16 ppm. Active compounds were tested down to a concentration of 0.031 ppm at least. Nine replicates were used at each rate. Toxic effects were generally apparent by the rosette stage at about 2 weeks after seeding. A toxic concentration was regarded as that which killed all replicates by the rosette stage. Plant growth regulatory (pgr) effects were assessed from pod numbers on mature plants at about 5 weeks after seeding. The lowest concentration (ppm) to effect 90% of the pod numbers ($LC_{90}$) was estimated for each compound from eye-fitted curves. There was a high correlation ($r=0.9$) between pod numbers and seed weight.

In three cases, seeds were collected and checked for their viability to assess possible toxic effects on progeny at sublethal concentrations to the adult plant (see Table 2).

Table 1 shows the activity against *A. thaliana*.

The effect of three of the compounds, at 16, 8 and 4 ppm in the growth medium, on the weight of seed produced and its viability is shown in Table 2.

TABLE 1

| Compound (Example No.) | Minimum herbicidal concentration (ppm) | Plant growth activity est. $LC_{90}$ (ppm) |
|---|---|---|
| 4.1 | 0.13 | <0.03* |
| 3.1 | 1 | 0.08 |
| 13 | 1 | <0.25* |
| 4.2 | 4 | 0.5 |
| 12 | 4 | 0.5 |
| 3.2 | 4 | <1* |
| 4.3 | 8 | 0.6 |
| 3.4 | 8 | 2.5 |
| 9 | 16 | 7.0 |
| 3.3 | >16 | 3.5 |
| 11 | >16 | 7.0 |
| 5 (1st exemplified compound) | >16 | 8.6 |
| 2 (2nd title compound) | >16 | 9.3 |
| 14 | >16 | 10.9 |
| 5 (2nd exemplified compound) | >16 | 11.9 |
| 8 (1st title compound) | >16 | 12.3 |
| 8 (2nd title compound) | >16 | −8.0 |
| 10 | >16 | 13.2 |
| "A" | >16 | 14.4 |
| 7 | >16 | 17.0 |
| 6 | >16 | −8.0 |
| Comparison Compound Diuron | 0.5 | Not tested |

Lowest concentration which reduced the seed pods by 90% compared with controls.
*Not tested below this concentration.

TABLE 2

| Compound (Example No.) | Concentration in growth medium (ppm) | Average seed weight (mg) | Viability of progeny (%) |
|---|---|---|---|
| 6 | 16 | 3.2 | 44 |
|  | 8 | 4.5 | 55 |
|  | 4 | 10.1 | Not tested |
| 2 (2nd title | 16 | 0 | 0 |
|  | 8 | 1.3 | 12 |

TABLE 2-continued

| Compound (Example No.) | Concentration in growth medium (ppm) | Average seed weight (mg) | Viability of progeny (%) |
|---|---|---|---|
| compound) 14 | 4 | 5.3 | 61 |
| | 16 | 0.2 | 0 |
| | 8 | 1.0 | 15 |
| | 4 | 7.5 | 55 |
| Control | 0 | 11 | 97 |

GLASS HOUSE TESTS FOR HERBICIDAL ACTIVITY

The compounds were applied to a broad range of crop and mono- and dicot weed species using a travelling boom track sprayer at a volume equivalent to 1000 l ha$^{-1}$ and at varying concentrations corresponding to application rates of 0.2, 1.0 or 1.25 (pre-emergence) and 1.0 or 1.25 (post emergence) kg ha$^{-1}$. Assessments were made for pre-emergence activity 20 days after direct spraying onto the seed, the seed having been covered with a compost for that period. Assessments were also made for post-emergence activity 13 days after spraying onto young plants.

The assessment scale used was as follows:

0 = 0-10% damage
1 = 11-25% damage
2 = 26-50% damage
3 = 51-80% damage
4 = 81-95% damage
5 = 96-100% damage The results are shown in Tables 3 and 4.

A test at an application rate of 8 kg ha$^{-1}$ was also carried out on certain of the compounds. The test procedure is essentially the same as that described above, except that the assessment scale is as follows:

0 = 0-25% damage
1 = 26-50% damage
2 = 51-75% damage
3 = 76-100% damage

The results of this test are shown in Table 5.

| Abbreviations used for Plants in Tables 3, 4 and 5 | | |
|---|---|---|
| A | Lt | Lettuce |
| | Sb | Sugar-beet |
| | Rp | Rape |
| | Ct | Cotton |
| | Sy | Soybean |
| | Mz | Maize |
| | Ww | Winter wheat |
| | Rc | Rice |
| | To | Tomato |
| B | Bd | Bidens pilosa |
| | Ip | Ipomoea purpurea |
| | Am | Amaranthus retroflexus |
| | Pi | Polygonum aviculare |
| | Ca | Chenopodium album |
| | Ga | Galium aparine |
| | Xa | Zanthium spinosum |
| | Xs | Xanthium strumarium |
| | Ab | Abutilon theophrasti |
| | Co | Cassia obtusifolia |
| C | Av | Avena fatua |
| | Dg | Digitaria sanguinalis |
| | Al | Alopecurus myosuroides |
| | St | Setaria viridis |
| | Ec | Echinochloa crus-galli |
| | Sh | Sorghum halepense |
| | Ag | Agropyron repens |
| | Cn | Cyperus spp. either Cyperus rotundus or Cyperus esculentus |

A = Crops
B = Dicot Weeds
C = Monocot Weeds

TABLE 3

| COMPOUND (EXAMPLE NO.) | RATE OF APPLICATION kg/ha | PRE- OR POST-EMERGENCE APPLICATION | Sb | Rp | Ct | Sy | Mz | Ww | Rc | Bd | Ip | Am | Pi | Ca | Ga | Xa | Xs | Ab | Co | Av | Dg | Al | St | Ec | Sh | Ag | Cn |
|---|---|---|---|---|---|---|---|---|---|---|---|---|---|---|---|---|---|---|---|---|---|---|---|---|---|---|---|
| 13 | 1.25 | Pre | 3 | 2 | 2 | 2 | 5 | 5 | 5 | 3 | 0 | 3 | 3 | 3 | 5 | 0 | — | 3 | 3 | 5 | 5 | 5 | 5 | 5 | 5 | 5 | 4 |
|  | 1.0 | Post | 2 | 0 | 3 | 2 | 3 | 2 | 3 | 2 | 2 | 0 | 2 | 2 | — | — | 2 | 3 | 0 | 3 | 5 | 2 | 3 | 3 | 3 | 3 | 0 |
| 4.4 | 1.0 | Pre | 4 | 4 | 4 | 5 | 5 | 5 | 5 | 5 | 0 | 4 | 4 | 4 | 5 | 4 | — | 3 | 3 | 5 | 5 | 5 | 5 | 5 | 5 | 5 | — |
|  | 1.0 | Post | 3 | 3 | 0 | 3 | 3 | 4 | 1 | 2 | 0 | 0 | 3 | 5 | 2 | — | 2 | 3 | 1 | 3 | 2 | 3 | 2 | 3 | 3 | 2 | 3 |
| 4.5 | 0.2 | Pre | 3 | 2 | 2 | 3 | 5 | 4 | 5 | 3 | 0 | 3 | 4 | 4 | 5 | — | 2 | 3 | 3 | 5 | 5 | 5 | 5 | 5 | 5 | 4 | 4 |
|  | 1.0 | Post | 3 | 1 | 2 | 3 | 3 | 3 | 3 | 3 | 1 | 2 | 3 | 2 | 2 | 2 | — | 3 | 2 | 3 | 4 | 3 | 4 | 3 | 3 | 2 | 0 |
| 4.1 | 1.0 | Pre | 3 | 3 | 2 | 4 | 3 | 3 | 5 | 3 | 0 | 3 | 3 | 2 | 5 | 4 | 2 | 4 | 3 | 4 | 5 | 5 | 3 | 5 | 4 | 5 | 5 |
|  | 1.0 | Post | 3 | 1 | 3 | 0 | 0 | 0 | 0 | 0 | 2 | 0 | 3 | 2 | 1 | 0 | 0 | 0 | 0 | 0 | — | 0 | 2 | 0 | 2 | 0 | 2 |
| 4.6 | 1.0 | Pre | 4 | 4 | 4 | 5 | 5 | 4 | 5 | 4 | 0 | 4 | 5 | 5 | 5 | — | — | 4 | 3 | 5 | 5 | 5 | 5 | 5 | 5 | 5 | 4 |
|  | 1.0 | Post | 2 | — | 1 | 2 | 3 | 2 | 0 | 0 | 1 | 0 | 2 | 3 | 1 | 4 | 2 | 3 | 0 | 4 | 4 | 4 | 4 | 4 | 4 | 4 | 4 |
| 4.2 | 1.0 | Pre | — | 0 | 3 | 0 | 4 | 5 | 5 | 2 | 0 | 0 | 3 | 3 | 4 | 0 | 0 | 0 | 2 | 0 | 3 | 2 | 2 | 3 | 3 | 0 | 0 |
|  | 1.0 | Post | 0 | 0 | 0 | — | 0 | 0 | 0 | 0 | 0 | 0 | 0 | 0 | 5 | 0 | 0 | 2 | 0 | 4 | 5 | 5 | 5 | 5 | 5 | 5 | 4 | 0 |
| 4.3 | 1.0 | Pre | 1 | 0 | 3 | 5 | 4 | 5 | 0 | 2 | 0 | 2 | 2 | 2 | 5 | — | — | 3 | 2 | 4 | 3 | 5 | 3 | 5 | 3 | 5 | 4 |
|  | 1.0 | Post | 2 | 3 | — | 3 | 2 | 0 | 5 | 3 | 1 | 2 | 2 | 2 | 2 | 2 | — | — | 0 | 4 | 4 | 5 | 2 | 5 | 4 | 4 | 0 | — |
| 3.2 | 1.0 | Pre | 3 | — | — | — | 4 | 5 | 0 | 3 | 2 | 3 | 2 | 2 | 2 | — | — | 0 | 3 | 3 | 4 | 5 | 3 | 5 | 3 | 4 | 0 | 0 |
|  | 1.0 | Post | 3 | 1 | 3 | 4 | 4 | 5 | 5 | 4 | 0 | 3 | 4 | 4 | 5 | — | 0 | — | 3 | 4 | 5 | 5 | 5 | 5 | 5 | 5 | 5 | 0 |
| 3.3 | 1.0 | Pre | 3 | 0 | — | 3 | 3 | 1 | — | 3 | 0 | 0 | 3 | 3 | — | — | 2 | 3 | 0 | 0 | 3 | 5 | 0 | 5 | 0 | 3 | 5 | — |
| 4.7 | 1.0 | Post | 2 | 1 | 0 | 2 | 0 | 4 | 2 | 2 | 0 | 3 | 3 | 2 | 0 | — | 0 | — | 0 | — | 3 | 2 | 4 | 4 | 3 | 2 | 5 | — |
| 4.8 | 1.0 | Pre | 3 | 0 | — | 2 | — | 5 | 2 | 0 | 0 | 0 | 0 | 0 | 0 | — | — | — | 3 | — | 4 | 4 | 3 | 4 | 3 | 4 | 0 | 0 |
|  | 1.0 | Post | 0 | — | 1 | 2 | — | — | 3 | 1 | — | 0 | 0 | 2 | — | 2 | — | — | 2 | — | — | — | — | — | — | — | — | — |
| 4.9 | 1.0 | Pre | 3 | — | 0 | 2 | 2 | 4 | 0 | 5 | 0 | 2 | 3 | 2 | 2 | — | — | 2 | 2 | 2 | 5 | 5 | 4 | 5 | 5 | 5 | 4 | 0 |
|  | 1.0 | Post | 3 | 1 | — | 3 | 3 | 2 | 5 | 3 | 0 | 3 | 3 | 2 | — | 2 | — | 2 | 2 | 2 | 2 | 2 | 2 | 3 | 2 | 3 | 3 | 3 |
| 3.6 | 1.0 | Pre | 2 | — | — | — | 4 | 4 | 0 | 2 | — | 2 | 4 | 3 | 2 | 2 | — | — | 2 | 0 | 3 | 2 | 0 | 3 | 0 | 2 | 0 | — |
|  | 1.0 | Post | 0 | 0 | 0 | 0 | 2 | 0 | 0 | 0 | 0 | 2 | 4 | 3 | 0 | 4 | — | 0 | 0 | 0 | 0 | 0 | 0 | 0 | 0 | 5 | — | 3 |
| 4.12 | 1.0 | Pre | 4 | 4 | 4 | 5 | 5 | 4 | 5 | 5 | 0 | 4 | 5 | 5 | 5 | — | — | 4 | 3 | 5 | 5 | 5 | 5 | 5 | 5 | 5 | 5 | 3 |
|  | 1.0 | Post | 2 | 1 | 2 | 2 | 3 | 2 | — | 2 | 0 | 0 | 2 | 2 | 3 | 3 | — | 2 | 0 | 3 | 3 | 3 | 3 | 3 | 3 | 3 | 3 | 3 |
| 4.14 | 1.0 | Pre | 3 | 0 | 3 | 3 | 3 | 3 | — | 3 | 0 | 0 | 2 | 3 | 2 | — | — | 0 | 0 | 3 | 5 | 3 | 3 | 3 | 3 | 0 | 3 | 0 |
|  | 1.0 | Post | 0 | 0 | 0 | 0 | 0 | 0 | — | 0 | 0 | 0 | 0 | 0 | 0 | — | — | 0 | 0 | 0 | 0 | 0 | 0 | 0 | 0 | 0 | 0 | 0 |
| 4.15 | 1.0 | Pre | 4 | 4 | 4 | 5 | 5 | 4 | — | 5 | 0 | 4 | 5 | 5 | 5 | — | — | 4 | 3 | 5 | 5 | 5 | 5 | 5 | 5 | 5 | 5 | 3 |
|  | 1.0 | Post | 2 | 0 | 3 | 2 | 3 | 5 | 5 | 3 | 2 | 3 | 4 | 4 | 4 | 4 | 2 | 4 | 4 | 4 | 5 | 4 | 5 | 4 | 5 | 5 | 5 | 3 |
| 4.16 | 1.0 | Pre | 2 | 0 | 0 | 2 | 5 | 3 | — | 2 | 0 | 0 | 2 | 3 | 2 | 3 | — | 2 | 0 | 2 | 5 | 5 | 3 | 5 | 4 | 5 | 3 | 3 |
|  | 1.0 | Post | 3 | 0 | 0 | 0 | 3 | 3 | 5 | 3 | 0 | 2 | 4 | 3 | 5 | — | — | 3 | 2 | 3 | 5 | 3 | 3 | 3 | 3 | 3 | 3 | 0 |
| 4.20 | 1.0 | Pre | 1 | 2 | 0 | 0 | 0 | 2 | — | 2 | 0 | 0 | 0 | 2 | — | 0 | — | 0 | 0 | 0 | 0 | 0 | 0 | 0 | 0 | 0 | 0 | 0 |
|  | 1.0 | Post | 0 | 0 | 0 | 0 | 5 | 0 | 0 | 0 | 0 | 4 | 5 | 5 | 5 | 4 | — | 4 | 5 | 5 | 5 | 5 | 5 | 5 | 5 | 5 | 3 | 3 |
| 4.17 | 1.0 | Pre | 2 | 0 | 4 | 5 | 5 | 4 | 5 | 5 | 0 | 3 | 2 | 3 | 2 | 3 | — | 2 | 0 | 4 | 2 | 2 | 2 | 3 | 3 | 3 | 0 | 0 |
|  | 1.0 | Post | 4 | 1 | 0 | 2 | 5 | 5 | 5 | 5 | 0 | 5 | 4 | 5 | 5 | 0 | — | 4 | 5 | 5 | 5 | 5 | 5 | 5 | 5 | 5 | 0 | 0 |
| 4.18 | 1.0 | Pre | 0 | 0 | 3 | 0 | 3 | 3 | 5 | 3 | 0 | 3 | 3 | 2 | 2 | 3 | 0 | 3 | 0 | 3 | 3 | 3 | 3 | 3 | 2 | 3 | 0 | 0 |
|  | 1.0 | Post | 0 | 0 | 0 | — | 0 | 0 | — | 0 | 0 | 0 | 0 | 0 | 0 | — | — | 0 | 0 | 0 | 0 | 0 | 0 | 0 | 0 | 0 | 0 | 0 |
| 4.43 | 1.0 | Pre | 3 | 2 | 0 | 3 | 5 | 4 | 5 | 3 | 0 | 3 | 3 | 5 | 5 | 3 | — | 4 | 5 | 5 | 5 | 5 | 5 | 5 | 5 | 5 | 5 | 3 |
|  | 1.0 | Post | 0 | 0 | 2 | 2 | 2 | 3 | — | 3 | 0 | 3 | 2 | 2 | 2 | — | — | 4 | 2 | 2 | 2 | 2 | 3 | 3 | 3 | 3 | 3 | 0 |
| 4.41 | 1.0 | Pre | 4 | 3 | 3 | 3 | 5 | 5 | 5 | 5 | 0 | 4 | 4 | 4 | 5 | 4 | — | 3 | 3 | 5 | 5 | 5 | 5 | 5 | 5 | 5 | 5 | 0 |
|  | 1.0 | Post | 1 | 0 | 0 | 2 | 3 | 3 | — | 2 | 0 | 2 | 2 | 3 | 2 | 3 | — | 2 | 2 | 2 | 3 | 2 | 3 | 3 | 3 | 3 | 3 | 0 |
| 4.48 | 1.0 | Pre | 4 | 3 | 3 | 4 | 5 | 5 | 5 | 5 | 0 | 4 | 4 | 4 | 5 | 4 | — | 4 | 3 | 5 | 5 | 4 | 5 | 4 | 4 | 4 | 4 | 0 |
|  | 1.0 | Post | 3 | 3 | 3 | 3 | 3 | 3 | — | 3 | 0 | 2 | 3 | 4 | 5 | 3 | 0 | 3 | 2 | 4 | 4 | 4 | 4 | 4 | 3 | 3 | 4 | 0 |
| 4.51 | 1.0 | Pre | 3 | 3 | 3 | 2 | 5 | 5 | 5 | 4 | 0 | 4 | 4 | 4 | 5 | 4 | 0 | 3 | 2 | 4 | 4 | 4 | 3 | 4 | 3 | 4 | 4 | 0 |
| 4.52 | 1.0 | Post | 4 | 0 | 3 | 3 | 5 | 5 | 5 | 5 | 0 | 4 | 2 | 4 | 5 | — | — | 3 | 2 | 4 | 4 | 5 | 4 | 4 | 4 | 4 | 4 | 0 |
| 4.44 | 1.0 | Pre | 2 | 0 | 3 | 4 | 5 | 3 | 5 | 4 | 0 | 4 | 5 | 5 | 5 | 4 | — | 4 | 2 | 5 | 5 | 4 | 5 | 4 | 5 | 5 | 5 | — |

TABLE 3-continued

| COMPOUND (EXAMPLE NO.) | RATE OF APPLICATION kg/ha | PRE- OR POST-EMERGENCE APPLICATION |
|---|---|---|
| 4.49 | 1.0 | Post |
| 4.54 | 1.0 | Pre |
|  | 1.0 | Post |
| 4.39 | 1.0 | Pre |
|  | 1.0 | Post |
| 4.40 | 1.0 | Pre |
|  | 1.0 | Post |
| 4.24 | 1.0 | Pre |
|  | 1.0 | Post |
| 4.27 | 1.0 | Pre |
|  | 1.0 | Post |
| 4.30 | 1.0 | Pre |
|  | 1.0 | Post |
| 4.26 | 1.0 | Pre |
|  | 1.0 | Post |
| 4.21 | 1.0 | Pre |
|  | 1.0 | Post |
| 4.22 | 1.0 | Pre |
|  | 1.0 | Post |
| 4.23 | 1.0 | Pre |
|  | 1.0 | Post |
| 4.46 | 1.0 | Pre |
|  | 1.0 | Post |
| 4.35 | 1.0 | Pre |
|  | 1.0 | Post |
| 4.45 | 1.0 | Pre |
|  | 1.0 | Post |
| 4.42 | 1.0 | Pre |
|  | 1.0 | Post |
| 4.29 | 1.0 | Pre |
|  | 1.0 | Post |
| 4.31 | 1.0 | Pre |
|  | 1.0 | Post |
| 15.1 | 1.25 | Pre |
|  | 1.25 | Post |
| 3.11 | 1.25 | Pre |
|  | 1.25 | Post |
| 3.12 | 1.25 | Pre |
|  | 1.25 | Post |
| 4.37 | 1.25 | Pre |
| 15.3 | 1.25 | Post |
|  | 1.25 | Pre |
|  | 1.25 | Post |
| 15.4 | 1.25 | Pre |
|  | 1.25 | Post |
| 16.1 | 1.25 | Pre |
|  | 1.25 | Post |
| 16.2 | 1.25 | Pre |
|  | 1.25 | Post |

TABLE 3-continued

| COMPOUND (EXAMPLE NO.) | RATE OF APPLICATION kg/ha | PRE- OR POST-EMERGENCE APPLICATION | Sb | Rp | Ct | Sy | Mz | Ww | Rc | Bd | Ip | Am | Pi | Ca | Ga | Xa | Xs | Ab | Co | Av | Dg | Al | St | Ec | Sh | Ag | Cn |
|---|---|---|---|---|---|---|---|---|---|---|---|---|---|---|---|---|---|---|---|---|---|---|---|---|---|---|---|
| 16.3 | 1.25 | Pre | 3 | 1 | 3 | 3 | 4 | 4 | 5 | 3 | 1 | 0 | 3 | 3 | 3 | 2 | — | 2 | 1 | 5 | 5 | 5 | 5 | 5 | 4 | 5 | 4 |
|  | 1.25 | Post | 0 | 0 | 1 | 2 | 3 | 3 | 1 | 2 | 1 | 1 | 2 | 3 | 0 | — | — | 3 | 1 | 3 | 3 | 2 | 2 | 3 | 2 | 1 | 1 |
| 18 | 1.25 | Pre | 4 | 2 | 3 | 4 | 4 | 5 | 4 | 4 | 1 | 3 | 4 | 4 | 4 | 2 | — | 4 | 3 | 4 | 5 | 5 | 4 | 5 | 5 | 5 | 5 |
|  | 1.25 | Post | 3 | 2 | 4 | 4 | 2 | 3 | 0 | 4 | 1 | 3 | 3 | 4 | 2 | — | — | 4 | 0 | 3 | 3 | 2 | 4 | 4 | 3 | 3 | 0 |
| 4.33 | 1.25 | Pre | 4 | 4 | 4 | 4 | 4 | 5 | 5 | 4 | — | 4 | 4 | 4 | 5 | 2 | — | 4 | 4 | 4 | 4 | 5 | 4 | 4 | 5 | 5 | 5 |
|  | 1.25 | Post | 3 | 2 | 1 | 4 | 5 | 3 | 5 | 4 | 3 | 3 | 4 | 4 | — | 4 | 4 | 4 | 3 | 5 | 4 | 5 | 4 | 4 | 4 | 3 | 0 |
| 4.32 | 1.25 | Pre | 4 | 3 | 3 | 4 | 4 | 5 | 5 | 3 | — | 3 | 4 | 4 | 5 | — | — | 4 | 4 | 4 | 4 | 5 | 4 | 5 | 5 | 5 | 5 |
|  | 1.25 | Post | 3 | 3 | 1 | 4 | 3 | 3 | 3 | 3 | 3 | 2 | 3 | 3 | 4 | 1 | — | 3 | 3 | 3 | 3 | 4 | 3 | 4 | 3 | 3 | 2 |
| 22 | 1.25 | Pre | 4 | 3 | 1 | 4 | 4 | 4 | 4 | 3 | 2 | 2 | 4 | 4 | 5 | — | — | 3 | 3 | 4 | 5 | 5 | 3 | 5 | 5 | 3 | 2 |
|  | 1.25 | Post | 3 | 1 | 4 | 0 | 3 | 0 | 5 | 2 | 1 | 2 | 3 | 3 | 0 | — | — | 3 | 2 | 3 | 3 | 1 | 2 | 4 | 4 | 1 | 3 |
| 12 | 1.25 | Pre | 4 | 3 | 4 | 3 | 4 | 5 | 5 | 2 | 0 | 2 | 4 | 4 | 5 | — | — | 2 | 0 | 4 | 5 | 5 | 3 | 4 | 4 | 5 | 0 |
|  | 1.25 | Post | 1 | 2 | 0 | 3 | 1 | 2 | — | 2 | 0 | 3 | 1 | 2 | 0 | — | — | 3 | 2 | 0 | 3 | 1 | 2 | 4 | 1 | 1 | 4 |
| 4.34 | 1.25 | Pre | 3 | 2 | 3 | 3 | 3 | 4 | 0 | 2 | 0 | 0 | 3 | 3 | 4 | — | — | 3 | 0 | 4 | 4 | 4 | 3 | 5 | 5 | 5 | 0 |
|  | 1.25 | Post | 0 | 0 | 1 | 2 | 3 | 3 | 5 | 2 | — | 4 | 2 | 2 | 5 | 3 | — | 4 | 4 | 4 | 4 | 5 | 5 | 3 | 3 | 5 | 5 |
| 3.10 | 1.25 | Pre | 4 | 3 | 3 | 3 | 4 | 5 | 2 | 4 | 0 | 4 | 4 | 3 | 2 | — | — | 3 | 4 | 3 | 4 | 4 | 3 | 5 | 5 | 3 | 1 |
|  | 1.25 | Post | 2 | 3 | 3 | 3 | 3 | 2 | 2 | 4 | 4 | 3 | 3 | 3 | 2 | 3 | — | 3 | 3 | 2 | 5 | 3 | 3 | 4 | 3 | 2 | 5 |
| 4.36 | 1.25 | Pre | 4 | 3 | 1 | 4 | 4 | 4 | — | 4 | 0 | 3 | 4 | 3 | 4 | 2 | — | 3 | 1 | 3 | 5 | 5 | 3 | 5 | 5 | 4 | 5 |
|  | 1.25 | Post | 1 | 2 | 1 | 1 | 2 | 2 | 1 | 2 | 4 | 3 | 1 | 2 | 5 | — | — | 3 | 3 | 3 | 3 | 3 | 3 | 3 | 3 | 1 | 0 |
| 4.50 | 1.25 | Pre | 4 | 2 | 3 | 3 | 5 | 5 | 2 | 4 | 2 | 3 | 4 | 4 | 5 | 3 | — | 3 | 2 | 3 | 5 | 5 | 3 | 5 | 5 | 5 | 5 |
|  | 1.25 | Post | 0 | 0 | 0 | 2 | 3 | 3 | — | 4 | 2 | 3 | 3 | 3 | 1 | — | — | 1 | 0 | 2 | 3 | 3 | 3 | 5 | 3 | 1 | 0 |
| 3.1 | 1.0 | Pre | 3 | 0 | 3 | 5 | 5 | 3 | — | 5 | 2 | 2 | 4 | 0 | 5 | 2 | — | 3 | 0 | 5 | 5 | 5 | 5 | 5 | 5 | 5 | 5 |
|  | 1.0 | Post | 1 | 0 | 0 | 2 | 3 | 2 | — | 3 | 2 | 2 | 0 | 0 | 3 | — | — | 3 | 0 | 2 | 5 | 2 | 3 | 4 | 2 | 1 | — |

TABLE 4

| COMPOUND (EXAMPLE NO.) | RATE OF APPLICATION kg/ha | PRE- OR POST-EMERGENCE APPLICATION | TEST PLANTS | | | | | | | | | | | | |
|---|---|---|---|---|---|---|---|---|---|---|---|---|---|---|---|
| | | | Ip | Pi | Ca | Ga | Xa | Xs | Ab | Co | Av | Al | St | Sh | Cn |
| 8 (2nd title compound) | 1.0 | Pre | 0 | 0 | 0 | 0 | 0 | — | 0 | 0 | 0 | 0 | 0 | — | — |
| | 1.0 | Post | 1 | 0 | 2 | 0 | — | 0 | 0 | 1 | 0 | 0 | 0 | 2 | 0 |
| 6 | 1.0 | Pre | 0 | 0 | 0 | 0 | 0 | — | 0 | 0 | 0 | 0 | 0 | — | — |
| | 1.0 | Post | 2 | 2 | 0 | 2 | — | 0 | 1 | 2 | 0 | 2 | 2 | 3 | 3 |
| 2 (2nd title compound) | 1.0 | Pre | 0 | 0 | 0 | 0 | 0 | — | 0 | 0 | 0 | 0 | 0 | — | — |
| | 1.0 | Post | 1 | 2 | 3 | 3 | — | 2 | 0 | 2 | 2 | 0 | 1 | 4 | 0 |
| "B" | 1.0 | Pre | 0 | 0 | 0 | 0 | 0 | — | 0 | — | 0 | 0 | 0 | — | — |
| | 1.0 | Post | 0 | 0 | 0 | 0 | — | 0 | 1 | 2 | 0 | 0 | 0 | 3 | 0 |
| "C" | 1.0 | Pre | 1 | 0 | 0 | 0 | 0 | — | 0 | 0 | 0 | 0 | 0 | — | — |
| | 1.0 | Post | 3 | 0 | 2 | 0 | — | 0 | 1 | 1 | 0 | 0 | 3 | 4 | 0 |
| 11 | 1.0 | Pre | 0 | 2 | 1 | 0 | 0 | — | 0 | 0 | 0 | 0 | 1 | — | — |
| | 1.0 | Post | 2 | 0 | 3 | 0 | — | 0 | 3 | 3 | 1 | 0 | 1 | 2 | 0 |
| 3.4 | 1.0 | Pre | 0 | 1 | 1 | 0 | 0 | — | 3 | — | 0 | 0 | 0 | 0 | — |
| | 1.0 | Post | 1 | 3 | 2 | 0 | — | 0 | 0 | 3 | 1 | 0 | 3 | 0 | 1 |
| 7 | 1.0 | Pre | 0 | 0 | 1 | 1 | 0 | — | 0 | — | 1 | 1 | 0 | 0 | — |
| | 1.0 | Post | 1 | 0 | 1 | 0 | — | 0 | 0 | 1 | 0 | 0 | 3 | 0 | 1 |
| 1 | 1.0 | Pre | 0 | 0 | 0 | 1 | 0 | — | 0 | 0 | 0 | 0 | 0 | 0 | — |
| | 1.0 | Post | 1 | 2 | 1 | 0 | — | 0 | 0 | 0 | 0 | 0 | 4 | 0 | 1 |
| 3.5 | 1.0 | Pre | 0 | 0 | 0 | 2 | 1 | — | 0 | — | 0 | 3 | 0 | 5 | — |
| | 1.0 | Post | 1 | 0 | 0 | 0 | — | 0 | 0 | 0 | 2 | 0 | 2 | 0 | 0 |
| 20 | 1.0 | Pre | 0 | 0 | 0 | 0 | 0 | — | 1 | — | 0 | 1 | 0 | 0 | — |
| | 1.0 | Post | 1 | 0 | 0 | 0 | — | 0 | 0 | 0 | — | 0 | 5 | 0 | 1 |
| 3.7 | 1.0 | Pre | 1 | 0 | 0 | — | 3 | — | 0 | 0 | 0 | 0 | 0 | 0 | — |
| | 1.0 | Post | 1 | 0 | 0 | 0 | — | 0 | 2 | — | 0 | 0 | 0 | 0 | 0 |
| 15.2 | 1.0 | Pre | 1 | 4 | 4 | — | 4 | — | 4 | 3 | 5 | 5 | 5 | 5 | — |
| | 1.0 | Post | 0 | 2 | 4 | 1 | — | 2 | 3 | — | 3 | 2 | 0 | 4 | 2 |
| 25 | 1.0 | Pre | 0 | 0 | 0 | — | 0 | — | 0 | 0 | 0 | 0 | 0 | 0 | — |
| | 1.0 | Post | 0 | 1 | 0 | 0 | — | 0 | 0 | 0 | 1 | 0 | 1 | 0 | 1 |
| 24 | 1.0 | Pre | 0 | 0 | 0 | — | 0 | — | 0 | 0 | 5 | 0 | 0 | 0 | — |
| | 1.0 | Post | 0 | 1 | 0 | 1 | — | 0 | 0 | 1 | 0 | 0 | 1 | 0 | 0 |
| 27 | 1.0 | Pre | 0 | 0 | 0 | 5 | 0 | — | 0 | 0 | 1 | 0 | 0 | 0 | — |
| | 1.0 | Post | 0 | 1 | 0 | 0 | — | 0 | 0 | 2 | 0 | 0 | 0 | 1 | 0 |
| 5 (1st exemplified compound) | 1.0 | Pre | 0 | 3 | 0 | 0 | 0 | — | 0 | 0 | 0 | 0 | 0 | — | 5 |
| | 1.0 | Post | 0 | 0 | 0 | 0 | — | 0 | 0 | 0 | 0 | 0 | 0 | 0 | 0 |
| 3.8 | 1.25 | Pre | 0 | 4 | 4 | 4 | 1 | — | 4 | 4 | 2 | 4 | 5 | 4 | — |
| | 1.25 | Post | 3 | 2 | 3 | 1 | — | 2 | 3 | 2 | 1 | 2 | 2 | 0 | 0 |

TABLE 5

| COMPOUND (EXAMPLE NO.) | RATE OF APPLICATION kg/ha | PRE- OR POST-EMERGENCE APPLICATION | TEST PLANTS | | | |
|---|---|---|---|---|---|---|
| | | | Lt | To | Av | St |
| 2 (1st title compound) | 8 | Pre | 0 | 0 | 0 | 0 |
| | 8 | Post | 0 | 0 | 0 | 2 |
| 9 | 8 | Pre | 2 | 0 | 0 | 2 |
| | 8 | Post | 3 | 2 | 3 | 3 |
| 3.9 | 8 | Pre | 0 | 0 | 0 | 0 |
| | 8 | Post | 0 | 0 | 0 | 2 |
| 4.13 | 8 | Pre | 0 | 0 | 0 | 0 |
| | 8 | Post | 0 | 0 | 0 | 1 |
| 4.11 | 8 | Pre | 0 | 0 | 0 | 0 |
| | 8 | Post | 0 | 2 | 0 | 1 |
| 21 | 8 | Pre | 0 | 0 | 0 | 3 |
| | 8 | Post | 3 | 0 | 2 | 3 |
| 4.10 | 8 | Pre | 3 | 0 | 1 | 2 |
| | 8 | Post | 3 | 3 | 2 | 3 |
| 14 | 8 | Pre | 0 | 0 | 0 | 0 |
| | 8 | Post | 3 | 0 | 0 | 1 |
| 4.19 | 8 | Pre | 1 | 1 | 0 | 3 |
| | 8 | Post | 2 | 0 | 1 | 3 |
| 4.25 | 8 | Pre | 1 | 1 | 0 | 3 |
| | 8 | Post | 2 | 0 | 3 | 2 |
| 4.53 | 8 | Pre | 0 | 0 | 0 | 0 |
| | 8 | Post | 0 | 0 | 0 | 2 |
| 4.47 | 8 | Pre | 0 | 0 | 0 | 0 |
| | 8 | Post | 3 | 1 | 2 | 3 |
| 28 | 8 | Pre | 0 | 0 | 0 | 0 |
| | 8 | Post | 0 | 0 | 0 | 2 |
| 26 | 8 | Pre | 0 | 0 | 0 | 0 |
| | 8 | Post | 0 | 0 | 0 | 2 |
| 4.28 | 8 | Pre | 2 | 1 | 3 | 3 |
| | 8 | Post | 2 | 0 | 2 | 2 |

The biotest results demonstrate that the compounds and compositions of the present invention possess valuable and interesting herbicidal and/or plant growth regulatory properties, particularly against monocotyledon weed species.

The following non-limiting Examples are included as further illustration of the present invention.

Optical rotations were recorded in chloroform solution at a concentration of 0.5-3 g/100 ml at ambient temperature (approx 20° C.) on a Perkin Elmer 241 Polarimeter. $^1$H and $^{13}$C. nmr data were recorded in CDCl$_3$ on a Varian FT80 and/or a Varian XL200 spectrometer. Chemical shifts are given in ppm downfield from tetramethylsilane. h=hours. psi=pounds per square inch (1 psi =6.89 kPa).

PREPARATIVE EXAMPLE 1

1,6-Anhydro-3-deoxy-2-O-methyl-β-D-ribo-hexopyranose

A solution of 1,6-anhydro-4-O-benzyl-3-deoxy-2-O-methyl-β-D-ribo-hexopyranose (see Example 3(1)) (4.5 g) in ethanol (20 ml) was added to a suspension of 10% palladium on carbon (0.2 g) in ethanol (50 ml) and the resulting mixture was stirred in a hydrogen atmosphere until uptake of hydrogen had ceased (5 hours). Celite was added and the mixture was filtered through two layers of glass fibre filter paper. The filtrate was concentrated to give a quantitative yield of the title compound as a colourless syrup which crystallised spontaneously. Filtration with the aid of a little hexane gave 2.52 g (88% yield) of crystalline title compound, m.p. 67°-68° C.; $[\alpha]_D$ −87.2°.

PREPARATIVE EXAMPLE 2

1,6-Anhydro-2-O-benzoyl-3-deoxy-α-L-ribo-hexopyranose

A. 1,6-Anhydro-α-L-gulopyranose

Syrupy L-gulose was heated on a steam bath in water with strong acid resin (Dowex 50 W-X8, H+form) for 64 h. The solution was then filtered, the resin washed with water, and the combined filtrate was passed onto a column packed with strong base resin (Amberlite IRA-900, OH−form). The column was washed with distilled water to elute the title compound which crystallized from ethanol. Recrystallized from ethanol it has mp 155.5°-156.5° C. The column was then immediately washed with aqueous acetic acid (M) to elute unreacted L-gulose which was recycled to provide further title compound.

B. 1,6-Anhydro-2,3-O-benzylidene-α-L-gulopyranose

The product of step A (1.0 g) and benzaldehyde dimethyl acetal (1.13 g) were dissolved in dimethylformamide (10 ml) containing p-toluenesulphonic acid monohydrate (0.1 g, 0.1 eq) which had been dried by standing with phosphorous pentoxide and filtered through a sintered glass frit. The solution was placed under water pump vacuum connection via an air condenser, and heated at 55°-60°·C. for 20 min, then left at room temperature for 1 h. The product was then partitioned between chloroform (100 ml) and saturated aqueous bicarbonate. The organic phase was washed with water, dried (Na$_2$SO$_4$), and evaporated to a syrup still containing some dimethylformamide. The title compound was then isolated by flash chromatography (silica gel; eluant ethyl acetate/light pertroleum, 1:2) and crystallised from ethyl acetate/light pertroleum as needles (0.58 g, 38%) shown by $^1$H nmr to be a 1:1 mixture of exo- and endo- isomers: 5.98 and 5.85 (s,PhC$\underline{H}$), and 5.69s and 5.59d (H-1). Evaporation of the mother liquors provided a crystalline residue (0.55 g, 36%) which was a similar mixture of isomers.

C. 4-O-Acetyl-1,6-anhydro-2,O-benzoyl-3-deoxy-α-L-ribo-hexo-pyranose

Pyridinium dichromate (4.1 g) was added to a solution of acetic anhydride (5.2 g) in dichloromethane (50 ml) and the mixture was stirred at room temperature for 1 h, then the product of step B(4.2 g) was added and the resulting mixture was stirred for a further 1 h. Ethyl acetate (100 ml) was added and the mixture was filtered through a pad of silica gel (45 mm×45 mm) and the solids were washed with further ethyl acetate (100 ml). The combined filtrates were concentrated to dryness and the crude product was immediately dissolved in methanol (50 ml) and cooled to −78° C. Sodium borohydride (4 g) was added to the stirred solution and stirring was continued at −78° C. for 2 h. Neutralisation was effected by the careful addition of acetic acid and then the solution was concentrated to dryness. Ethyl acetate (100 ml) was added to the residue and the mixture was filtered through a pad of silica gel as before. The solids were washed with further ethyl acetate (2×100 ml) and the combined filtrates were concentrated to give 2.94 g of colourless syrupy 1,6-anhydro-2,3-O-benzylidene-β-L-allopyranose as a diastereomeric mixture due to the benzylidene acetal. This crude product was dissolved in pyridine/acetic anhydride (50 ml, 1:1 v/v) and allowed to stand at room temperature overnight, before being co-evaporated to dryness three times with toluene and once with carbon tetrachloride. The residue comprising the 4-O-acetate derivative was dissolved in carbon tetrachloride (150 ml) containing barium carbonate (11.6 g). The mixture was then heated under reflux while N-bromosuccinimide (2.5 g) was added slowly portion-wise, the heating being maintained for a further 0.5 h after the addition was complete. The cooled solution was filtered through a pad of silica gel, the solids were washed with carbon tetrachloride, and the combined filtrates were evaporated to dryness to yield 4-O-acetyl-1,6-anhydro-2-O-benzoyl-3-bromo-3-deoxy-α-L-glucopyranose.

This residue was dissolved in toluene (60 ml), and tri-n-butyltin hydride (4 g) was added. The solution was heated under reflux for 4 h, cooled, and concentrated to dryness. The residue was dissolved in acetonitrile (150 ml) and washed with hexane (3×50 ml). The acetonitrile phase was evaporated to dryness and the residue was purified by chromatography on silica gel and crystallisation from ethyl acetate/light petroleum to give the title compound (2.40 g), m.p. 120°-121° C. $[\alpha]_D$ −24.8°.

D. 1,6-Anhydro-2-O-benzoyl-3-deoxy-β-L-ribo-hexopyranose

A solution of the product of step C (1.0 g) in dichloromethane (5 ml) and 0.6M hydrochloric acid in anhydrous methanol (10 ml) was allowed to stand at room temperature for 16 h. Chloroform (30 ml) was added and the solution was washed with saturated aqueous sodium hydrogen carbonate, dried (MgSO$_4$) and concentrated to dryness. Trituration of the residue with ethyl acetate/light petroleum gave crystalline title compound (0.77 g) in two crops; $^{13}$C-nmr data: 99.5 (C-1), 68.6 and 66.2 (C-2 and C-4), 28.7 (C-3), 77.4 (C-5), 65.5 (C-6), 133.3, 129.6 and 128.5 (aromatic).

PREPARATIVE EXAMPLE 3

1,6-Anhydro-4-O-benzyl-3-deoxy-2-O-p-toluenesulphonyl-β-D-arabino-hexopyranose

A solution of 1,6-anhydro-4-O-benzyl-3-deoxy-β-D-arabinohexopyranose (see Example 2) (2.0 g) in dry pyridine (30 ml) containing p-toluenesulphonyl chloride (2.0 g) was allowed to stand at room temperature for 24 h. Water (0.5 ml) was added and five minutes later chloroform (100 ml). The mixture was washed with water (×2), 2M aqueous hydrochloric acid, 1M aqueous sodium hydroxide, and water. The organic layer was dried (MgSO$_4$) and concentrated to a light yellow syrup. Trituration with ethanol gave crystalline title compound (2.83 g, 83%).

PREPARATIVE EXAMPLE 4

(1R,2S,4R)-5-Ethyl-2-hydroxy-4-methoxy-6,8-dioxabicyclo[3.2.1]octane

A solution of (1R,2S,4R)-2-benzyloxy-5-ethyl-4-methoxy-6,8-dioxabicyclo[3.2.1]octane (see Example 15.2) (3.4 g) in absolute ethanol (150 ml) containing acetic acid (2 ml) and 5% palladium on barium sulphate (1 g) was shaken in a hydrogen atmosphere at 40 p.s.i for 24 h, and then the solution was filtered and the solvent was removed. Chromatography of the residue on silica gel gave the title alcohol; m.p. 52°–53° C.; $[\alpha]_D$ −97.1°; $^{13}$C nmr data: 108.2 (C-5), 78.7 and 78.0 (C-1 and C-4), 66.9 (C-2), 66.3 (C-7), 57.6 (OCH$_3$), 27.0 and 26.0 (C-3 and CH$_2$CH$_3$), and 6.4 (CH$_2$CH$_3$).

PREPARATIVE EXAMPLE 5

Methyl 4,6-O-benzylidene-3-deoxy-2-O-methyl-α-D-ribo-hexopyranoside

Methyl 4,6-O-benzylidene-α-D-glucopyranoside (Carbohydr. Res., 1980, 86, 158–160) was converted to its 2,3-di-O-p-toluenesulphonate following the procedure of Vis and Karrer (Helv. Chim. Acta, 1954, 46, 378–381). The ditosylate was treated with lithium aluminum hydride in dry tetrahydrofuran as described by Vis and Karrer (Helv. Chim. Acta, 1954, 46, 378–381), using an alternative work-up procedure: Excess lithium aluminium hydride was destroyed by dropwise addition of saturated aqueous ammonium chloride at 0° C. with vigorous stirring. The mixture was dried with anhydrous sodium sulphate and filtered. The solids were washed thoroughly with portions of tetrahydrofuran. The combined filtrate and washings were evaporated. Trituration of the residue with ethanol and recrystallisation from the same solvent gave methyl 4,6-O-benzylidene-3-deoxy-α-D-ribo-hexopyranoside (41%). A second crop of the same material (up to 61% total yield) was obtained from the mother liquors by further crystallisation or by flash chromatography. Melting point, optical rotation and $^1$H nmr spectrum were in good agreement with published data, (Helv. Chim. Acta, 1954, 46 378–381; Bull. Chem. Soc. Japan, 1970, 43 1212–1218).

This compound was O-methylated (see Example 3) to give the title compound as a light brown syrup which solidified on standing at 4° C. Its melting point, optical rotation, and $^1$H nmr spectrum were consistent with published data (Helv. Chim. Acta, 1946, 29, 1–8; Chem. Ber., 1975, 108, 1896–1901).

It is noted that an alternative synthesis of the title compound has been reported in Chem. Ber., 108 (1975) 1896–1901.

PREPARATIVE EXAMPLE 6

1,6-Anhydro-3-deoxy-2-O-methyl-β-D-ribo-hexopyranose

Methyl 4,6-O-benzylidene-3-deoxy-2-O-methyl-α-D-ribo-hexopyranoside (see Preparative Example 5, 18.0 g) in dry methanol (200 ml) was stirred with anhydrous p-toluenesulphonic acid (200 mg) at room temperature for 16 h. Anhydrous sodium carbonate (~1 g) was added. After stirring for 2 h, the solids were removed by filtration and the filtrate was evaporated to a brown syrup. Purification by flash chromatography gave methyl 3-deoxy-2-O-methyl-α-D-ribo-hexopyranoside (11.9 g, 97%) as a colourless oil. Its optical rotation and $^1$H nmr spectrum were consistent with published data (Chem. Ber. 1975, 108, 1896–1901).

A solution of this compound (9.6 g) in bis-(2-methoxyethyl) ether (100 ml) containing anhydrous p-toluenesulphonic acid (500 mg) was heated under reflux, while passing a stream of nitrogen through the condenser, for 1 h. The cooled solution was neutralised with triethylamine and evaporated at 50° C. and 1 torr to a dark brown oil. Purification by flash chromatography on silica gel gave the title compound (4.5 g, 57%), identical by melting point, optical rotation, $^1$H-nmr, and $^{13}$C-nmr to the compound described in Preparative Example 1.

PREPARATIVE EXAMPLE 7

Methyl 6-O-tert-butyldiphenylsilyl-3-deoxy-2-O-methyl-α-D-erythro-hexopyranosid-4-ulose A. Methyl 6-O-tert-butyldiphenylsilyl-3-deoxy-2-O-methyl-α-D-ribo-hexopyranoside A solution of methyl 4,6-O-benzylidene-3-deoxy-2-O-methyl-α-D-ribo-hexopyranoside (see Preparative Example 5) (22 g) in methanol (200 ml) containing p-toluenesulphonic acid (0.30 g) was stirred at ambient temperature for 6 h. The solution was neutralised with Amberlyst A26 basic resin, filtered, and the filtrate was concentrated to dryness. The residue was chromatographed on silica gel to remove the benzaldehyde dimethylacetal. The resulting diol (11 g) was dissolved in N,N-dimethylformamide (100 ml) and tert-butyldiphenylchlorosilane (16.5 g) and then imidazole (7.8 g) were added at room temperature. The resulting solution was stirred for 6 h, water was added and the mixture was extracted three times with chloroform. The combined extracts were washed with 2M aqueous hydrochloric acid, saturated aqueous sodium hydrogen carbonate, and twice with water. The chloroform solution was dried (MgSO$_4$), evaporated in vacuo, and the residue was chromatographed on silica gel to give the title compound A as a colourless syrup (22 g), $[\alpha]_D$ +40°; $^{13}$C-nmr data: 96.5 (C-1), 76.0, 71.4 and 67.9 (C-2, C-4 and C-5), 32.1 (C-3), 65.4 (C-6), 135.5, 132.8, 129.8 and 127.7 (aromatic), 56.5 and 54.7 (OCH$_3$), 26.8 (C(CH$_3$)$_3$), and 19.1 (C(CH$_3$)$_3$).

B. Methyl 6-O-tert-butyldiphenylsilyl-3-deoxy-2-O-methyl-α-D-erythro-hexopyranosid-4-ulose To a stirred solution of oxalyl chloride (6 ml) in dry dichloromethane (150 ml) at −70° C. under argon was added dropwise dimethylsulphoxide (10.5 ml) in dichloromethane (20 ml). Five minutes after the addition was complete a solution of the product of step A (22 g) in dichloromethane (100 ml) was added slowly at −70° C. and the resulting mixture was stirred in the cooling bath for 0.5 h. Triethylamine (45 ml) was added slowly and then the cooling bath was removed and the mixture was stirred and allowed to warm to ~0° C., before being washed with water, 2M aqueous hydrochloric acid, saturated aqueous sodium hydrogen carbonate and dried (MgSO$_4$). The solvent was removed in vacuo to give 21.2 g of title compound as a pale yellow oil. A portion purified by chromatography on silica gel had $[\alpha]_D$ +75.6°; $^{13}$C-nmr data: 96.8 (C-1), 76.2 and 75.5 (C-2 and C-5), 40.5 (C-3), 205.7 (C-4), 63.8 (C-6), 135.5, 133.1, 132.9, 129.7 and 127.6 (aromatic), 56.9 and 55.7 (OCH$_3$), 26.7 (C(CH$_3$)$_3$) and 19.2 (C(CH$_3$)$_3$).

PREPARATIVE EXAMPLE 8

4-O-Benzyl-3-deoxy-5,6-O-isopropylidene-2-O-methyl-aldehydo-D-ribo-hexose

A. 4-O-Benzyl-3-deoxy-5,6-O-isopropylidene-2-O-methyl-D-ribo-hexitol

4-O-Benzyl-3-deoxy-2-O-methyl-D-ribo-hexopyranose, prepared from 1,6-anhydro-4-O-benzyl-3-deoxy-2-O-methyl-β-D-ribo-hexopyranose (2.0 g) as described in Example 15, was reduced with sodium borohydride (0.3 g) in methanol (50 ml). After 1 h the solution was made slightly acidic with acetic acid, stirred with Amberlyst A-15, H$^+$-form ion-exchange resin (25 ml) for 1 h, filtered, and co-evaporated with methanol three times. The residue was dissolved in acetone (50 ml) and stirred with anhydrous copper (II) sulphate (5 g) and a catalytic amount of p-toluenesulphonic acid. After 1 h, the solution was poured into saturated aqueous bicarbonate, and extracted with chloroform (×3). The organic phase was dried (Na$_2$SO$_4$) and evaporated, and the resulting syrup was purified by flash chromatography on silica gel to yield the title compound A as a white crystalline solid (2.0 g, 80%). Recrystallised from ether/light petroleum ether, it had m.p. 44°–46° C.

B. 4-O-Benzyl-3-deoxy-5,6-O-isopropylidene-2-O-methylaldehydo-D-ribose

The crude product from part A, prior to chromatography, was subjected to "Swern oxidation" (Synthesis, 1981, 179) as follows: to a stirred solution of oxalyl chloride (1.0 ml) in dichloromethane (10 ml) at −70° C. was added dimethylsulphoxide (1.7 ml), then after 5 min a solution of the product from Part A in dichloromethane (5 ml). After 20 min triethylamine (10 ml) was added and the solution allowed to warm to 0°–10° C., after which it was washed in turn with water, dilute hydrochloric acid, and aqueous bicarbonate, then dried (Na$_2$SO$_4$), evaporated, and purified by flash chromatography on silica gel to give the title aldehyde as a pale yellow syrup (2.11 g, 85% from the 1,6-anhydride), $[\alpha]_D$ +22.4°; $^{13}$C-nmr data: 202.3 (C-1), 137.9 (q, aromatic), 128.2, 127.8, and 127.6 (aromatic), 109.1 (Me$_2$C), 82.4, 77.8, and 75.0 (C-2, C-4, and C-5), 72.5 (PhCH$_2$O), 66.1 (C-6), 57.9 (OCH$_3$), 32.3 (C-3), 26.4 and 25.9 (C—CH$_3$).

EXAMPLE 1

1,6-Anhydro-2,4-di-O-benzyl-3-O-methyl-β-D-glucopyranose

A solution of 1,6-anhydro-2,4-di-O-benzyl-β-D-glucopyranose (Chem Ber 70 (1937) 1848–1856) (1.5 g, 4.4 mmol) and a trace of tetrabutylammonium iodide in tetrahydrofuran (10 ml) was stirred with sodium hydride (60% dispersion in oil, 200 mg, 5 mmol). Methyl iodide (0.7 g, 5 mmol) was added. The reaction was complete almost immediately (t.l.c evidence). Ethanol was added to the reaction mixture to destroy excess sodium hydride. The mixture was diluted with chloroform and washed with water and brine. The organic phase was dried and evaporated and the residue was chromatographed on silica gel (hexane/ethyl acetate, 2:1) to give the title compound (1.7 g, 109%), as a colourless syrup that yellowed on standing $[\alpha]_D$ −33.5°. $^{13}$C Nmr peaks were recorded at 100.5 (C-1), 76.6 (C-2), 79.0 (C-3), 76.1 (C-4), 74.3 (C-5), 65.3 (C-6), 71.9 and 71.2 (PhCH$_2$O), 58.0 (OCH$_3$), and 138.0, 137.9, 128.4, 127.9 and 127.8 (aromatic).

It is noted that an alternative synthesis of 1,6-anhydro-2,4-di-O-benzyl-3-O-methyl-β-D-glucopyranose has been reported in J. Am. Chem. Soc., 71 (1949) 2116–2119.

EXAMPLE 2

1,6-Anhydro-4-O-benzyl-3-deoxy-β-D-erythro-hexopyranos-2-ulose dibenzyl acetal and 1,6-Anhydro-4-O-benzyl-3-deoxy-β-D-ribo-hexopyranose Benzyl alcohol (62.5 ml) was stirred vigorously while concentrated sulphuric acid (0.25 g) was added dropwise, and then after 1–2 h, levoglucosenone (25 g) (Carbohydr. Res. 71 (1979) 169–191) was added and the resulting mixture was stirred at room temperature for 2 days. Chloroform (300 ml) was added and the solution was washed with saturated aqueous sodium hydrogen carbonate (300 ml), water (300 ml), and dried (MgSO$_4$) and then the chloroform was removed under vacuum. The residue was dissolved in ethanol (100 ml) and added to a stirred freshly prepared solution of sodium borohydride (16 g) in ethanol (400 ml). After 2 h the solution was carefully made slightly acidic (pH 5–6) with acetic acid and then the ethanol was stripped under vacuum. Ethyl acetate (200 ml) was added to the residue and then filtered through a pad of silica gel (10 cm×4 cm) which was washed with a further 200 ml of ethyl acetate. The combined filtrates were concentrated to a thick liquid and then the benzyl alcohol was distilled off under high vacuum (~1 mm Hg oil bath ~120° C.) to give a dark yellow syrup (39 g). Preparative HPLC [eluant ethyl acetate/light petroleum 1:4 and then 1:3, 1:2, 1:1 (v/v) followed by ethyl acetate] gave in order of elution the first title compound (10.2 g), crystalline from ether/light petroleum, the second title compound (10.1 g), syrup, and its corresponding D-arabino isomer (11.8 g), crystalline from ethyl acetate/light petroleum. The first title compound had the following $^{13}$C-nmr data: 100.2 (C-1), 97.8 (C-2), 30.0 (C-3), 73.4 (C-4), 74.8 (C-5), 66.0 (C-6), 70.6, 63.9 and 62.7 (PhCH$_2$O), 138.3, 128.4, 127.7, 127.6, and 127.4 (aromatic). The D-arabino isomer was isolated and saved for use in Preparative Example 3 and Example 9. The second title compound was crystallised and recrystallised from ether/light petroleum.

The characteristics of the second title compound and its D-arabino isomer are given in Example 14A.

EXAMPLE 3

2-O-Alkylations

To a stirred solution of 1,6-anhydro-4-O-benzyl-3-deoxy-$\beta$-D-ribo-hexopyranose (Izv. Akad. Nauk. SSSR, Ser. Khim, (1975) 128-131; see second title compound of Example 2) in dry tetrahydrofuran (10 ml/g of carbohydrate alcohol) at 0° C., sodium hydride (60% or 80% dispersion in oil, 1.1 eq) was added slowly. When effervescence had ceased the appropriate alkyl halide (1.1 eq) was added portionwise and the resulting mixture was stirred at 0° C. for 2 hours and then at room temperature if necessary until the reaction was complete. Catalytic amounts of tetrabutyl-ammonium iodide were added in some cases where reaction was slow. Ether or preferably chloroform (20 ml/g) was added and the mixture was washed with water (30 ml/g). The aqueous phase was back extracted with ether or preferably chloroform (5 ml/g) and combined organic extracts were dried (MgSO$_4$) before being concentrated to a thick syrup. Purification was effected by flash chromatography on silica gel. Using the appropriate alkyl halide, the following compounds were prepared:

1. 1,6-anhydro-4-O-benzyl-3-deoxy-2-O-methyl-$\beta$-D-ribo-hexopyranose, $[\alpha]_D$ −39.9°; $^{13}$C-nmr data: 100.2 (C-1), 74.8 and 74.7 (C-2 and C-5), 24.4 (C-3), 71.8 (C-4), 65.5 (C-6), 70.4 (PhCH$_2$O), 57.3 (OCH$_3$), 138.2, 128.3, 127.6 and 127.5 (aromatic).

The 2-O-alkylation technique has also been used to prepare the enantiomer of this compound (see Example 11).

2. 1,6-anhydro-4-O-benzyl-3-deoxy-2-O-ethyl-$\beta$-D-ribo-hexopyranose, $[\alpha]_D$ −30.8°; $^{13}$C-nmr data: 100.9 (C-1), 73.0 (C-2), 24.6 (C-3), 72.0 (C-4), 74.8 (C-5), 65.5 (C-6), 70.3 (PhCH$_2$O), 65.0 (OCH$_2$CH$_3$), 15.0 (OCH$_2$CH$_3$), 138.4, 128.4, 127.6, and 127.5 (aromatic).

3. 1,6-anhydro-4-O-benzyl-3-deoxy-2-O-n-butyl-$\beta$-D-ribo-hexopyranose, $[\alpha]_D$ −40.4°; $^{13}$C-nmr data: 100.9 (C-1), 73.2 (C-2), 24.5 (C-3), 72.1 (C-4), 74.8 (C-5), 65.5 (C-6), .70.3 and 69.6 (PhCH$_2$O and OCH$_2$Pr), 31.9 and 19.3 (CH$_2$), 13.9 (C-CH$_3$), 138.5, 128.3, 127.6, and 127.5 (aromatic).

4. 1,6-anhydro-2,4-di-O-benzyl-3-deoxy-$\beta$-D-ribo-hexopyranose, m.p. 60°-61° C., $[\alpha]_D$ −49.7°; $^{13}$C-nmr data: 100.8 (C-1), 72.0 (C-2), 24.5 (C-3), 72.0 (C-4), 74.6 (C-5), 65.4 (C-6), 71.2 and 70.3 (PhCH$_2$O), 138.3, 128.3, 127.7, 127.6 and 127.5 (aromatic).

It is noted that an alternative synthesis of 1,6-anhydro-2,4-di-O-benzyl-3-deoxy-$\beta$-D-glucopyranose is reported in Macromolecules 16 (1983) 710-711.

5. 1,6-anhydro-4-O-benzyl-3-deoxy-2-O-(3-trifluoromethylbenzyl)-$\beta$-D-ribo-hexopyranose, $[\alpha]_D$ −30.1°; $^{13}$C-nmr data: 100.5 (C-1), 72.7, 71.9 and 70.5 (C-2, C-4 and ArCH$_2$O), 24.7 (C-3), and 74.6 (C-5).

6. 2-O-allyl-1,6-anhydro-4-O-benzyl-3-deoxy-$\beta$-D-ribo-hexopyranose, $[\alpha]_D$ −39.6°; $^{13}$C-nmr data: 100.6 (C-1), 72.0 and 71.8 (C-2 and C-4), 24.6 (C-3), 74.6 (C-5), 65.3 (C-6), 70.5 and 70.2 (ArCH$_2$O and CH$_2$=CHCH$_2$O), 117.0 (=CH$_2$), 134.9 (OCH$_2$—CH=CH$_2$), 128.3, 127.6 and 127.5 (aromatic).

7. 1,6-anhydro-4-O-benzyl-3-deoxy-2-C-ethyl-2-O-methyl-$\beta$-D-ribo-hexopyranose, prepared from the first title compound of Example 17, m.p. 40°-43° C., $[\alpha]_D$ −25.7°; $^{13}$C-nmr data: 102.2 (C-1), 74.3 (C-2), 27.9 (C-3), 72.4 (C-4), 74.2 (C-5), 65.6 (C-6), 70.4 (ArCH$_2$O), 138.3, 128.3 and 127.5 (aromatic), 49.7 (OCH$_3$), 25.5 (CH$_2$CH$_3$), and 6.0 (CH$_2$CH$_3$).

8. 1,6-anhydro-4-O-benzyl-3-deoxy-2-C-methyl-2-O-methyl-$\beta$-D-ribo-hexopyranose, prepared from the first title compound of Example 8, $[\alpha]_D$ −36.6°; $^{13}$C-nmr data: 104.2 (C-1), 73.2 (C-2), 27.9 (C-3), 72.2 (C-4), 74.0 (C-5), 65.6 (C-6), 70.5 (ArCH$_2$O), 128.3, 127.5 (aromatic), 50.0 (OCH$_3$), and 20.6 (C-CH$_3$).

9. 1,6-anhydro-4-O-benzyl-3-deoxy-2-C-ethyl-2-O-methyl-$\beta$-D-arabino-hexopyranose, prepared from the second title compound of Example 17, $[\alpha]_D$ −51.1°; $^{13}$C-nmr data: 102.5 (C-1), 75.7 (C-2), 30.5 and 23.9 (C-3 and CH$_2$CH$_3$), 74.2 (C-4), 75.1 (C-5), 66.1 (C-6), 70.5 (ArCH$_2$O), 128.4, 127.6 and 127.3 (aromatic), 48.5 (OCH$_3$), and 6.8 (CH$_2$CH$_3$).

10. 1,6-anhydro-4-O-benzyl-3-deoxy-2-O-propargyl-$\beta$-D-ribo-hexopyranose, $[\alpha]_D$ −64.0°; $^{13}$C-nmr data: 100.4 (C-1), 71.6 and 71.4 (C-2 and C-4), 24.3 (C-3), 74.5 (C-5), 65.4 (C-6), 70.3 (PhCH$_2$O), 56.4 (OCH$_3$), 56.4 (HC≡CCH$_2$O), 138.2 (q-aromatic), 128.3 and 127.6 (aromatic).

11. 1,6-anhydro-4-O-benzyl-3-deoxy-2-O-n-propyl-$\beta$-D-ribo-hexopyranose, $[\alpha]_D$ −30.2°; $^{13}$C-nmr data: 100.8 (C-1), 74.7 and 73.1 (C-2 and C-5), 24.4 (C-3), 71.9 (C-4), 65.4 (C-6), 71.4 and 70.2 (PhCH$_2$O and EtCH$_2$O), 23.0 (MeCH$_2$CH$_2$O), 10.5 (C-Me), 138.3 (q-aromatic), 128.3 (×2), 127.5 (×2), and 127.4 (aromatic).

12. 1,6-anhydro-4-O-benzyl-3-deoxy-2-O-(2-methoxyethoxy)-$\beta$-D-ribo-hexopyranose, $[\alpha]_D$ −26.1°; $^{13}$C-nmr data: 100.6 (C-1), 74.7 and 73.6 (C-2 and C-5), 24.3 (C-3), 71.8 (C-4), 65.3 (C-6), 72.1, 70.2 and 68.6 (RCH$_2$O), 56.9 (OCH$_3$), 138.2 (q-aromatic), 128.2 (×2), 127.5 (×2), and 127.4 (aromatic).

EXAMPLE 4

4-O-Aralkylations

Using a method analogous to Example 3, but starting from 1,6-anhydro-3-deoxy-2-O-methyl-$\beta$-D-ribo-hexopyranose (see Preparative Example 1) and an appropriate aralkyl halide as starting materials, the following compounds were prepared:

1. 1,6-anhydro-3-deoxy-4-O-(2,6-dichlorobenzyl)-2-O-methyl-$\beta$-D-ribo-hexopyranose, m.p. 54°-55° C., $[\alpha]_D$ −34.9°; $^{13}$C-nmr data: 100.3 (C-1), 75.0 and 74.5 (C-2 and C-5), 23.6 (C-3), 72.4 (C-4), 65.5 and 65.2 (C-6 and ArCH$_2$O), 137.0, 133.2, 129.8 and 128.3 (aromatic), and 57.1 (OCH$_3$).

2. 1,6-anhydro-3-deoxy-4-O-(2,4-dichlorobenzyl)-2-O-methyl-$\beta$-D-ribo-hexopyranose, $[\alpha]_D$ −45.1°; $^{13}$C-nmr data: 100.2 (C-1), 74.5 and 74.3 (C-2 and C-5), 24.4 (C-3), 73.4 (C-4), 65.3 (C-6), 67.1 (ArCH$_2$O), 57.3 (OCH$_3$), 134.7, 133.4, 132.9, 129.9, 128.7 and 127.1 (aromatic).

3. 1,6-anhydro-3-deoxy-2-O-methyl-4-O-($\alpha$-methylbenzyl)-$\beta$-D-ribo-hexopyranose, $[\alpha]_D$ −24.2°; $^{13}$C-nmr data on mixture of diastereoisomers; 100.4 and 99.9 (C-1), 76.4, 76.3, 75.8, 74.7 and 73.9 (C-2, C-5. and PhMeCH), 25.4 and 22.9 (C-3), 70.9 and 70.2 (C-4), 65.4 (C-6), 57.1 (OCH$_3$), 24.8 and 24.6 (PhCHCH$_3$).

4. 1,6-anhydro-4-O-(2-chlorobenzyl)-3-deoxy-2-O-methyl-β-D-ribo-hexopyranose, $[\alpha]_D$ −42.3°; $^{13}$C-nmr data: 100.2 (C-1), 74.6 and 74.4 (C-2 and C-5), 24.3 (C-3), 73.0 (C-4), 65.4 (C-6), 67.5 (ArCH$_2$O), 135.9, 129.1, 128.9, 128.5 and 126.8 (aromatic), and 57.3 (OCH$_3$).

5. 1,6-anhydro-3-deoxy-2-O-methyl-4-O-(2-methylbenzyl)-β-D-ribo-hexopyranose, $[\alpha]_D$ −33.4°; $^{13}$C-nmr data: 100.2 (C-1), 74.6 (C-2), 24.0 (C-3), 71.7 (C-4), 74.6 (C-5), 65.4 (C-6), 68.8 (ArCH$_2$O), 136.6, 135.9, 130.2, 128.6, 127.7 and 125.6 (aromatic), 57.2 (OCH$_3$), and 18.9 (ArCH$_3$).

6. 1,6-anhydro-3-deoxy-4-O-(2-fluorobenzyl)-2-O-methyl-β-D-ribo-hexopyranose, $[\alpha]_D$ −43.4°; $^{13}$C-nmr data: 100.1 (C-1), 74.5 and 74.4 (C-2 and C-5), 24.1 (C-3), 72.5 (C-4), 65.3 (C-6), 63.7 (ArCH$_2$O), 160.5, 130.0, 129.1, 125.3, 124.1 and 114.8 (aromatic), and 57.2 (OCH$_3$). The aromatic and benzylic resonances were all doublets exhibiting coupling with the fluorine.

7. 1,6-anhydro-3-deoxy-2-O-methyl-4-O-(4-methylbenzyl)-β-D-ribo-hexopyranose, $[\alpha]_D$ −32.0°; $^{13}$C-nmr data: 100.1 (C-1), 74.6 and 74.5 (C-2 and C-5), 24.1 (C-3), 71.4 (C-4), 65.3 (C-6), 70.1 (ArCH$_2$O), 21.0 (Ar-Me), 128.9, 128.8 and 127.7 (aromatic), and 57.2 (OCH$_3$).

8. 1,6-anhydro-3-deoxy-2-O-methyl-4-O-(3-trifluoromethylbenzyl)-β-D-ribo-hexopyranose, $[\alpha]_D$ −37.5°; $^{13}$C-nmr data: 100.1 (C-1), 74.5 and 74.4 (C-2 and C-5), 24.3 (C-3), 72.7 (C-4), 65.3 (C-6), 69.7 (ArCH$_2$O), and 57.2 (OCH$_3$).

9. 1,6-anhydro-4-O-(4-bromobenzyl)-3-deoxy-2-O-methyl-β-D-ribo-hexopyranose, $[\alpha]_D$ −33.2°; $^{13}$C-nmr data: 100.0 (C-1), 74.5 and 74.4 (C-2 and C-5), 24.2 (C-3), 72.2 (C-4), 65.3 (C-6), 69.6 (ArCH$_2$O), 137.3, 131.3, 129.1 and 121.2 (aromatic), and 57.2 (OCH$_3$).

10. 1,6-anhydro-3-deoxy-2-O-methyl-4-O-(2,4,6-trimethylbenzyl)-β-D-ribo-hexopyranose, m.p. 54°–56° C., $[\alpha]_D$ −33.8°; $^{13}$C-nmr data: 100.1 (C-1), 75.2 and 74.7 (C-2 and C-5), 23.9 (C-3), 71.4 (C-4), 65.5 (C-6), 64.4 (ArCH$_2$O), 137.9, 137.4, 131.0 and 128.9 (aromatic), 57.2 (OCH$_3$), 20.9 and 19.7 (ArCH$_3$).

11. 1,6-anhydro-3-deoxy-2-O-methyl-4-O-(4-tert-butylbenzyl)-β-D-ribo-hexopyranose, m.p. 50°–53° C., $[\alpha]_D$ −30.0°; $^{13}$C-nmr data: 100.1 (C-1), 74.7 and 74.6 (C-2 and C-5), 24.2 (C-3), 71.4 (C-4), 65.4 (C-6), 70.0 (ArCH$_2$O), 150.4, 135.2, 127.4 and 125.2 (aromatic), 57.3 (OCH$_3$), 34.4 (ArC(CH$_3$)$_3$), and 31.3 (ArC(CH$_3$)$_3$).

12. 1,6-anhydro-3-deoxy-4-O-(4-methoxybenzyl)-2-O-methyl-β-D-ribo-hexopyranose, $[\alpha]_D$ −31.2°; $^{13}$C-nmr data: 100.1 (C-1), 74.7 (C-2 and C-5), 24.2 (C-3), 71.2 (C-4), 65.4 (C-6), 69.9 (ArCH$_2$O), 130.3, 129.1 and 113.7 (aromatic), 57.3 (OCH$_3$) and 55.1 (ArOCH$_3$).

13. 1,6-anhydro-3-deoxy-4-O-(2-methoxy-6-nitrobenzyl)-2-O-methyl-β-D-ribo-hexopyranose, m.p. 74.5°–76° C., $[\alpha]_D$ −29.0°, $^{13}$C-nmr data: 100.2 (C-1), 74.5 and 74.2 (C-2 and C-5), 24.5 (C-3), 73.6 (C-4), 65.3 (C-6), 64.5 (ArCH$_2$O), 161.2, 128.3, 124.5, 123.8 and 109.5 (aromatic), 57.2 (OCH$_3$), and 56.0 (ArOCH$_3$).

14. 1,6-anhydro-4-O-(4-cyanobenzyl)-3-deoxy-2-O-methyl-β-D-ribo-hexopyranose, m.p. 85°–86° C.; $[\alpha]_D$ −53.3°; $^{13}$C-nmr data: 100.1 (C-1), 74.5 and 74.3 (C-2 and C-5), 24.4 (C-3), 73.1 (C-4), 65.3 (C-6), 69.6 (ArCH$_2$O), 144.0 and 111.1 (q-aromatic), 132.1 and 127.7 (aromatic), and 57.3 (OCH$_3$).

15. 1,6-anhydro-3-deoxy-2-O-methyl-4-O-(2-trifluoromethylbenzyl)-β-D-ribo-hexopyranose, $[\alpha]_D$ −44.3°; $^{13}$C-nmr data: 100.2 (C-1), 74.6 and 74.4 (C-2 and C-5), 24.1 (C-3), 73.1 (C-4), 65.3 (C-6), 66.3 (quartet, ArCH$_2$O), 131.9, 128.9, 127.1 and 125.3 (quartet, 5.6 Hz) (aromatic), and 57.2 (OCH$_3$).

16. 1,6-anhydro-3-deoxy-4-O-(2-fluoro-3-methylbenzyl)-2-O-methyl-β-D-ribo-hexopyranose, $[\alpha]_D$ −41.8°; $^{13}$C-nmr data: 100.2 (C-1), 74.5 and 74.5 (C-2 and C-5), 24.1 (C-3), 72.3 (C-4), 65.3 (C-6), 63.9 (ArCH$_2$O), 130.6, 127.4 and 123.5 (aromatic), 57.2 (OCH$_3$), and 14.3 (ArCH$_3$).

The aromatic and benzylic carbon resonances were doublets exhibiting coupling with the fluorine.

17. 1,6-anhydro-3-deoxy-4-O-(3,5-dimethylbenzyl)-2-O-methyl-β-D-ribo-hexopyranose, $[\alpha]_D$ −33.5°; $^{13}$C-nmr data: 100.1 (C-1), 74.7 (C-2 and C-5), 24.2 (C-3), 71.4 (C-4), 65.4 (C-6), 70.3 (ArCH$_2$O), 138.1, 137.8, 129.2 and 125.5 (aromatic), 57.3 (OCH$_3$), and 21.2 (ArCH$_3$).

18. 1,6-anhydro-3-deoxy-4-O-(2-methoxybenzyl)-2-O-methyl-β-D-ribo-hexopyranose, $[\alpha]_D$ −40.9°; $^{13}$C-nmr data: 100.2 (C-1), 74.7 and 74.6 (C-2 and C-5), 24.4 (C-3), 72.3 (C-4), 65.4 (C-6), 64.9 (ArCH$_2$O), 128.7, 128.3, 126.7, 120.5 and 109.9 (aromatic), 57.2 (OCH$_3$), and 55.2 (ArOCH$_3$).

19. 1,6-anhydro-3-deoxy-2-O-methyl-4-O-(4-methylthiobenzyl)-β-D-ribo-hexopyranose, $[\alpha]_D$ −30.0°; $^{13}$C-nmr data: 100.1 (C-1), 74.6 and 74.5 (C-2 and C-5), 24.3 (C-3), 71.6 (C-4), 65.3 (C-6), 69.9 (ArCH$_2$O), 135.1, 128.2 and 126.6 (aromatic), 57.3 (OCH$_3$), and 15.8 (ArSCH$_3$).

20. 1,6-anhydro-3-deoxy-4-O-(2-ethoxybenzyl)-2-O-methyl-β-D-ribo-hexopyranose, $[\alpha]_D$ −36.8°; $^{13}$C-nmr data: 100.2 (C-1), 74.7 and 74.6 (C-2 and C-5), 24.5 (C-3), 72.1 (C-4), 65.4 (C-6), 64.8 and 63.4 (ArCH$_2$O and OCH$_2$CH$_3$), 156.3, 129.0, 128.3, 126.8, 120.4 and 110.9 (aromatic), 57.2 (OCH$_3$), and 14.8 (OCH$_2$CH$_3$).

21. 1,6-anhydro-3-deoxy-2-O-methyl-4-O-(3-methylbenzyl)-β-D-ribo-hexopyranose, $[\alpha]_D$ −36.5°; $^{13}$C-nmr data: 100.0 (C-1), 74.6 and 74.5 (C-2 and C-5), 24.0 (C-3), 71.6 (C-4), 65.3 (C-6), 70.2 (ArCH$_2$O), 138.2, 137.7, 128.3, 128.1 and 124.6 (aromatic), 57.1 (OCH$_3$) and 21.2 (ArCH$_3$).

22. 1,6-anhydro-3-deoxy-4-O-(3-methoxybenzyl)-2-O-methyl-β-D-ribo-hexopyranose, $[\alpha]_D$ −33.1°; $^{13}$C-nmr data: 100.0 (C-1), 74.5 and 74.4 (C-2 and C-5), 24.1 (C-3), 71.7 (C-4), 65.2 (C-6), 70.0 (ArCH$_2$O), 159.6, 139.9, 129.2, 119.6, 112.9 and 112.8 (aromatic), 57.0 (OCH$_3$), and 54.9 (Ar OCH$_3$).

23. 1,6-anhydro-3-deoxy-4-O-(3-fluorobenzyl)-2-O-methyl-β-D-ribo-hexopyranose, $[\alpha]_D$ −41.5°; $^{13}$C-nmr data: 100.0 (C-1), 74.5 and 74.4 (C-2 and C-5), 24.0 (C-3), 72.3 (C-4), 65.2 (C-6), 69.5 (d, 1.9 Hz, ArCH$_2$O), 163.1 (d, 248 Hz), 141.3 (quat, d), 129.7 (d, 8.2 Hz), 122.7, (d, 3.1 Hz), 114.6 and 113.5 (d, 1.4 Hz) (aromatic), and 57.1 (OCH$_3$).

24. 1,6-anhydro-3-deoxy-4-O-(2,6-difluorobenzyl)-2-O-methyl-β-D-ribo-hexopyranose, $[\alpha]_D$ −39.1°; $^{13}$C-nmr data: 100.1 (C-1), 74.6 and 74.4 (C-2 and C-5), 23.3 (C-3), 72.2 (C-4), 65.2 (C-6), 57.6 (ArCH$_2$O, t, 3.2 and 3.2 Hz), 56.8 (OCH$_3$), 161.8 (dd, 255 and 8.3 Hz), 130.1 (t, 10.4 and 10.4 Hz), and 110.0 (m, AXY, aromatic).

25. 1,6-anhydro-3-deoxy-2-O-methyl-4-O-(2-naphthalenemethyl)-β-D-ribo-hexopyranose, [α]$_D$ −22.4°; $^{13}$C-nmr data: 100.1 (C-1), 74.7 and 74.6 (C-2 and C-5), 24.3 (C-3), 71.7 (C-4), 65.3 (C-6), 70.5 (ArCH$_2$O), 57.3 (OCH$_3$), 135.8, 133.1, 132.9 (q-aromatic), 128.1, 127.7, 127.6, 126.3, 126.1, 125.8 and 125.7 (aromatic).

26. 1,6-anhydro-3-deoxy-2-O-methyl-4-O-(1-naphthalenemethyl)-β-D-ribo-hexopyranose, [α]$_D$ −17.8°; $^{13}$C-nmr data: 100.1 (C-1), 74.7 (C-2 and C-5), 23.8 (C-3), 71.1 (C-4), 65.3 (C-6), 68.9 (ArCH$_2$O), 57.3 (OCH$_3$), 133.7, 133.4, 131.8 (q-aromatic), 128.6, 128.4, 126.6, 126.1, 125.8, 125.0 and 124.4 (aromatic).

27. 1,6-anhydro-4-O-[3-(benzyloxy)-benzyl]-3-deoxy-2-O-methyl-β-D-ribo-hexopyranose, m.p. 79°–81° C.; [α]$_D$ −21.9°; $^{13}$C-nmr data: 100.1 (C-1), 74.64 and 74.56 (C-2 and C-5), 24.3 (C-3), 71.5 (C-4), 65.4 (C-6), 70.1 and 69.8 (ArCH$_2$O), 57.3 (OCH$_3$), 158.9, 139.9, and 136.8 (q-aromatic), 129.4, 128.5 (×2), 127.8, 127.3 (×2), 120.1, 114.2. and 113.9 (aromatic).

28. 1,6-anhydro-3-deoxy-2-O-methyl-4-O-[1-(2-methylnaphthalenemethyl]-β-D-ribo-hexopyranose, m.p. 100°–103° C., [α]$_D$ −7.9°; $^{13}$C-nmr data: 100.1 (C-1), 75.2 and 74.7 (C-2 and C-5), 23.8 (C-3), 71.0 (C-4), 65.4 (C-6), 63.5 (ArCH$_2$O), 57.3 (OCH$_3$), 20.1 (C-CH$_3$), 135.4, 133.1, 132.4, and 130.2 (q-aromatic), 128.9, 128.4, 128.1, 126.2, 124.8, and 124.4 (aromatic)

29. 1,6-anhydro-3-deoxy-2-O-methyl-4-O-(2-picolyl)-β-D-ribo-hexopyranose, m.p. 42°–47° C., [α]$_D$ −59.3°; $^{13}$C-nmr data: 100.0 (C-1), 74.5 and 74.2 (C-2 and C-5), 24.2 (C-3), 71.5 (C-4), 65.2 (C-6), 73.0 (ArCH$_2$O), 57.2 (OMe), 158.5 (q-aromatic), 148.5, 136.5, 122.2, and 121.5 (aromatic).

30. 1,6-anhydro-3-deoxy-2-O-methyl-4-O-(3-picolyl)-β-D-ribo-hexopyranose, [α]$_D$ −46.4°; $^{13}$C-nmr data: 100.0 (C-1), 74.5 and 74.4 (C-2 and C-5), 24.2 (C-3), 72.6 (C-4), 65.3 (C-6), 68.0 (ArCH$_2$O), 57.2 (OMe), 148.9, 148.8, 135.3, and 123.1 (aromatic).

31. 1,6-anhydro-3-deoxy-2-O-methyl-4-O-(4-picolyl)-β-D-ribo-hexopyranose, [α]$_D$ −49.5°; $^{13}$C-nmr data: 99.8 (C-1), 74.2 and 73.9 (C-2 and C-5), 23.8 (C-3), 72.9 (C-4), 64.9 (C-6), 68.4 (ArCH$_2$O), 56.8 (OCH$_3$), 147.5 (q-aromatic), 149.2 (×2), and 121.4 (×2, aromatic).

32. 1,6-anhydro-3-deoxy-2-O-methyl-4-O-(2-thiophenemethyl)-β-D-ribo-hexopyranose, [α]$_D$ −30.2°; $^{13}$C-nmr data: 100.0 (C-1), 74.5 (C-2 and C-5), 24.1 (C-3), 71.0 (C-4), 65.2 and 64.7 (C-6 and ArCH$_2$O), 57.1 (OCH$_3$), 141.2 (q-aromatic), 126.5, 126.3, and 125.7 (aromatic).

33. 1,6-anhydro-3-deoxy-2-O-methyl-4-O-(3-thiophenemethyl)-β-D-ribo-hexopyranose, [α]$_D$ −38.4°; $^{13}$C-nmr data: 99.9 (C-1), 74.5 and 74.4 (C-2 and C-5), 24.1 (C-3), 71.6 (C-4), 65.6 and 65.2 (C-6 and ArCH$_2$O), 57.0 (OCH$_3$), 139.4 (q-aromatic), 127.2, 125.8, and 122.4 (aromatic).

34. 1,6-anhydro-3-deoxy-4-O-(2,5-dichlorobenzyl)-2-O-methyl-β-D-ribo-hexopyranose, m.p. 63°–64° C., [α]$_D$ −46.8°; $^{13}$C-nmr data: 100.2 (C-1), 74.5 and 74.3 (C-2 and C-5), 24.5 (C-3), 73.6 (C-4), 65.3 (C-6), 67.2 (ArCH$_2$O), 57.3 (OCH$_3$), 137.9 and 132.8 (q-aromatic), 129.9, 128.8, and 128.3 (aromatic).

35. 1,6-anhydro-3-deoxy-4-O-(2,5-dimethylbenzyl)-2-O-methyl-β-D-ribo-hexopyranose, m.p. 88°–89° C., [α]$_D$ −40.0°; $^{13}$C-nmr data: 100.1 (C-1), 74.7 (C-2 and C-5), 24.0 (C-3), 71.8 (C-4), 65.4 (C-6), 68.6 (ArCH$_2$O), 57.2 (OCH$_3$), 135.6, 134.9 and 133.7 (q-aromatic), 130.1, 129.5 and 128.3 (aromatic), 18.4 and 20.7 (C-CH$_3$).

36. 1,6-anhydro-3-deoxy-4-O-(2,3-dichlorobenzyl)-2-O-methyl-β-D-ribo-hexopyranose, [α]$_D$ −46.3°; $^{13}$C-nmr data: 100.2 (C-1), 74.5 and 74.3 (C-2 and C-5), 24.3 (C-3), 73.5 (C-4), 65.3 (C-6), 68.0 (ArCH$_2$O), 57.3 (OCH$_3$), 138.4 (q-aromatic), 129.0, 127.3, and 126.9 (aromatic).

37. 1,2-bis[(1,6-anhydro-3-deoxy-2-O-methyl-β-D-ribohexopyranose-4-O-yl)methyl]benzene, m.p. 143°–147° C., [α]$_D$ −65.8°; $^{13}$C-nmr data: 100.0 (C-1), 74.5 and 74.3 (C-2 and C-5), 24.0 (C-3), 72.1 (C-4), 65.2 (C-6), 68.1 (ArCH$_2$O), 57.0 (OCH$_3$), 136.4 (q-aromatic), 128.5 and 127.4 (aromatic).

38. 1,6-anhydro-3-deoxy-2-O-methyl-4-O-(2,3,4,5,6-pentamethylbenzyl)-β-D-ribo-hexopyranose, m.p. 111°–112° C., [α]$_D$ −34.2°; $^{13}$C-nmr data: 100.3 (C-1), 75.3 and 74.8 (C-2 and C-5), 24.0 (C-3), 71.6 (C-4), 65.6 and 65.4 (C-6 and ArCH$_2$O), 57.2 (OMe), 17.0, 16.6 (×2) and 16.4 (×2, ArCH$_3$), 134.8, 133.7, 132.3 and 131.2 (aromatic).

39. 1,6-anhydro-4-O-(2-bromobenzyl)-3-deoxy-2-O-methyl-β-D-ribo-hexopyranose, [α]$_D$ −42.6°; $^{13}$C-nmr data: 100.2 (C-1), 74.6 and 74.4 (C-2 and C-5), 24.3 (C-3), 73.0 (C-4), 65.8 (C-6), 69.9 (ArCH$_2$O), 57.3 (OCH$_3$), 137.5 and 122.3 (q-aromatic), 132.2, 129.2, 128.8, and 127.4 (aromatic)

40. 1,6-anhydro-3-deoxy-4-O-(2-iodobenzyl)-2-O-methyl-β-D-ribo-hexopyranose, m.p. 47°–47.5° C., [α]$_D$ −36.9°; $^{13}$C-nmr data: 100.2 (C-1), 74.6 and 74.4 (C-2 and C-5), 24.4 (C-3), 73.0 (C-4), 65.4 (C-6), 74.4 (ArCH$_2$O), 57.3 (OCH$_3$), 140.3 and 100.2 (q-aromatic), 138.8, 129.1, 128.9 and 128.2 (aromatic)

41. 1,6-anhydro-4-O-(2-cyanobenzyl)-3-deoxy-2-O-methyl-β-D-ribo-hexopyranose, m.p. 77°–78° C., [α]$_D$ −54.3°; $^{13}$C-nmr data: 100.1 (C-1), 74.5 and 74.3 (C-2 and C-5), 24.1 (C-3), 73.9 (C-4), 65.3 (C-6), 68.5 (ArCH$_2$O), 57.3 (OCH$_3$), 141.9 and 111.7 (q-aromatic), 132.8, 132.4, 128.7 and 127.9 (aromatic), and 117.3 (CN).

42. 1,6-anhydro-4-O-(3-chlorobenzyl)-3-deoxy-2-O-methyl-β-D-ribo-hexopyranose, [α]$_D$ −37.6°; $^{13}$C-nmr data: 100.1 (C-1), 74.51 and 74.46 (C-2 and C-5), 24.2 (C-3), 72.3 (C-4), 65.3 (C-6), 69.6 (ArCH$_2$O), 57.3 (OCH$_3$), 140.4 and 134.1 (q-aromatic), 129.6, 127.53, 127.46 and 125.5 (aromatic).

43. 1,6-anhydro-4-O-(3-cyanobenzyl)-3-deoxy-2-O-methyl-β-D-ribo-hexopyranose, [α]$_D$ −47.0°; $^{13}$C-nmr data: 100.1 (C-1), 74.5 and 74.3 (C-2 and C-5), 24.3 (C-3), 73.0 (C-4), 65.3 (C-6), 69.3 (ArCH$_2$O), 57.3 (OCH$_3$), 140.0 and 112.2 (q-aromatic), 131.5, 130.9, 130.7 and 129.0 (aromatic).

44. 1,6-anhydro-3-deoxy-4-O-(4-fluorobenzyl)-2-O-methyl-β-D-ribo-hexopyranose, [α]$_D$ −41.3°; $^{13}$C-nmr data: 100.1 (C-1), 74.6 and 74.5 (C-2 and C-5), 24.2 (C-3), 72.0 (C-4), 65.3 (C-6), 57.9 (t, 2.2 Hz, ArCH$_2$O), 133.9 (q-aromatic), 129.2 (d, 8.1 Hz), 115.0 (d, 21.4 Hz, aromatic).

45. 1,6-anhydro-4-O-(4-chlorobenzyl)-3-deoxy-2-O-methyl-β-D-ribo-hexopyranose, m.p. 48°–49° C., [α]$_D$ −39.9°; $^{13}$C-nmr data: 100.1 (C-1), 74.53 and 74.45 (C-2 and C-5), 24.2 (C-3), 72.1 (C-4), 65.3 (C-6), 69.6 (ArCH$_2$O), 57.3 (OCH$_3$), 136.1 and 133.1 (q-aromatic), 128.6 and 128.4 (aromatic).

46. 1,6-anhydro-3-deoxy-2-O-methyl-4-O-(4-trifluoromethylbenzyl)-β-D-ribo-hexopyranose, [α]$_D$ −40.8°; $^{13}$C-nmr data: 100.1 (C-1), 74.5 and 74.4 (C-2 and C-5), 24.2 (C-3), 72.6 (C-4), 65.3 (C-6), 69.6 (ArC H₂O), 57.1 (OCH₃), 142, 127.4 (×2), 125.2, 125.0 and 124.8 (aromatic).
47. 1,6-anhydro-4-O-(4-benzyloxybenzyl)-3-deoxy-2-O-methyl-β-D-ribo-hexopyranose, m.p. 72°–73° C., $[\alpha]_D$ −22.6°; $^{13}$C-nmr data: 100.1 (C-1), 74.7 (C-2 and C-5), 24.3 (C-3), 71.3 (C-4), 65.4 (C-6), 69.9 (ArCH₂O, ×2), 57.3 (OCH₃), 136.9 (q-aromatic), 129.2, 128.5, 127.9, 127.4 and 114.7 (aromatic).
48. 1,6-anhydro-3-deoxy-4-O-(2,4-difluorobenzyl)-2-O-methyl-β-D-ribo-hexopyranose, $[\alpha]_D$ −45.8°; $^{13}$C-nmr data: 100.1 (C-1), 74.5 and 74.4 (C-2 and C-5), 24.2 (C-3), 72.6 (C-4), 65.3 (C-6), 63.3 (d, 3.0 Hz, ArCH₂O), 57.2 (OCH₃), 131.0 (dd, 6.0 and 9.5 Hz), 111.1 (dd, 3.6 and 21.0 Hz), and 103.3 (t, 25.5 Hz aromatic).
49. 1,6-anhydro-4-O-(3-chloro-2-fluorobenzyl)-3-deoxy-2-O-methyl-β-D-ribo-hexopyranose, $[\alpha]_D$ −41.5°; $^{13}$C-nmr data: 100.1 (C-1), 74.5 and 74.4 (C-2 and C-5), 24.1 (C-3), 72.9 (C-4), 65.3 (C-6), 63.7 (d, 3.7 Hz, ArCH₂O), 57.2 (OCH₃), 134.5, 129.6, 128.1 (d, 3.0 Hz), and 124.5 (d, 4.4 Hz, aromatic).
50. 1,6-anhydro-3-deoxy-4-O-(2,3-difluorobenzyl)-2-O-methyl-β-D-ribo-hexopyranose, $[\alpha]_D$ −41.2°; $^{13}$C-nmr data: 100.1 (C-1), 74.5 and 74.4 (C-2 and C-5), 24.0 (C-3), 72.8 (C-4), 65.3 (C-6), 63.4 (m, ArCH₂O), 57.1 (OCH₃), 123.7–124.7 (m, aromatic), 116.2 (d, 17.0 Hz, aromatic).
51. 1,6-anhydro-3-deoxy-4-O-(2,5-difluorobenzyl)-2-O-methyl-β-D-ribo-hexopyranose, m.p. 54°–55° C., $[\alpha]_D$ −48.6°; $^{13}$C-nmr data: 100.1 (C-1), 74.5 and 74.3 (C-2 and C-5), 24.2 (C-3), 73.0 (C-4), 65.3 (C-6), 63.4 (dd, 2.5 and 0.8 Hz, ArCH₂O), 57.2 (OCH₃), and 114.3–116.7 (m, 9 peaks, aromatic).
52. 1,6-anhydro-3-deoxy-2-O-methyl-4-O-(2,3,5,6-tetrafluorobenzyl)-β-D-ribo-hexopyranose, m.p. 96°–97° C., $[\alpha]_D$ −41.0°; $^{13}$C-nmr data: 100.2 (C-1), 74.6 and 74.4 (C-2 and C-5), 23.5 (C-3), 73.1 (C-4), 65.3 (C-6), 57.9 (t, 2.2 Hz, ArCH₂O), 57.1 (OCH₃), 106.0 (t, 22.7 Hz, aromatic)
53. 1,6-anhydro-4-O-(9-anthracenemethyl)-3-deoxy-2-O-methyl-β-D-ribo-hexopyranose, m.p. 159°–160° C., $[\alpha]_D$ +11.2°; $^{13}$C-nmr data: 100.1 (C-1), 75.2 and 74.7 (C-2 and C-5), 23.9 (C-3), 70.7 (C-4), 65.3 (C-6), 62.1 (ArCH₂O), 57.3 (OCH₃), 131.3, 131.2 and 128.1 (q-aromatic), 128.9, 126.1, 124.5, 124.4 and 128.3 (aromatic).
54. 1,6-anhydro-3-deoxy-2-O-methyl-4-O-(2,3,6-trichlorobenzyl)-β-D-ribo-hexopyranose, m.p. 100°–100.5° C., $[\alpha]_D$ −31.6° C.; $^{13}$C-nmr data: 100.2 (C-1), 74.9 and 74.5 (C-2 and C-5), 23.5 (C-3), 72.8 (C-4), 65.4 (C-6), 66.1 (ArCH₂O), 57.1 (OCH₃), 135.0, 130.5, and 128.5 (aromatic).

EXAMPLE 5

3-O-Alkylations

Using a method analagous to Example 3, but starting from 1,6-anhydro-4-O-benzyl-2-O-methyl-β-D-glucopyranose (see Example 10) and methyl iodide, the following compound was prepared:
1,6-anhydro-4-O-benzyl-2,3-di-O-methyl-β-D-glucopyranose, $[\alpha]_D$ −36.4°.

Using a method analagous to Example 3, but starting from 1,6-anhydro-4-O-benzyl-2-deoxy-2-C-methyl-β-D-glucopyranose (Tetrahedron Lett. 22 (1981), 4315–4318) and methyl iodide the following compound was prepared:
1,6-anhydro-4-O-benzyl-2-deoxy-2-C-methyl-3-O-methyl-β-D-glucopyranose; $^{13}$C-nmr data: 103.9 (C-1), 37.7 (C-2), 80.7 (C-3), 73.9 (C-4), 76.0 (C-5), 64.6 (C-6), 71.0 (PhCH₂O), 57.4 (OCH₃) and 15.6 (C-CH₃).

EXAMPLE 6

1,6-Anhydro-4-O-benzyl-3-deoxy-β-D-erythro-hexopyranos-2-ulose

A stock solution of potassium benzoxide in benzyl alcohol was prepared by adding potassium hydride (0.13 g, containing a small amount of oil) to benzyl alcohol (2.5 ml). A portion of this solution (0.05 ml) was then added to a solution of levoglucosenone (0.145 g) in benzyl alcohol (5 ml), causing the mixture to darken slightly. After 5 min, this solution was diluted with chloroform, successively washed with M aqueous hydrochloric acid, saturated aqueous sodium hydrogen carbonate, and distilled water, the chloroform evaporated in vacuo, and the benzyl alcohol removed by distillation at 26.6 Pa, and, finally, by azeotropic distillation with water (×2) and absolute ethanol. This yielded the title compound as a yellow oil (0.20 g, 79%); a single component by t.l.c. Purification by vacuum distillation gave a colorless oil, $[\alpha]_D$ −143°; $\gamma_{max}^{FILM}$ 1740 cm$^{-1}$ (C=O); $^{13}$C-n.m.r.: 198.3 (C-2), 137.4 (Ph, q), 128.6, 128.0, and 127.7 (Ph), 101.4 (C-1), 76.2 and 74.9 (C-4, 5), 70.8 and 65.2 (C-6 and PhCH₂), and 37.4 (C-3); it subsequently crystallized from ether/hexane; m.p. 57°–58° C., $[\alpha]_D$ −146°. Anal. Calc. for C₁₃H₁₃O₄: C, 66.7; H, 6.0. Found: C, 66.5; H, 6.1.

EXAMPLE 7

1,6-Anhydro-4-O-benzyl-3-deoxy-β-D-erythro-hexopyranos-2-ulose dimethyl acetal 1,6-Anhydro-4-O-benzyl-3-deoxy-β-D-erythro-hexopyranos-2-ulose (Example 6) (0.30 g) was dissolved in 3% HCl in dry methanol (10 ml) and the solution allowed to stand at room temperature for 0.5 h. Chloroform was added and the solution was washed with saturated aqueous sodium hydrogen carbonate, water, dried (MgSO₄), and concentrated to a syrup. Purification by flash chromatography on silica gel gave the title compound (0.29 g) $[\alpha]_D$ −52.1°; $^{13}$C-nmr data: 99.6 (C-1), 96.8 (C-2), 29.0 (C-3), 72.6 (C-4), 74.6 (C-5), 65.9 (C-6), 70.6 (PhCH₂O), 138.1, 128.5, 127.7 and 127.6 (aromatic), 49.1 and 47.9 (OCH₃).

EXAMPLE 8

1,6-Anhydro-4-O-benzyl-3-deoxy-2-C-methyl-β-D-ribo-hexopyranose and
1,6-Anhydro-4-O-benzyl-3-deoxy-2-C-methyl-β-D-arabino-hexopyranose To a solution of 1,6-anhydro-4-O-benzyl-3-deoxy-β-D-erythrohexopyranos-2-ulose (Example 6) (1.17 g) in dry tetrahydrofuran (20 ml) at −30° C. was added in a nitrogen atmosphere methyl-magnesium bromide (1.5M in ether, 4.0 ml, 1.2 eq) and the resulting solution was stirred at −30° C. for 1 hour. Water (0.5 ml) was added carefully and then the mixture was partitioned between ether and 2M aqueous HCl. The organic layer was washed with water, dried (MgSO₄) and concentrated to a syrup. Chromatography on silica gel gave firstly the less polar first title compound (0.17 g) $[\alpha]_D$ −58.4°, and then the second title compound (0.78 g) which crystallized from ethyl acetate/light petroleum, m.p. 75°–76° C. $[\alpha]_D$ −70.9°.

The following $^{13}$C nmr peaks were recorded:

First title compound: 105.8 (C-1), 70.0 (C-2), 33.3 (C-3), 73.7 and 73.5 (C-4 and C-5), 65.7 (C-6), 70.5 (PhCH$_2$O), 128.5, 127.9, 127.6 (aromatic), and 23.2 (C-CH$_3$).

Second title compound: 105.9 (C-1), 69.4 (C-2), 35.9 (C-3), 74.7. and 74.0 (C-4 and C-5), 66.0 (C-6), 69.9 (PhCH$_2$O), 138.0, 128.4, 127.7, 127.5 (aromatic), and 23.4 (C-CH$_3$).

EXAMPLE 9

1,6-Anhydro-4-O-benzyl-2,3-dideoxy-2-S-methyl-2-thio-$\beta$-D-ribo-hexopyranose A solution of 1,6-anhydro-4-O-benzyl-3-deoxy-$\beta$-D-arabino-hexopyranose (Example 2) (0.20 g) in dry dichloromethane (5 ml) containing pyridine (0.4 ml) was cooled to $-10°$ C. and trifluoromethanesulphonic anhydride (0.173 ml, ~1.2 eq) was added dropwise with stirring. After 0.5 h the solution was washed with 1M aqueous HCl, saturated aqueous sodium hydrogen carbonate, and water, dried (MgSO$_4$) and concentrated to dryness to give a crude syrupy triflate ester. This was immediately dissolved in N,N-dimethylformamide (5 ml) and lithium thiomethoxide (100 mg) was added all at once with stirring and stirring was continued overnight. Ether (20 ml) was added and the mixture was washed with water, 2M aqueous sodium hydroxide, water, dried (MgSO$_4$) and concentrated to dryness. Trituration of the residual syrup with ether/light petroleum gave 0.178 g of crystalline title compound, m.p. 75°–76° C., $[\alpha]_D +17.9°$; $^{13}$C-nmr data: 102.0 (C-1), 44.6 (C-2), 26.3 (C-3), 72.0 (C-4), 75.3 (C-5), 66.0 (C-6), 70.3 (PhCH$_2$O), 138.1, 128.3, 127.6 and 127.5 (aromatic), and 15.9 (S-CH$_3$).

EXAMPLE 10

1,6-Anhydro-4-O-benzyl-2-O-methyl-$\beta$-D-glucopyranose

A solution of 4-O-benzyl-1,6:2,3-dianhydro-$\beta$-D-mannopyranose (Collect. Czech. Chem. Commun. 36 (1971) 2216–2225) (0.150 g) in 3% hydrogen chloride in dry methanol (20 ml) was allowed to stand at room temperature for 2 days and was then concentrated to dryness. Purification of the two components present was effected by silica gel chromatography and gave the major more polar title compound (0.120 g, 70% yield) as a colourless syrup.

EXAMPLE 11

1,6-Anhydro-4-O-benzyl-3-deoxy-2-O-methyl-$\beta$-L-ribo-hexopyranose

A solution of 1,6-anhydro-2-O-benzoyl-3-deoxy-$\beta$-L-ribo-hexopyranose (Preparative Example 2) (0.5 g) in dichloromethane/hexane (25 ml, 1:4 v/v) was stirred with benzyl trichloroacetimidate (1.44 g) and then two drops of trifluoromethanesulphonic acid were added. The solution was stirred for 24 h at room temperature and then two more drops of the acid catalyst were added. After stirring for 8 h more, toluene (30 ml) was added and the solution was washed with saturated aqueous sodium hydrogen carbonate, dried (MgSO$_4$) and concentrated to a syrup. This crude benzyl ether was then dissolved in methanol (15 ml) and a few drops of 1M aqueous sodium hydroxide were added. After 4 h at room temperature the solution was neutralised with acetic acid and then concentrated to dryness. The residue was fractionated on a short column of silica gel to separate the 1,6-anhydro-4-O-benzyl-3-deoxy-$\beta$-L-ribo-hexopyranose formed from the methyl benzoate. This fractionated product was then methylated by the standard alkylation procedure (see Example 3) to give the title compound 0.25 g. $[\alpha]_D +41.8°$. It had identical $^1$H and $^{13}$C nmr characteristics with its enantiomer the title compound of Example 3(1).

EXAMPLE 12

1,6-Anhydro-4-O-benzyl-2,3-dideoxy-2-C-methyl-$\beta$-D-ribo-hexopyranose

A solution of 1,6-anhydro-4-O-benzyl-2-deoxy-2-C-methyl-$\beta$-D-glucopyranose (Tetrahedron Lett. 22 (1981) 4315–4318) (0.280 g) in dry THF (10 ml) was stirred while sodium hydride (1.2 eq) was added slowly. When effervescence had ceased, a large excess (>10 eq) of carbon disulphide was added and the solution was stirred at room temperature for 0.5 h. Methyl iodide (5 eq) was then added and the solution was stirred a further 0.5 h at room temperature. Ether (50 ml) was added and the mixture was washed with water. The aqueous washings were back extracted with ether and the combined ether extracts were washed with saturated aqueous sodium chloride and then dried (MgSO$_4$) and concentrated to a light yellow syrup. This was dissolved in toluene (25 ml) and heated under reflux in a nitrogen atmosphere while tributyltin hydride (1.05 eq) in toluene (2 ml) was added slowly over 3 h. The solution was then heated under reflux for a further 16 h before being concentrated again to dryness.

Purification of the residual syrup by chromatography on silica gel gave 0.213 g of the title compound; $^{13}$C-nmr data: 105.4 (C-1), 33.3 (C-2), 26.0 (C-3), 73.8 (C-4), 75.0 (C-5), 65.9 (C-6), 70.4 (PhCH$_2$O), 16.9 (C-CH$_3$), 128.4, 127.7, 127.5 (aromatic).

EXAMPLE 13

1,6-Anhydro-2-azido-4-O-benzyl-2,3-dideoxy-$\beta$-D-ribo-hexopyranose

To a solution of 1,6-anhydro-4-O-benzyl-3-deoxy-2-O-p-toluenesulphonyl-$\beta$-D-arabino-hexopyranose (See Preparative Example 3) (0.50 g) in N,N-dimethylformamide (10 ml) was added sodium azide (0.25 g) and the mixture was heated with stirring at 150° C. for 3 days. Chloroform was added and the mixture was washed with water ($\times$4), dried (MgSO$_4$) and concentrated to a syrup. Purification by flash chromatography gave the title compound (0.30 g), $[\alpha]_D -14.8°$; $^{13}$C-nmr data: 100.8 (C-1), 55.8 (C-2), 24.6 (C-3), 71.0 and 70.6 (C-4 and PhCH$_2$O), 74.7 (C-5), 65.7 (C-6), 137.8, 128.4, and 127.7 (aromatic).

EXAMPLE 14

2-O-Acetyl-1,6-anhydro-4-O-benzyl-3-deoxy-$\beta$-D-ribo-hexopyranose

A.

1,6-Anydro-4-O-benzyl-3-deoxy-$\beta$-D-ribo-hexopyranose

A solution of 1,6-anhydro-4-O-benzyl-3-deoxy-$\beta$-D-erythro-hexopyranos-2-ulose in benzyl alcohol was prepared as described in Example 6, except that 0.088 g of levoglucosenone were used as starting material and, 5 min after the addition of potassium benzoxide, a suspension of sodium borohydride (0.073 g) in ethanol (4 ml) was added to the mixture, which was then stirred for 0.5 h at room temperature, made neutral with acetic acid, evaporated under vacuum, and the resulting white residue transferred to a short column of silica, which was eluted with a gradient of ethyl acetate/hexane (from 1:2 to 2:1). The fractions found by t.l.c. to contain the title compound A were combined and evaporated, to give material that spontaneously crystallized (0.106 g, 64% from levoglucosenone). $^1$H-Nmr spectroscopy of this material showed it to be an 9:11 mixture of the title compound A and the D-arabino isomer determined from the relative intensities of their H-3 resonances.

Column-chromatographic separation (eluant: gradient of ethyl acetate/hexane from 1:2 to 2:1) provided crystalline samples of both isomers. 1,6-Anhydro-4-O-benzyl-3-deoxy-$\beta$-D-arabino-hexopyranose was twice recrystallized from ethyl acetate/hexane to give white needles, m.p. 117.5°-119° C., $[\alpha]_D$ −91°; $\gamma_{max}^{CCl4}$ 3590 cm$^{-1}$; Anal. Calc. for $C_{13}H_{16}O_4$: C, 66.1; H, 6.8. Found: C, 66.3; H, 7.0; $^1$H-nmr data: 5.35 s (H-1), 3.5–3.9 m (H-2, H-6,6), 1.51 ddd (H-3a, $J_{2,3a}$ 10.3, $J_{3a,4}$ 4.4, $J_{3a,3e}$ 14.2 Hz), 2.21 br dd (H-3e, $J_{2,3e}$ 6.1, $J_{3e,4}$ small), 3.4–3.5 m (H-4), 4.5–4.6 m (H-5 and PhC$\underline{H}_2$), 3.5–3.9 m (H-6,6), 7.2–7.4 m (Ph), and 2.28 (OH, $J_{2,OH}$ 9.1).

Syrupy title compound A crystallized spontaneously from diethyl ether at −20° C., and had m.p. 36°–37° C. On recrystallization from diethyl ether at −20° C. and then from ethyl acetate/hexane, a second, higher-melting form was obtained as white needles, m.p. 56°–57°, $[\alpha]_D$ −60°; $\gamma_{max}^{CCl4}$ 3560 cm$^{-1}$; Anal. Calc. for $C_{13}H_{16}O_4$: C, 66.1; H, 6.8 Found: C, 66.1; H, 6.7; $^1$H-nmr data: 5.40 d (H-1, $J_{1,2}$ 2.4 Hz), 3.56 dq (H-2, $J_{2,3a}$ 5.9, $J_{2,3e}$ <1.5, $J_{2,OH}$ 12.1), 1.98 m (H-3a, 3e), 3.46 q (H-4, $J_{3a,4}$ 4.5, $J_{3e,4}$ <1.5, $J_{4,5}$ 2.8), 4.6–4.7 m (H-5 and PhC$\underline{H}_2$), 3.75 dd (H-6$_{endo}$, $J_{5,6endo}$ 0.8, $J_{6,6}$ 7.7), 3.83 dd (H-6$_{exo}$, $J_{5,6exo}$ 5.4), 7.3–7.4 m (Ph), and 3.02 d (OH).

B.
2-O-Acetyl-1,6-anhydro-4-O-benzyl-3-deoxy-$\beta$-D-ribo-hexopyranose

Acetylation of the product of step A (0.582 g) was conducted in the usual way (see Carbohydr. Res. 67 (1978) 433–447), to yield the title compound (0.670 g, 98%) which crystallized spontaneously upon removal of the solvent. Recrystallization (×2) from ethyl acetate/hexane gave white needles having m.p. 85°–87° C., $[\alpha]_D$ −38°; Anal. Calc. for $C_{15}H_{18}O_5$: C, 64.7; H, 6.5. Found: C, 64.8; H, 6.6.; $^1$H-nmr data: 5.44 br s (H-1), 4.4–4.7 m (H-2, H-5, and PhC$\underline{H}_2$), 1.95–2.1 m (H-3a, 3e), 3.33 m (H-4), 3.65–3.9 m (H-$\overline{6}$,6), 7.2–7.4 m (Ph), and 2.12 s (OAc).

EXAMPLE 15

C-1-Alkylations

A solution of 1,6-anhydro-4-O-benzyl-3-deoxy-2-O-methyl-$\beta$-D-ribo-hexopyranose (example 3.1) (10.5 g) in acetic anhydride (50 ml) was stirred under nitrogen in an ice bath while boron trifluoride diethyl etherate (5 drops) was added. The solution was stirred in the ice bath for 1 h and then after the addition of chloroform (100 ml) the solution was washed with saturated aqueous sodium bicarbonate, dried (MgSO$_4$) and then concentrated at about 50° C. and 2 torr, to remove the chloroform and the excess acetic anhydride. Chromatography of the residual syrup on silica gel gave a syrup composed predominantly of 1,6-di-O-acetyl-4-O-benzyl-3-deoxy-2-O-methyl-D-ribo-hexopyranose (12.7 g, 86% yield); $^{13}$C-nmr data: 170.7 and 169.4 (O$\underline{C}$OCH$_3$), 137.4, 128.4 and 127.9 (aromatic), 88.3 (C-1), 74.8, 71.2 and 70.7 (C-2, C-4 and C-5), 70.6 (ArCH$_2$O), 62.9 (C-6), 57.2 (OCH$_3$), 29.6 (C-3), 20.9 and 20.7 (OCO$\underline{C}$H$_3$). This diacetate was dissolved in dry methanol (150 ml) and a solution of sodium methoxide in methanol was added until the pH was 10, and the resulting solution was allowed to stand at ambient temperature overnight before being added to saturated aqueous sodium chloride. The resulting mixture was extracted four times with chloroform, the combined extracts were dried (MgSO$_4$) and concentrated to give a quantitative yield of the syrupy diol 4-O-benzyl-3-deoxy-2-O-methyl-D-ribo-hexopyranose. This diol (Xg) was then dissolved in dry tetrahydrofuran (50×ml) and 4–5 mole equivalents of the appropriate alkyl magnesium halide (2–3M solution in diethyl ether) was added. The resulting solution was heated under reflux with exclusion of moisture until the diol was all consumed (generally 4–6 h) as evidenced by thin layer chromatography. Excess Grignard reagent was destroyed by the careful addition of water, and then 2M aqueous hydrochloric acid was added and the mixture was extracted three times with chloroform. The combined extracts were washed with saturated aqueous sodium hydrogen carbonate, and the aqueous layer was back extracted with chloroform. The combined chloroform extracts were dried (MgSO$_4$) and concentrated. The residual syrup was dissolved in acetone (10×ml) and stirred while anhydrous cupric sulphate (0.2×g) and ($\pm$)-10-camphorsulphonic acid (0.05×g) were added. The resulting mixture was stirred at ambient temperature until reaction was complete (1–2 h; t.l.c. evidence) and then was poured into saturated aqueous sodium hydrogen carbonate. The resulting mixture was extracted three times with chloroform, the combined extracts were dried (MgSO$_4$) and concentrated to dryness. A syrup was obtained, believed to comprise mainly a mixture of the C-1 epimers of the C-1-alkylated 4-O-benzyl-3-deoxy-5,6-O-isopropylidene-2-O-methyl-D-ribo-hexitol. An alternative route to this product is by corresponding Grignard reaction on the product of Preparative Example 8.

This residual syrup was subjected to a "Swern Oxidation" as follows: (see A. J. Mancuso and D. Swern, Synthesis, 1981, 179). A stirred solution of oxalyl chloride (1.3 mole equivalents) in dichloromethane was cooled under argon to −70° C. and a solution of dimethylsulphoxide (2.6 mol. equiv.) in dichloromethane was added dropwise. Five minutes after the addition was complete a solution of the syrupy residue from the above procedure in dichloromethane was added slowly and the resulting mixture was stirred at −70° C. for 30 min. Triethylamine (5 mol. equiv.) was then added and the mixture was stirred and allowed to warm to about 0°–10° C., and then washed with water, 2M aqueous hydrochloric acid, saturated aqueous sodium hydrogen carbonate and then dried (MgSO$_4$) and the solvent was removed under reduced pressure.

The residue was chromatographed on silica gel to separate the product from minor contaminants. This chromatographed material was then dissolved in a mixture of 90% acetic acid and 10% water and the solution was heated at about 60°–80° C. for 2 h. The solvents were then removed under reduced pressure and the residue again subjected to chromatography on silica gel to give the C-1 alkylated analogues of 1,6-anhydro-4-O-benzyl-3-deoxy-2-O-methyl-$\beta$-D-ribo-hexopyranose in approximately 50–60% overall yield. These compounds may alternatively be described as a (1R.2S,4R)-5-alkyl-2-benzyloxy-4-methoxy-6,8-dioxabicyclo[3.2.1]octanes.

Using the appropriate alkyl magnesium halide the following compounds were prepared by the above procedure:

1. (1R,2S,4R)-2-benzyloxy-4-methoxy-5-methyl-6,8-dioxabicyclo[3.2.1]octane, $[\alpha]_D$ −63.2°; $^{13}$C-nmr data: 138.4, 128.3, 127.6 and 127.5 (aromatic), 107.2 (C-5), 77.7 and 76.2 (C-1 and C-4), 71.1 (C-2), 70.3 (ArCH$_2$O), 66.0 (C-7), 57.6 (OCH$_3$), 24.0 (C-3), 20.8 (C-CH$_3$).

2. (1R,2S,4R)-2-benzyloxy-5-ethyl-4-methoxy-6,8-dioxabicyclo[3.2.1]octane, $[\alpha]_D$ −54.2°; $^{13}$C-nmr data: 138.4, 128.2, 127.6 and 127.4 (aromatic), 108.5 (C-5), 76.1 and 76.0 (C-1 and C-4), 71.6 (C-2), 70.3 (ArCH$_2$O), 66.2 (C-7), 57.3 (OCH$_3$), 25.9 (CH$_2$CH$_3$), 24.0 (C-3), and 6.5 (CH$_2$CH$_3$).

3. (1R,2S,4R)-2-benzyloxy-4-methoxy-5-(1-methylethyl)-6,8-dioxabicyclo[3.2.1]octane, m.p. 80°–81° C. $[\alpha]_D$ −46.1°; $^{13}$C-nmr data: 138.5, 128.3, 127.6 and 127.4 (aromatic), 109.9 (C-5), 76.0 and 74.0 (C-1 and C-4), 71.5 (C-2), 70.3 (ArCH$_2$O), 66.3 (C-7), 57.0 (OCH$_3$), 29.1 (CH(CH$_3$)$_2$), 24.0 (C-3), 17.1 and 14.7 (CH(CH$_3$)$_2$).

4. (1R,2S,4R)-2-benzyloxy-5-butyl-4-methoxy-6,8-dioxabicyclo[3.2.1]octane, $[\alpha]_D$ −50.8°; $^{13}$C-nmr data: 138.4, 128.2, 127.6 and 127.4 (aromatic), 108.5 (C-5), 76.4 and 75.9 (C-1 and C-4), 71.5 (C-2), 70.3 (ArCH$_2$O), 66.2 (C-7), 57.3 (OCH$_3$), 32.7 (CH$_2$CH$_2$CH$_2$CH$_3$), 24.4 (C-3), 23.9 and 22.8 (CH$_2$CH$_2$CH$_2$CH$_3$) and 14.0 ((CH$_2$)$_3$CH$_3$).

5. (1R,2S,4R)-2-benzyloxy-4-methoxy-5-propyl-6,8-dioxabicyclo[3.2.1]octane, $[\alpha]_D$ −54.8°; $^{13}$C-nmr data: 138.4, 128.2, 127.5 and 127.3 (aromatic), 108.3 (C-5), 76.4 and 75.9 (C-1 and C-4), 71.6 (C-2), 70.2 (ArCH$_2$O), 66.1 (C-7), 57.2 (OCH$_3$), 35.2 (CH$_2$CH$_2$CH$_3$), 23.7 (C-3), 15.5 (CH$_2$CH$_2$CH$_3$) and 14.3 (CH$_2$CH$_2$CH$_3$).

6. (1R,2S,4R)-2-benzyloxy-4-methoxy-5-phenyl-6,8-dioxabicyclo[3.2.1]octane, $[\alpha]_D$ −35.8°; $^{13}$C-nmr data: 138.2, 128.5, 128.3, 127.8, 127.6 and 126.1 (aromatic), 108.3 (C-5), 79.3, 75.7 and 74.8 (C-1, C-2 and C-4), 70.5 (ArCH$_2$O), 67.5 (C-7), 57.7 (OCH$_3$) and 29.5 (C-3).

7. (1R,2S,4R)-2-benzyloxy-4-methoxy-5-(1-methylpropyl)-6,8-dioxabicyclo[3.2.1]octane, $[\alpha]_D$ −43.8°; $^{13}$C-nmr data: 138.5, 128.2, 127.6, 127.4 (aromatic), 110.1 and 110.0 (C-5), 75.9 and 75.7, 74.2 and 74.0 (C-1 and C-4), 71.6 and 71.5 (C-2), 70.2 (ArCH$_2$O), 66.5 and 66.2 (C-7), 57.0 (OCH$_3$), 40.0 and 35.9 (CH(CH$_3$)CH$_2$CH$_3$), 24.0, 23.8, 23.4 and 21.3 (C-3 and CH(CH$_3$)CH$_2$CH$_3$), 13.4, 11.9 and 10.8 (CH(CH$_3$)CH$_2$CH$_3$). The pairs of resonances are due to the presence of two diastereoisomers in the 1-methylpropyl side chain.

EXAMPLE 16

2-O-Aralkylations of (1R,2S,4R)-5-ethyl-2-hydroxy-4-methoxy-6,8-dioxabicyclo[3.2.1]octane.

Using a method analogous to Example 3, starting from the above named compound (see Preparative Example 4) and an appropriate aralkyl halide as starting materials, the following compounds were prepared:

1. (1R,2S,4R)-2-(2-bromobenzyloxy)-5-ethyl-4-methoxy-6,8-dioxabicyclo[3.2.1]octane, $[\alpha]_D$ −49.8°; $^{13}$C-nmr data: 137.7, 132.1, 129.3, 128.7 and 127.3 (aromatic), 108.7 (C-5), 76.1 and 75.9 (C-1 and C-4), 73.0 (C-2), 69.9 (ArCH$_2$O), 66.2 (C-7), 57.4 (OCH$_3$), 25.9 (CH$_2$CH$_3$), 24.2 (C-3), and 6.5 (CH$_2$CH$_3$).

2. (1R,2S,4R)-2-(2-chlorobenzyloxy)-5-ethyl-4-methoxy-6,8-dioxabicyclo[3.2.1]octane, $[\alpha]_D$ −58.9°; $^{13}$C-nmr data: 136.1, 132.4, 129.1, 128.9, 128.4 and 126.7 (aromatic), 108.6 (C-5), 76.1 and 75.9 (C-1 and C-4), 73.0 (C-2), 67.5 (ArCH$_2$O), 66.2 (C-7), 57.3 (OCH$_3$), 25.9 (CH$_2$CH$_3$), 24.1 (C-3) and 6.4 (CH$_2$CH$_3$).

3. (1R,2S,4R)-5-ethyl-4-methoxy-2-(2-methylbenzyloxy)-6,8-dioxabicyclo[3.2.1]octane, m.p. 43°–44° C.; $[\alpha]_D$ −59.2°; $^{13}$C-nmr data: 136.9, 136.0, 130.2, 128.7, 127.6 and 125.5 (aromatic), 108.7 (C-5), 76.1 and 75.9 (C-1 and C-4), 71.4 (C-2), 68.8 (ArCH$_2$O), 66.3 (C-7), 57.3 (OCH$_3$), 26.0 (CH$_2$CH$_3$), 23.8 (C-3), 18.9 (Ar-Me), 6.5 (CH$_2$CH$_3$).

EXAMPLE 17

1,6-Anhydro-4-O-benzyl-3-deoxy-2-C-ethyl-β-D-ribo-hexopyranose and
1,6-anhydro-4-O-benzyl-3-deoxy-2-C-ethyl-β-D-arabino-hexopyranose Using a method analogous to Example 8, starting from 1,6-anhydro-4-O-benzyl-3-deoxy-β-D-erythro-hexopyranos-2-ulose (Example 6) and ethyl magnesium bromide (2.5M in ether) as starting materials, followed by chromatography on silica gel, gave the less polar first title compound, $[\alpha]_D$ −58.1°; $^{13}$C-nmr data: 137.5, 128.5, 127.8 and 127.6 (aromatic), 105.0 (C-1), 73.9 and 73.5 (C-4 and C-5), 71.6 (C-2), 70.5 (ArCH$_2$O), 65.6 (C-6), 31.4 and 29.1 (C-3 and CH$_2$CH$_3$), and 6.2 (CH$_2$CH$_3$); and then the second title compound which crystallised from ethyl acetate/light petroleum.

EXAMPLE 18

1,6-Anhydro-4-O-benzyl-3-deoxy-4-C-methyl-2-O-methyl-β-D-ribo-hexopyranose

To a stirred solution of methyl 6-O-tert-butyldiphenylsilyl-3-deoxy-2-O-methyl-α-D-erythro-hexopyranosid-4-ulose (see preparative Example 7) (4.0 g), in dry tetrahydrofuran (50 ml) at −5° C. was added dropwise a solution of methyl magnesium iodide (2.5M in ether) (6 ml), and the solution was stirred in the cooling bath for 0.5 h. 2M Aqueous hydrochloric acid was added and the mixture was extracted three times with chloroform. The combined extracts were washed with saturated aqueous sodium hydrogen carbonate, dried (MgSO$_4$) and the chloroform was removed in vacuo. The residue was dissolved in 10% aqueous acetic acid (100 ml) and the solution was heated to 85° C. for 6 h, before being evaporated to dryness in vacuo. The residue was chromatographed on silica gel to give 0.64 g of the major product as a pair of isomers, epimeric at C-4. This material was then dissolved in diethyleneglycol dimethyl ether (25 ml) containing p-toluenesulphonic acid (0.05 g) and the solution was heated at 160° C. for 3 h. Excess triethylamine was added to the cooled solution and then the solvent was removed in vacuo at a bath temperature of 60° C. Chromatography on silica gel of the residue, eluting with ethyl acetate/light petroleum mixtures; gave the more mobile product (0.19 g) mixed with traces of diethyleneglycol dimethyl ether. This material was stirred in dry N,N-dimethylformamide with sodium hydride (1.3 equivalents) and benzyl bromide (2 equivalents) for 4 h. Water was added and the mixture was extracted twice with chloroform. The combined extracts were washed three times with water, and then dried (MgSO₄) and concentrated in vacuo. The residue was chromatographed on silica gel to give the title compound (0.164 g). Recrystallised from pentane it had m.p. 45°–46° C., $[\alpha]_D$ −66.0°.

Using an analagous method the following compound has also been prepared: 1,6-anhydro-4-O-benzyl-3-deoxy-4-ethyl-2-O-methyl-β-D-ribo-hexopyranose, $[\alpha]_D$ −77.4°, ¹³C-nmr data: 139.2, 128.0, 127.2 and 126.9 (aromatic), 99.9 (C-1), 76.8 and 75.4 (C-2 and C-5), 74.4 (C-4), 64.8 and 63.7 (ArCH₂O and C-6), 57.2 (OCH₃), 28.4 and 26.6 (C-3 and CH₂CH₃), 6.2 (CH₂CH₃).

EXAMPLE 19

1,6-Anhydro-2,2'-anhydro-4-O-benzyl-3-deoxy-2-C-hydroxymethyl-β-D-arabino-hexopyranose To a solution of 1,6-anhydro-4-O-benzyl-3-deoxy-β-D-erythrohexopyranose-2-ulose (see Example 8, 1.6 g) in chloroform (10 ml) at 0° C. was added a solution of diazomethane (prepared from N-nitrosomethylurea, 5.0 g) in ether (50 ml). After storage at 4° C. for 2 days, the solvents and excess diazomethane were removed by evaporation. The partly crystalline residue was flash chromatographed to give as the main product the title compound (0.88 g, 57%), m.p. 73°–74° C., $[\alpha]_D$ −76.3°; ¹³C-nmr data: 104.2 (C-1), 56.5 (C-1), 28.6 (C-3), 74.1 and 74.6 (C-4 and C-5), 65.8 (C-6), 52.1 (C-2'), 70.6 (PhCH₂O), 137.8, 128.4, 127.8 and 127.5 (aromatic).

EXAMPLE 20

1,6-Anhydro-2,4-di-O-benzyl-β-D-allopyranose

A.
1,6-Anhydro-2,4-di-O-benzyl-β-D-ribo-hex-3-ulopyranose 1,6-Anhydro-2,4-di-O-benzyl-β-D-glucopyranose (3.2 g, 9.3 mmol), acetic acid (290 μl, 4.8 mmol), pyridinium dichromate (5.2 g, 14 mmol), and freshly activated molecular sieves (3 Å, 6.5 g) (Tetrahedron Lett, 26 (1985) 1699–1702) were stirred for 3 h in dichloromethane (65 ml). The reaction mixture was diluted with ether and filtered twice through celite and once through silica gel. The solvent was evaporated and the resulting brown syrup chromatographed on silica gel (hexane/ethyl acetate, 2:1 then 1:1) to give the title compound A (2 g, 63%) as white crystals, m.p. 79°–81° C. (after recrystallisation from hexane/ethyl acetate) (Lit, m.p. 78°–79° C.; Collect. Czech. Chem. Commun. 33 (1968) 1143–1156); ¹³C-nmr data: 136.7 (C-3), 128.4, 128.2, 128.0 (aromatic), 101.6 (C-1), 80.2 and 78.2 (C-2 and C-4), 75.1 (C-5), 72.2 and 71.6 (PhCH₂O), and 65.4 (C-6).

B. 1,6-Anhydro-2,4-di-O-benzyl-β-D-allopyranose

A solution of the product from step A (2.5 g, 7.3 mmol) in ethanol (80 ml) was cooled in a dry ice-acetone bath. A solution of sodium borohydride (420 mg, 10 mmol) in ethanol (20 ml) was added with stirring. The reaction was complete almost immediately with high selectivity for the title alcohol (t.l.c.evidence). The solution was brought to room temperature and acid resin (Dowex 50W-X8; H+ form) was added until the pH of the solution was 5–6. The resin was filtered off, washed with ethanol, and the filtrate was evaporated to dryness. The residue was dissolved in methanol and evaporated to dryness twice. The resulting syrup was chromatographed on silica gel (hexane/ethyl acetate, 2:3) to give the title compound B as a colourless syrup. (1.9 g, 76%) $[\alpha]_D$ −56.2°; ¹³C-nmr data: 128.4 and 127.8 (aromatic), 99.9 (C-1), 76.2 (C-2 and C-4), 73.7 and 72.5 (OCH₂Ph), 73.0 (C-5), 64.6 (C-6), and 63.3 (C-3).

EXAMPLE 21

1,6-Anhydro-2,4-di-O-benzyl-3-O-methyl-β-D-allopyranose

A solution of 1,6-anhydro-2,4-di-O-benzyl-β-D-allopyranose (Example 20) (1 g, 2.9 mmol), sodium hydride (60%, 200 mg, 5 mmol), methyl iodide (excess) and tetrabutylammonium iodide (trace) in tetrahydrofuran was stirred overnight at room temperature. Ethanol was added to destroy excess sodium hydride and the solution evaporated to near dryness. The residue was taken up in dichloromethane and washed with water and brine. The organic phase was dried (Na₂SO₄) and evaporated, and the residue was chromatographed on silica gel (hexane/ethyl acetate, 1:1) to give the title compound as a colourless syrup (800 mg, 77%), $[\alpha]_D$ −53.6°; ¹³C-nmr data: 128.2, 128.0, 127.9 (aromatic), 100.5 (C-1), 74.6 and 74.1 (C-2 and C-4), 73.6 (OCH₂Ph), 73.5 and 73.1 (C-3 and C-5), 72.2 (OCH₂Ph), 64.8 (C-6), and 56.8 (OCH₃).

EXAMPLE 22

1,6-Anhydro-4-O-benzyl-2-chloro-2,3-dideoxy-β-D-ribo-hexopyranose

A.
1,6-Anhydro-4-O-benzyl-2-chloro-2-deoxy-β-D-glucopyranose

A solution of diethylaluminium chloride in hexane (25% w/w, 1.3 ml, 2.0 mmol) was added to a stirred solution of 4-O-benzyl-1,6:2,3-dianhydro-β-D-mannopyranose (Collect. Czech. Chem. Commun., 36 (1971) 2216–2225) (0.3 g, 12 mmol) in toluene (12 ml) under nitrogen at room temperature. The resulting solution was warmed to 45° C. over approximately 0.5 h when t.l.c. indicated complete conversion of the starting material into a mixture of title compound A and a less mobile component presumed to be 1,6 anhydro-4-O-benzyl-3-chloro-3-deoxy-β-D-altropyranose. The reaction was quenched with water and the mixture extracted with aqueous hydrogen chloride (0.3M) and water. The aqueous phases were back-extracted with ethyl acetate and the combined organic phases dried (Na₂SO₄) and concentrated. The residue was chromatographed on silica gel (hexane/ethyl acetate, 4:5) to give the title compound A as a white solid (150 mg, 46%): ¹³C-nmr data: 128.6, 128.0, 127.9 (aromatic), 102.3 (C-1), 78.8 (C-4), 75.4 (C-5), 72.4 and 71.8 (C-3 and PhCH₂O), 66.4 (C-6), and 58.3 (C-2).

B.
1,6-Anhydro-4-O-benzyl-2-chloro-2,3-dideoxy-β-D-ribo-hexopyranose

A mixture of the product from step A (530 mg, 2 mmol), sodium hydride (60%, 100 mg, 2.5 mmol), carbon disulphide (3 ml) and tetrahydrofuran (25 ml) was stirred at room temperature for 10 min. Methyl iodide (3 ml) was added, the mixture was stirred for a further 15 min, and then the reaction was quenched with ethanol. The solution was diluted with ether and washed with water and saturated brine. The aqueous phases were back-extracted with ether. The combined organic phases were dried (Na₂SO₄) and concentrated to a yellow syrup, which was chromatographed on silica gel (hexane/ethyl acetate, 3:1) to yield the xanthate ester of the starting material (240 mg, 0.67 mmol). This compound was dissolved in benzene (10 ml) containing a trace of α-azobisisobutyronitrile. After purging with nitrogen, tributyltin hydride (200 μl, 0.75 mmol) was added and the solution was heated at 80° C. for 10 min, after which time the starting material had been converted to a mixture of the title compound and 1,6 anhydro-4-O-benzyl-2,3-dideoxy-β-D-erythro-hexopyranose in 2:1 ratio (t.l.c.evidence). The reaction mixture was evaporated to dryness and partitioned between acetonitrile and hexane. The acetonitrile phase was evaporated to dryness and the residue chromatographed on silica gel (hexane/acetone, 3:1) to give the title compound (140 mg, 27%) as a colourless syrup, $[\alpha]_D$ +4.3°; $^{13}$C-nmr data: 128.5 and 127.7 (aromatic), 101.8 (C-1), 75.2 (C-5), 71.3 (C-4), 70.4 (PhCH$_2$O), 65.9 (C-6), 52.2 (C-2), and 27.6 (C-3).

EXAMPLE 23

1,6-Anhydro-4-O-benzyl-2-C-cyano-2-deoxy-β-D-glucopyranose

A solution of 4-O-benzyl-1,6:2,3-dianhydro-β-D-mannopyranose (Collect. Czech. Chem. Commun. 36 (1971) 2216-2225) (2.0 g, 8.55 mmol) in toluene (15 ml) was stirred under argon while a solution of diethylaluminium cyanide in toluene (1.0M, 15 ml, 15 mmol) was added. The mixture was warmed to 100° C. over 15 min. The mixture was cooled and then glacial acetic acid was added until effervescence ceased. The resulting gel was partitioned between ethyl acetate and aqueous hydrogen chloride (0.3M). The organic phase was washed with brine and saturated aqueous sodium hydrogen carbonate solution. The resulting emulsion was filtered through normal, then phase separating, filter papers, and the aqueous phase back extracted with ethyl acetate. The combined organic phases were dried (Na$_2$SO$_4$) and evaporated to give the title compound as a yellow solid (1.5 g, 58%). After recrystallisation from ethyl acetate/light petroleum ether it had m.p. 152°-156° C., $[\alpha]_D$ +17.4°; $^{13}$C-nmr data: 98.8 (C-1), 37.5 (C-2), 68.2 (C-3), 74.7 (C-4), 77.4 (C-5), 65.9 (C-6), 71.6 (PhCH$_2$O) and 130.0, 128.5, 128.0 and 127.8 (aromatic); IR (film) 2245 cm$^{-1}$ (C≡N).

EXAMPLE 24

2-Amino-1,6-anhydro-4-O-benzyl-2,3-dideoxy-β-D-ribo-hexopyranose hydrochloride

Lithium aluminium hydride (0.23 g, 6 mmoles) was added to a stirred solution of 1,6-anhydro-2-azido-4-O-benzyl-2,3-dideoxy-β-D-ribo-hexopyranose (see Example 13) (1.17 g, 4.5 mmoles) in diethyl ether (20 ml). After 30 min, excess ethyl acetate was added to destroy the remaining hydride, followed by two drops of water. The resulting grey precipitate was removed by filtration, washed with diethyl ether, and the combined filtrate evaporated to a colourless syrup. Hydrogen chloride gas was passed into a solution of this product in ether containing 5% by volume of ethanol, to precipitate the title compound, which was recovered by filtration and recrystallization from ether/ethanol as white crystals (0.66 g, 54%), m.p. 195°-200° C., $[\alpha]_D$ −50.3°; Calc. for C$_{13}$H$_{18}$ClNO$_3$: C, 57.5; H, 6.7; N, 5.2; Cl, 13.1% Found: C, 57.2; H, 6.9; N, 5.0; Cl, 13.2%; $^{13}$C-nmr data (D$_2$O): 99.7 (C-1), 49.1 (C-2), 25.0 (C-3), 76.3 and 73.1 (C-4 and C-5), 67.4 (C-6), 72.0 (PhCH$_2$O), 138.6 (q, aromatic), 130.1 and 129.7 (aromatic).

EXAMPLE 25

2-Acetamido-1,6-anhydro-4-O-benzyl-2,3-dideoxy-β-D-ribo-hexopyranose

A solution of 1,6-anhydro-2-azido-4-O-benzyl-2,3-dideoxy-β-D-ribo-hexopyranose (see Example 13) in methanol (20 ml) was subjected to transfer hydrogenation by heating under reflux with cyclohexene (7 ml) 5% and palladium on charcoal (0.5 g), added in three portions over a period of 6 h. Acetic anhydride (2.5 ml) was then added to the mixture at room temperature. After 2 h, the mixture was filtered, the filtrate was evaporated, and the residue chromatographed on silica gel to yield the title compound as a syrup (0.35 g, 52%), $[\alpha]_D$ −28.7°; $^{13}$C-nmr data: 101.1 (C-1), 46.4 (C-2), 25.9 (C-3), 74.1 and 73.0 (C-4 and C-5), 65.8 (C-6), 70.5 (PhCH$_2$O), 23.3 (NHCOCH$_3$), 169.2 (NHCOCH$_3$), 137.7 (q-aromatic), 128.5 ($\bar{\times}$2), 127.9, and 127.5 (×2, aromatic).

EXAMPLE 26

1,6-Anhydro-4-O-benzyl-2,3-dideoxy-2-trifluoroacetamido-β-D-ribo-hexopyranose 1,6-Anhydro-2-azido-4-O-benzyl-2,3-dideoxy-β-D-ribo-hexopyranose (see Example 13) (4.07 g) was reduced with lithium aluminium hydride (1.0 g) in diethyl ether (100 ml) as described in Example 24 to yield syrupy amine (3.5 g, 96%). To a solution of this amine in dichloromethane (50 ml) was added pyridine (4 ml) then trifluoroacetic anhydride (3.5 ml). The solution was left at room temperature overnight, washed with saturated aqueous sodium hydrogen carbonate then water, dried (Na$_2$SO$_4$), evaporated, and the resulting product was chromatographed on silica gel to yield the title compound as a yellow syrup (3.1 g, 60%), $[\alpha]_D$ −29.8°; $^{13}$C-nmr data: 100.1 (C-1), 47.2 (C-2), 26.1 (C-3), 73.9 and 72.9 (C-4 and C-5), 66.0 (C-6), 70.8 (PhCH$_2$O), 137.2 (q-aromatic), 128.5 (×2), 128.0, and 127.5 (×2, aromatic).

EXAMPLE 27

1,6-Anhydro-4-O-benzyl-2-N-(carbomethoxy)amino-2,3-dideoxy-β-D-ribo-hexopyranose 1,6-Anhydro-2-azido-4-O-benzyl-2,3-dideoxy-β-D-ribo-hexopyranose (see Example 13) (4.0 g) was reduced with lithium aluminium hydride (1.0 g) in diethyl ether (100 ml) as described in Example 24 to yield syrupy amine (3.6 g, 100%). A solution of this amine in methanol (100 ml) was stirred with potassium carbonate (10 g) while methyl chloroformate (6 ml) was added dropwise. The mixture was left at room temperature overnight, then partitioned between chloroform and water. The organic phase was washed with water, dried (Na$_2$SO$_4$), and evaporated to a crystalline solid. Recrystallisation from ethanol yielded the title compound as white plates, (3.6 g, 80%), m.p. 129°-132° C., $[\alpha]_D$ −26.5°; $^{13}$C-nmr data: 101.3 (C-1), 48.2 (C-2), 26.2 (C-3), 74.1 and 72.8 (C-4 and C-5), 65.8 (C-6), 70.5 (PhCH$_2$O), 51.9 (OCH$_3$), 137.6 (q-aromatic), 128.5 (×2), 127.8, and 127.5 (×2, aromatic).

EXAMPLE 28

1,6-Anhydro-4-O-benzyl-2,3-dideoxy-2-phthalimido-β-D-ribo-hexopyranose 1,6-Anhydro-2-azido-4-O-benzyl-2,3-dideoxy-β-D-ribo-hexoyranose (see Example 13) (1.0 g), phthalic anhydride (0.74 g), triphenylphosphine (1.21 g) and tetrabutylammonium cyanide (0.1 g) were heated under reflux in a nitrogen atmosphere in benzene (50 ml) for 40 h. Methanol (10 ml) was then added and the solution was allowed to stand at room temperature for 15 days. The solution was then evaporated and the residue was chromatographed on silica gel to yield the title compound as a crystaline solid (0.2 g, 14%) from amongst a variety of products (t.l.c.evidence). Recrystallised from ethanol it had m.p. 135°–136° C., $[\alpha]_D - 28.4°$; $^{13}$C-nmr data: 100.4 (C-1), 51.1 (C-2), 25.0 (C-3), 76.5 and 75.7 (C-4 and C-5), 67.4 (C-6), 70.4 (PhCH$_2$O), 167.7 (C=O), 156.0 and 131.8 (q-aromatic), 134.0, 128.3, 127.6, 127.5 and 123.3 (aromatic).

EXAMPLE 29

1,6-Anhydro-4-O-benzyl-2-O-methyl-β-D-allopyranose

A solution of 1,6-anhydro-4-O-benzyl-2-O-methyl-β-D-glucopyranose (0.58 g) (see Example 10) in dichloromethane (10 ml) was stirred with pyridinium dichromate (1.18 g), finely powdered 3 Å molecular sieve (1.8 g, freshly activated at 200° C., 20 torr, 16 h), and acetic acid (2.2 μl). After 0.5 h the mixture was filtered through hyflo, and the residue was washed with dichloromethane. The combined fltrate was evaporated, and the residue suspended in toluene and reconcentrated. This product was column chromatographed on silica gel, eluted with ethyl acetate, to provide the 3-ketone as a colourless syrup (0.58 g); $\gamma_{max}$ 1725 cm$^{-1}$; m/z 264 (M+).

A portion of this 3-ketone (0.54 g) was reduced with sodium borohydride (0.05 g) in ethanol (5 ml) at room temperature for 15 min. The solution was diluted with water (30 ml) and the product was extracted with chloroform (3×15 ml). The extract was dried (MgSO$_4$), and concentrated to a colourless syrup (0.57 g). The title compound was obtained as white needles (0.38 g) m.p. 107°–113° C., following purification by preparative hplc on a silica column eluted with ethyl acetate/hexanes, 1:1.

EXAMPLE 30

1,6-Anhydro-4-O-benzyl-2,3-di-O-methyl-β-D-allopyranose 1,6-Anhydro-4-O-benzyl-2-O-methyl-β-D-allopyranose (0.135 g) (see Example 29) was dissolved in dimethylsulphoxide (0.5 ml) and stirred with powdered potassium hydroxide (0.118 g). Methyl iodide (0.568 g) was added in two portions, and the reaction mixture was left overnight at room temperature. Water (10 ml) was added and the mixture was extracted with chloroform (3×10 ml). The combined extracts were washed with brine, filtered through Whatman 1PS paper, and evaporated to a red oil. This was subjected to preparative t.l.c. on silica gel eluted with ethyl acetate/hexane, 1:1, to yield the title compound as a colourless syrup (0.073 g); $^1$H-nmr data: 7.2–7.5 (m, Ph), 5.6 (d, H-1), 4.8 (m, PhCH$_2$O), 4.55 (m, H-5), 3.3–3.7 (m, H-2,3,4,6,6′), and 3.40 and 3.57 (s, OMe).

EXAMPLE 31

1,6-Anhydro-4-O-benzyl-3-O-ethyl-2-O-methyl-β-D-allopyranose

The title compound was prepared from 1,6-anhydro-4-O-benzyl-2-O-methyl-β-D-allopyranose (0.135 g) (see Example 29) in the same way as described for the 3-O-methyl analogue (see Example 30) but employing ethyl iodide (0.624 g) instead of methyl iodide. It was obtained as a colourless oil (0.089 g); $^1$H-nmr data: 7.2–7.5 (m, Ph), 5.6 (d, H-1), 4.8 (m, PhCH$_2$O), 4.55 (m, H-5), 1.25 (t, CH$_2$CH$_3$), and 3.4–3.7 (m, remaining protons).

COMPOSITION EXAMPLE 1

Granule formulation of 1,6-anhydro-4-O-(2-chlorobenzyl)-3-deoxy-2-O-methyl-β-D-ribo-hexopyranose Granules are prepared by blending china clay with "Polyfon" H and "Synperonic" NP8 and extruding the mixture to form granules. The remaining constituents are dissolved in methanol, the solution applied to the granules and allowed to evaporate to give granules of the following composition:

|  | Amount (grams) |
| --- | --- |
| Active ingredient | 10 |
| "Topanol" O | 10 |
| "Waxoline" Black | 10 |
| "Synperonic" NP8 | 2.4 |
| China Clay | to 1 kg |

The materials represented by the various trade names in the above list are as follows:

Topanol O—An anti-oxidant comprising di-tertiary-butyl-p-hydroxytoluene

Waxoline Black 5BP—A mixture of azo and other solvent-soluble dyes acting as an absorbent for ultraviolet light Synperonic NP 8—A surfactant comprising a condensate of eight molar proportions of ethylene oxide with p-nonylphenol Polyfon H—A dispersing agent comprising sodium lignosulphonate.

COMPOSITION EXAMPLE 2

Emulsifiable concentrate of 1,6-anhydro-4-O-(2-Chlorobenzyl)-3-deoxy-2-O-methyl-β-D-ribohexopyranose A concentrate is prepared by agitating the constituents together until a homogeneous solution is obtained of the following compositions:

|  | Amount (grams) |
| --- | --- |
| Active ingredient | 100 |
| "Waxoline" Black | 10 |
| Calcium dodecylbenzene-sulphonate (in butanol solution) | 30 |
| "Synperonic" NP13 | 20 |
| "Topanol" O | 10 |
| Solvesso 150 | to 1 liter |

For explanation of the trade-named components Waxoline Black and Polyfon see Composition Example 1:

Synperonic NP13—A surface-active agent comprising a condensate of p-nonylphenol with thirteen molar proportions of ethylene oxide.

Solvesso 150—An aromatic solvent comprising a mixture of alkylbenzenes.

We claim:

1. Herbicidal and/or plant growth regulatory compositions comprising, together with a carrier and/or surface-active agent, an effective amount of at least one herbicidal and/or plant growth regulatory active agent selected from compounds of formula (I)

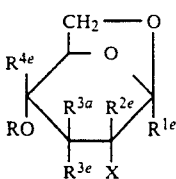

(I)

in which R represents a substituted or unsubstituted aralkyl group,

X represents an O-, N- or S-linked organic group, a substituted or unsubstituted hydrocarbyl group, a halogen atom, a hydroxy, amino, alkoxyamino, nitro, cyano, azido, sulpho or phospho group, $R^{1e}$ represents a hydrogen atom or a substituted or unsubstituted hydrocarbyl group, or a formyl group;

$R^{2e}$ represents a hydrogen atom, a hydroxy group or a substituted or unsubstituted hydrocarbyl or O-linked hydrocarbyl group or, together with the group X, $R^{2e}$ may represent a ketonic oxygen atom —O— or a group of formula —$CH_2O$—;

$R^{3a}$ represents a hydrogen atom, a hydroxy group or a substituted or unsubstituted alkoxy, alkenyloxy, aralkoxy or $C_{1-4}$ hydrocarbyl group;

$R^{3e}$ represents a hydrogen atom, a hydroxy group or a substituted or unsubstituted hydrocarbyl or O-linked hydrocarbyl group; and $R^{4e}$ represents a hydrogen atom or a substituted or unsubstituted hydrocarbyl group, and enantiomers and salts thereof.

2. Compositions as claimed in claim 1, in which R is a group of formula

$Ar—(CR^aR^b)_n—$ (II)

in which n is from 1 to 6, and where n is more than 1 each adjacent repeating unit may be the same as or different from its neighbouring unit;

$R^a$ and $R^b$, which may be the same of different, are selected from hydrogen and halogen atoms and phenyl and $C_{1-6}$ alkyl groups; and Ar represents a substituted or unsubstituted phenyl, naphthyl, anthryl, quinolyl, pyridyl, furyl, thienyl, benzimidazolyl, benzothienyl, xanthenyl, phenylthio or phenylsulphenyl group.

3. Compositions as claimed in claim 1, wherein R is a group of formula

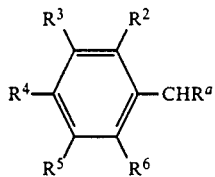

in which $R^a$ represents a hydrogen atom or a methyl group; and $R^2$ to $R^6$, which may be the same or different, are selected from hydrogen and halogen atoms, and alkyl, alkoxy, substituted alkyl, substituted alkoxy, carbocyclicaryl, heterocyclicaryl, alkylthio, cyano, nitro, sulpho, carboxy and esterified carboxy groups.

4. Compositions as claimed in claim 3, wherein in the group R one of the substituents $R^2$ and $R^6$ is a halogen atom or a substituted or unsubstituted alkyl group and the other substituents $R^3$, $R^4$ and $R^5$ (and the remaining $R^2$ or $R^6$ substituent) are independently selected from hydrogen, halogen and a substituted or unsubstituted alkyl group.

5. Compositions as claimed in claim 1 wherein

R is a substituted or unsubstituted benzyl group;

X is a halogen atom, or a hydroxy, $C_{1-3}$ alkoxy, $C_{2-3}$ alkenyloxy, aralkoxy, alkylthio, $C_{1-3}$ alkyl, methoxy$C_{1-3}$-alkyl or azido group;

$R^{1e}$ is a hydrogen atom or a $C_{1-4}$ alkyl group;

$R^{2e}$ is a hydrogen atom;

$R^{3a}$ and $R^{3e}$ are independently a hydrogen atom or a hydroxy, $C_{1-4}$ alkoxy or ar-$C_{1-4}$-alkoxy group; and $R^{4e}$ is a hydrogen atom or a $C_{1-4}$ alkyl group.

6. Compositions of claim 1, wherein

R represents a benzyl group substituted or unsubstituted in the phenyl ring;

X represents a $C_{1-13}$ hydrocarbyloxy or alkyl group, or an azido group, or a halogen atom;

$R^{1e}$ represents a hydrogen atom or a substituted or unsubstituted $C_{1-6}$ alkyl group;

$R^{2e}$, $R^{3a}$, and $R^{3e}$ all represent hydrogen atoms; and $R^{4e}$ represents a hydrogen atom or a $C_{1-4}$ alkyl group.

7. A method of combating weeds which comprises applying to the weeds, or to a habitat thereof, a composition according to claim 1.

8. A method as claimed in claim 7, wherein the weeds are combatted in crops of useful plants.

9. A method according to claim 8, wherein the weeds are combatted in soya, rape, sugar-beet, cotton, wheat, maize and rice crops.

10. A method for preparing compositions as claimed in claim 1, which method comprises (1) preparing one or more active ingredient according to any of the following methods:

A. cyclising a compound of formula (Va) or (Vb)

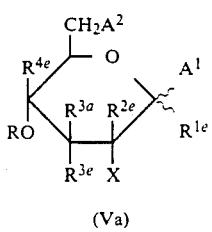 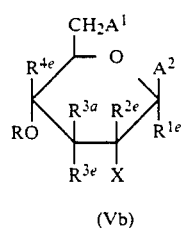

(Va) (Vb)

(in which

R, X, $R^{1e}$, $R^{2e}$, $R^{3a}$, $R^{3e}$ and $R^{4e}$ are as defined in claim 1, or represent protected forms thereof, $A^2$ is an O-linked group capable of being partially split off to leave a negative oxide anion, and $A^1$ is a group capable of being completely spilt off to leave a positive carbonium cation) or an enantiomer thereof;

B. aralkylating a compound of formula (VI)

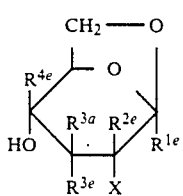

(VI)

or a corresponding alkali metal alkoxide, (in which X, $R^{1e}$, $R^{2e}$, $R^{3a}$, $R^{3e}$ and $R^{4e}$ are as defined in claim 1, or represent protected forms thereof), or an enantiomer thereof;

C. preparing compounds wherein X represents an O-linked organic group and/or wherein $R^{3a}$ represents a substituted or unsubstituted alkoxy, alkenyloxy or aralkoxy group and/or where $R^{2e}$ and/or $R^{3e}$ represents a substituted or unsubstituted O-linked hydrocarbyl group: reacting a corresponding compound of formula (I) wherein X and/or $R^{3a}$ and/or $R^{2e} R^{3e}$ represents a hydroxy group, and the remainder of X, R, $R^{1e}$, $R^{2e}$, $R^{3a}$, $R^{3e}$ and $R^{4e}$ are as defined in claim 1 or represent protected forms thereof, or an enantiomer thereof, or a corresponding alkali metal alkoxide thereof, with a compound serving to introduce respectively an O-linked organic group at X, a substituted or unsubstituted alkoxy, alkenyloxy or aralkoxy group at $R^{3a}$, or a substituted or unsubstituted O-linked hydrocarbyl group at $R^{2e}$ or $R^{3e}$;

D. preparing compounds wherein X represents a hydroxy group: reducing a compound of Formula (I) wherein X together with the group $R^{2e}$ represents a ketonic oxygen atom, and R, $R^{1e}$, $R^{3a}$, $R^{3e}$ and $R^{4e}$ are as defined in claim 1 or represent protected forms thereof, or an enantiomer thereof;

E. preparing compounds wherein X together with the group $R^{2e}$ represents a ketonic oxygen atom and the groups $R^{1e}$, $R^{3a}$, $R^{3e}$ and $R^{4e}$ all represent hydrogen atoms; reaction of levoglucosenone (IX)

(IX)

with an alcohol or formula (X)

ROH  (X)

wherein R is as defined in claim 1;

F. preparing compounds wherein R is as defined in claim 1, $R^{1e}$, $R^{2e}$, $R^{3a}$, $R^{3e}$ and $R^{4e}$ all represent hydrogen atoms and X is as defined in claim 1 with the exception of the ketonic oxygen atom and the group —CH$_2$O— with $R^{2e}$: reacting a compound of formula (XII)

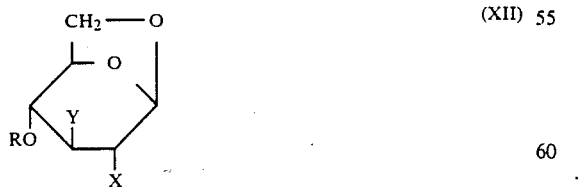

(XII)

(in which R is as defined in claim 1 for formula (I) or represents a protected form thereof, Y represents a S-methyldithiocarbonate or phenylthionocarbonate group, and X is as defined in claim 1 with the exception of the ketonic oxygen atom and the group —CH$_2$O— with $R^{2e}$, or represents a protected form thereof), or an enantiomer thereof, with trialkyltin hydride G. preparing compounds wherein R is as defined in claim 1, $R^{1e}$, $R^{2e}$, $R^{3e}$ and $R^{4e}$ all represent hydrogen atoms, $R^{3a}$ represents a hydroxy group and X, which is the same as the group OR, represents a substituted or unsubstituted aralkoxy group:

2,4-di-O-aralkylating levoglucosan  (XIII)

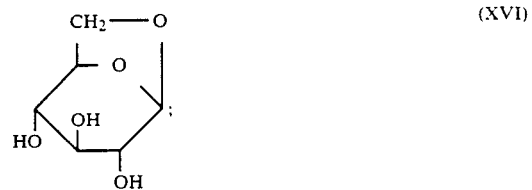

(XVI)

H. preparing compounds wherein R, $R^{1e}$ and $R^{4e}$ are as defined in claim 1, $R^{2e}$ and $R^{3e}$ all represent hydrogen atoms, $R^{3a}$ represents a hydroxy group and X represents an O-linked organic group, a substituted or unsubstituted hydrocarbyl group, a halogen atom, or a hydroxy, amino, cyano or azido group; reacting a D-manno-epoxide of formula (XIV)

(XIV)

wherein R, $R^{1e}$ and $R^{4e}$ are as defined in claim 1 or represent protected forms thereof, or an enantiomer thereof, with a compound serving to selectively introduce the group X as defined in claim 1 at the 2-position;

I. preparing compounds wherein $R^{2e}$ represents a hydrogen atom and X represents an S-linked organic group or an azido group; reacting a compound of formula (XVI)

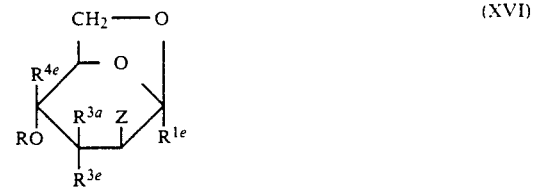

(XVI)

wherein R, $R^{1e}$, $R^{3a}$, $R^{3e}$ and $R^{4e}$ are as defined in claim 1 or represent protected forms thereof, and Z represents a nucleophilically exchangeable group with an organic thiol of formula (XVII)

R'SH  (XVII)

(wherein R' represents an organic group), or a reactive derivative thereof, or with sodium azide;

J. preparing compounds wherein X represents a mono- or di-alkylamino, mono or di-aralkylamino, trialkylammonium, carboxamido group or dicarboximido and R, $R^{1e}$, $R^{2e}$, $R^{3a}$, $R^{3e}$ and $R^{4e}$ are as defined in claim 1: reacting a compound of formula (I), wherein X represents an amino group and R, $R^{1e}$, $R^{2e}$, $R^{3e}$ and $R^{4e}$ are as defined in claim 1 or represent protected forms thereof, with a compound capable of converting said amino group to a mono- or di-alkylamino, mono- or di-araikylamino, tri-alkylammonium, carboxamido or dicarboximido group;

K. preparing compounds wherein X represents a carboxamido or dicarboximido group and R, $R^{1e}$, $R^{2e}$, $R^{3a}$, $R^{3e}$ and $R^{4e}$ are as defined in claim 1: reacting a compound of formula (I) wherein X represents an azido group and R, $R^{1e}$, $R^{2e}$, $R^{3a}$, $R^{3e}$ and $R^{4e}$ are as defined in claim 1 or represent protected forms thereof, or an activated derivative thereof, with an anhydride reagent corresponding to the desired carboxamido or dicarboximido group;

L. preparing compounds wherein X represents an amino group and R, $R^{1e}$, $R^{2e}$, $R^{3a}$, $R^{3e}$ and $R^{4e}$ are as defined in claim 1 or represent protected forms thereof;

M. preparing compounds wherein X together with the group $R^{2e}$ represents a group of formula —CH$_2$O— and R, $R^{1e}$, $R^{3a}$, $R^{3e}$ and $R^{4e}$ are as defined in claim 1: reacting a corresponding compound of formula (I) wherein X together with a group $R^{2e}$ represents a ketonic oxygen atom and R, $R^{1e}$, $R^{3a}$, $R^{3e}$ and $R^{4e}$ are as defined in claim 1 or represent protected forms thereof, with diazomethane;

N. preparing for the preparation of compounds wherein $R^{3a}$ is a hydrogen atom and $R^{3e}$ represents a hydroxy group, and X, R, $R^{1e}$, $R^{2e}$ and $R^{4e}$ are as defined in claim 1: reducing a compound of formula (XVIII)

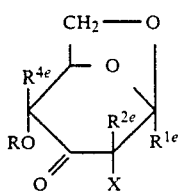

(XVIII)

(wherein X, R, $R^{1e}$, $R^{2e}$ and $R^{4e}$ are as defined in claim 1 or represent protected forms thereof) with a reducing agent capably of selectively forming the β-D-allopyranose reduction product;

O. preparing compounds wherein $R^{1e}$ represents a substituted or unsubstituted hydrocarbyl group and X, R, $R^{2e}$, $R^{3a}$, $R^{3e}$ and $R^{4e}$ are as defined in claim 1: ring-closing a vic-dihydroxy-protected form of a compound of formula (XIX)

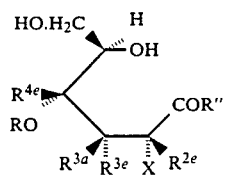

(XIX)

(wherein X, R, $R^{2e}$, $R^{3a}$, and $R^{3e}$ and $R^{4e}$ are as defined in claim 1 or represent protected forms thereof, and R″ represents a substituted or unsubstituted hydrocarbyl group); or P. preparing salts of compounds of formula (I) and enantiomers thereof: reacting a compound of formula (I) or enantiomer thereof, initially obtained, with an acid or base to form the desired salt; and (2) subsequently admixing a suitable amount of at least one of said compounds obtained thereby with a carrier and/or surface-active agent.

11. A method as claimed in claim 10, wherein the starting compound of Formula (XIX) is obtained by oxidation of a corresponding compound having a —CH(OH)R″ terminal group, said starting alcohol having been obtained by either (i) Grignard cleavage of tetrahydropyran derivative of formula (XX)

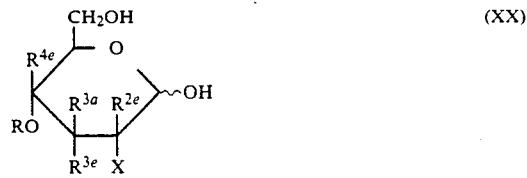

(XX)

(in which

R represents a substituted or unsubstituted aralkyl group,

X represents an O-, N- or S-linked organic group, a substituted or unsubstituted hydrocarbyl group, a halogen atom, a hydroxy, amino, alkoxyamino, nitro, cyano, azido, sulpho or phospho group, or together with the group $R^{2e}$, X may represent a ketonic oxygen atom —O— or a group of formula —CH$_2$O—;

$R^{2e}$ represents a hydrogen atom; a hydroxy group or a substituted or unsubstituted hydrocarbyl or O-linked hydrocarbyl group, or, together with the Group I, $R^{2e}$ may represent a ketonic oxygen atom —O— or a group of formula —CH$_2$O—;

$R^{3a}$ represents a hydrogen atom, a hydroxy group or a substituted or unsubstituted alkoxy, alkenyloxy, aralkoxy or $C_{1-4}$ hydrocarbyl group;

$R^{3e}$ represents a hydrogen atom, a hydroxy group or a substituted or unsubstituted hydrocarbyl or O-linked hydrocarbyl group; and $R^{4e}$ represents a hydrogen atom or a substituted or unsubstituted hydrocarbyl group; and enantiomers and salts thereof, or represent protected forms thereof), with a Grignard reagent of formula R″MgX (wherein X is a halogen atom and R″ is as defined in claim 9 (O)), or (ii) Grignard reaction of a vic-dihydroxy-protected form of an aldehyde compound of formula (XXII)

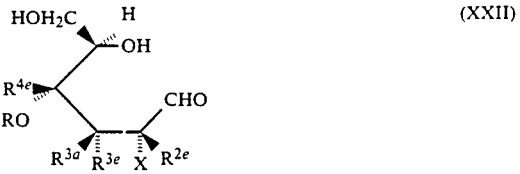

(XXII)

(wherein X, R, $R^{2e}$, $R^{3a}$, $R^{3e}$ and $R^{4e}$ are as defined above or represent protected forms thereof), with a similar Grignard reagent.

12. A method as claimed in claim 11, wherein the starting compound of formula (XX) is obtained by reaction of a corresponding compound of formula (I) as defined in claim 1 wherein $R^{1e}$ is a hydrogen atom, with acetic anhydride under acidic conditions to cleave the C—O axial bond at the 1-position and generate acetoxy groups at the 1- and 6-carbon atoms, to form a compound of formula (XXIII)

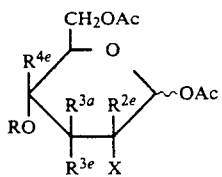
(XXIII)

(in which
R represents a substituted or unsubstituted aralkyl group,
X represents an O-, N- or S-linked organic group, a substituted or unsubstituted hydrocarbyl group, a halogen atom, a hydroxy, amino, alkoxyamino, nitro, cyano, azido, sulpho or phospho group, or together with the group $R^{2e}$, X may represent a ketonic oxygen atom —O— or a group of formula —CH$_2$O—;
$R^{2e}$ represents a hydrogen atom, a hydroxy group or a substituted or unsubstituted hydrocarbyl of O-linked hydrocarbyl group, or, together with the group X, $R^{2e}$ may represent a ketonic oxygen atom —O— or a group of formula —CH$_2$O—;
$R^{3a}$ represents a hydrogen atom, a hydroxy group or a substituted or unsubstituted alkoxy, alkenyloxy, aralkoxy or $C_{1-4}$ hydrocarbyl group;
$R^{3e}$ represents a hydrogen atom, a hydroxy group or a substituted or unsubstituted hydrocarbyl or O-linked hydrocarbyl group; and
$R^{4e}$ represents a hydrogen atom or a substituted or unsubstituted hydrocarbyl group;
and enantiomers and salts thereof), followed by conventional deacylation; and the starting compound of formula (XXIII) is obtained by oxidation of a vic-dihydroxy protected form of a compound of formula (XXI)

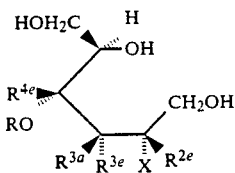
(XXI)

(wherein X, R, $R^{2e}$, $R^{3a}$, $R^{3e}$ and $R^{4e}$ are as defined above).

13. A method as claimed in claim 10, where in the compound of formula (VI) and the corresponding alkali metal alkoxides of said compound $R^{2e}$, $R^{3a}$, $R^{3e}$ and $R^{4e}$ are each hydrogen, $R^{1e}$ is hydrogen or lower alkyl, and X is lower alkoxy.

14. A method as claimed in claim 11, where in the compound of formula (XX) $R^{2e}$, $R^{3a}$, $R^{3e}$ and $R^{4e}$ are each hydrogen, R is a substituted or unsubstituted benzyl group and X is a lower alkoxy group, with the proviso that when R is a substituted or unsubstituted aralkyl, X is hydroxyl or methoxy, and $R^{1e}$, $R^{2e}$ and $R^{4e}$ are each hydrogen, and when one of $R^{3a}$ or $R^{3e}$ is hydrogen the other of $R^{3a}$ or $R^{3e}$ is not alkoxy, substituted or unsubstituted benzyloxy or napthyl methoxy.

15. A method as claimed in claim 11, where in the compound of formula (XX) or (XXII) $R^{2e}$, $R^{3a}$, $R^{3e}$ and $R^{4e}$ are each hydrogen, R is a substituted or unsubstituted benzyl and X is a lower alkoxy and corresponding compounds in which the vic-hydroxy groups are protected by an acetone acetal.

16. A method as claimed in claim 12, where in the compound of formula (XX) and (XXII) $R^{2e}$, $R^{3a}$, $R^{3e}$ and $R^{4e}$ are each hydrogen, R is a substituted or unsubstituted benzyl and X is a lower alkoxy group and corresponding compounds in which the vic-hydroxy groups are protected by an acetone acetal.

17. A method as claimed in claim 12, where in the compound of formula (XXIII) $R^{2e}$, $R^{3a}$ and $R^{4e}$ are each hydrogen, R is a substituted or unsubstituted benzyl and X is a lower alkoxy group, with the proviso that when R is a substituted or unsubstituted aralkyl, X is a hydroxy or methoxy, and $R^{1e}$, $R^{2e}$ or $R^{4e}$ are each hydrogen, and when one of $R^{3a}$ or $R^{3e}$ is hydrogen, the other of $R^{3a}$ or $R^{3e}$ is not an alkoxy, substituted or unsubstituted benzyloxy or napthyl methoxy.

18. A process according to claim 10, further comprising subsequently admixing a suitable amount of at least one of said compounds obtained with a carrier and/or surface-active agent and additional ingredients to obtain a herbicidal and/or plant growth regulatory composition.

19. A process according to claim 10, further comprising subsequently splitting off or converting any protective groups to produce the derived compound in (1) (A), (1) (B), (1) (C), (1) (D), (1) (F), (1) (H), (1) (I), (1) (J), (1) (K), (1) (L), (1) (M), (1) (N), or (1) (O), or any combination thereof.

20. A process according to claim 19 further comprising subsequently splitting or converting any protective groups to produce the desired compound.

21. Compounds of formula (Ia)

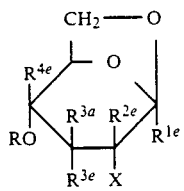
(Ia)

(in which
R represents a substituted or unsubstituted aralkyl group;
X represents an O-, N- or S-linked organic group, a substituted or unsubstituted hydrocarbyl group, a halogen atom, a hydroxy, amino, alkoxyamino, cyano, azido, sulpho or phosphor group, or together with the group $R^{2e}$, X may represent a ketonic oxygen atom —O— or a group of formula —CH$_2$O—;
$R^{1e}$ represents a hydrogen atom or a substituted or unsubstituted hydrocarbyl group, or a formyl group;
$R^{2e}$ represents a hydrogen, atom, a hydroxy group or a substituted or unsubstituted hydrocarbyl or O-linked hydrocarbyl group; or, together with the group X, $R^{2e}$ may represent a ketonic oxygen atom —O— or a group of formula —CH$_2$O—;
$R^{3a}$ represents a hydrogen atom, a hydroxy group, or a substituted or unsubstituted alkoxy, alkenyloxy, aralkoxy or $C_{1-4}$ hydrocarbyl group;
$R^{3e}$ represents a hydrogen atom, a hydroxy group or a substituted or unsubstituted hydrocarbyl or O-linked hydrocarbyl group; and $R^{4e}$ represents a hydrogen atom or a substituted or unsubstituted hydrocarbyl group, with the proviso that, when R represents a benzyl group and $R^{1e}$, $R^{2e}$ and $R^{4e}$ all represent hydrogen atoms, then if (i) $R^{3a}$ and $R^{3e}$ each represents a hydrogen atom, X cannot represent a hydroxy or benzyloxy group;

(ii) $R^{3a}$ represents a hydroxy group and $R^{3e}$ represents a hydrogen atom, X cannot represent a isothiocyanato, S-methyldithiocarbanato, ureido, thioureido, methyl, allyl, benzyloxy, tetrahydropyranyloxy, amino, acetamido, azido, $NHC(S)SCH_3$, hydroxy or methoxy group, a 3-hydroxy-prop-1-enyl, 3-hydroxy-2-methyl-prop-1-enyl or 3-hydroxyprop-1-ynyl group or a silylated derivative of such groups, or a halogen atom;

(iii) $R^{3a}$ represents a benzyloxy group and $R^{3e}$ represents a hydrogen atom, X cannot represent a hydroxy, benzyloxy, benzyloxy, prop-1-enyloxy, allyloxy, methoxy, acetoxy, azido, acetamido or tetrahydropyranyloxy group, or a halogen atom or together with the group $R^{2e}$ a ketonic oxygen atom;

(iv) $R^{3a}$ represents a propoxy group and $R^{3e}$ represents a hydrogen atom, X cannot represent a hydroxy, benzyloxy or tetrahydropyranyloxy group;

(v) $R^{3a}$ represents a hydrogen atom and $R^{3e}$ represents a hydroxy group, X cannot represent a hydroxy or benzyloxy group, or a fluorine atom;

(vi) $R^{3a}$ represents a methoxy group and $R^{3e}$ represents a hydrogen atom, X cannot represent a methyl, methoxy or benzyloxy group;

(vii) $R^{3a}$ represents a dodecyloxy or 2-butenyl group and $R^{3e}$ represents a hydrogen atom, X cannot represent a benzyloxy group;

(viii) $R^{3a}$ represents a triphenylmethyl group and $R^{3e}$ represents a hydrogen atom, X cannot represent an acetylamino group; and (ix) when $R^{3a}$ represents a hydrogen atom, and $R^{3e}$ represents a benzyloxy group, then X cannot represent a benzyloxy group;

and with the further proviso that when OR and $R^{3a}$ each represents a benzyloxy group, $R^{1e}$, $R^{2e}$ $R^3$ each represents a benzyloxy group, $R^{1e}$, $R^{2e}$, $R^{3e}$ represent hydrogen atoms, and $R^{4e}$ represents a methyl group, X cannot represent a methyl group, and with the second further provision that when OR and $R^{3a}$ each represents a p-halo- or p-methyl-benzyloxy group and $R^{1e}$, $R^{2e}$, $R^{3e}$ represent hydrogen atoms, X cannot represent respectively a p-halo- or p-methyl-benzyloxy group, and with the third further proviso that when R is a substituted or unsubstituted aralkyl, X is a hydroxy or methoxy group, and $R^{1e}$, $R^{2e}$ and $R^{4e}$ each are hydrogen, then if one of $R^{3a}$ or $R^{3e}$ is hydrogen the other of $R^{3a}$ or $R^{3e}$ is not an alkoxy, substituted or unsubstituted benzyloxy or naphthyl methoxy, and enantiomers and salts thereof, and with the fourth further proviso that when R represents a trityl group, X represents an acetlyamino group, and $R^2$, $R^{2e}$, $R^{3e}$ and $R^{4e}$ represent hydrogen atoms, then $R^{3a}$ cannot represent a hydroxy or benzyloxy group).

22. Compounds of claim 21, wherein R is a group formula

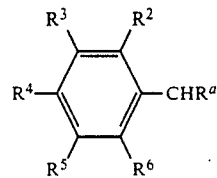

in which $R^a$ represents a hydrogen atom or a methyl group and $R^2$ to $R^6$, which may be the same or different, are selected from hydrogen and halogen atoms, and alkyl, alkoxy, substituted alkyl, substituted alkoxy, carbocyclicaryl, heterocyclicaryl, alkylthio, cyano, nitro, sulpho, carboxy and esterified carboxy groups;

X is a halogen atom, or a hydroxy, $C_{1-3}$ alkoxy, $C_{2-3}$ alkenyloxy, aralkoxy, alkylthio, $C_{1-3}$ alkyl, methoxy- $C_{1-3}$-alkyl or azido group;

$R^{1e}$ is a hydrogen atom or a $C_{1-4}$ alkyl group;

$R^{2e}$ is a hydrogen atom;

$R^{3a}$ and $R^{3e}$ are independently a hydrogen atom or a hydroxy, $C_{1-4}$ alkoxy or ar-$C_{1-4}$-alkoxy group; and $R^{4e}$ is a hydrogen atom or a $C_{1-4}$ alkyl group, with the proviso that when R is as defined above, X is a hydroxy or a methoxy, and $R^{1e}$ and $R^{4e}$ each are hydrogen, then if one of $R^{3a}$ or $R^{3e}$ is hydrogen, the other of $R^{3a}$ or $R^{3e}$ is not $C_{1-4}$ alkoxy or substituted or unsubstituted benzyloxy or naphthyl methoxy.

* * * * *

UNITED STATES PATENT AND TRADEMARK OFFICE
CERTIFICATE OF CORRECTION

PATENT NO. : 5,047,518

DATED : September 10, 1991

INVENTOR(S) : Richard H. Furneaux, et al.

It is certified that error appears in the above-identified patent and that said Letters Patent is hereby corrected as shown below:

Column 8, line 65: "alchohols" should read --alcohols--.

Column 10, line 50: "Obenzylidene" should read --O-benzylidene--.

Column 13, line 32: "is a" should read --is as--.

Column 18, line 63: "CHO." should read --CHO--.

Column 22, line 58: "Lowest" should read --+ Lowest--.

Column 35, line 8: "arabinohexopyranose" should read --arabino-hexopyranose--.

Column 51, line 35: "($ArCH_2O$)" should read --($Ar\underline{C}H_2O$)--.

Column 51, line 35: "($OCH_3$)" should read --($O\underline{C}H_3$)--.

UNITED STATES PATENT AND TRADEMARK OFFICE
CERTIFICATE OF CORRECTION

PATENT NO. : 5,047,518

DATED : September 10, 1991

INVENTOR(S) : Richard H. Furneaux, et al.

It is certified that error appears in the above-identified patent and that said Letters Patent is hereby corrected as shown below:

Column 51, lines 35 & 36:

Correction should read ($\underline{C}H_2CH_2CH_3$), 23.7 ($\overline{C}$-3), 15.5 ($CH_2\underline{C}H_2CH_3$) and 14.3 ($CH_2CH_2\underline{C}H_3$).

Column 54, line 22: "($OCH_2Ph$)" should read --($O\underline{C}H_2Ph$)--.

Signed and Sealed this

Twenty-ninth Day of June, 1993

Attest:

MICHAEL K. KIRK

*Attesting Officer*   Acting Commissioner of Patents and Trademarks